US008569267B2

(12) United States Patent
Cid-Núñez et al.

(10) Patent No.: US 8,569,267 B2
(45) Date of Patent: *Oct. 29, 2013

(54) TETRACYCLIC TETRAHYDROFURAN DERIVATIVES CONTAINING CYCLIC AMINE SIDE CHAIN

(75) Inventors: José Maria Cid-Núñez, Toledo (ES); Andrés Avelino Trabanco-Suárez, Toledo (ES)

(73) Assignee: Janssen Pharmaceutica, NV (BE)

( * ) Notice: Subject to any disclaimer, the term of this patent is extended or adjusted under 35 U.S.C. 154(b) by 789 days.

This patent is subject to a terminal disclaimer.

(21) Appl. No.: 11/917,840

(22) PCT Filed: Jun. 16, 2006

(86) PCT No.: PCT/EP2006/063273
§ 371 (c)(1),
(2), (4) Date: Dec. 17, 2007

(87) PCT Pub. No.: WO2006/134163
PCT Pub. Date: Dec. 21, 2006

(65) Prior Publication Data
US 2008/0262076 A1    Oct. 23, 2008

(30) Foreign Application Priority Data
Jun. 17, 2005   (EP) ..................... 05105398

(51) Int. Cl.
*A01N 57/00*   (2006.01)
*A61K 31/675*  (2006.01)
*C07D 207/06*  (2006.01)
*C07D 295/02*  (2006.01)

(52) U.S. Cl.
USPC ............................ 514/91; 548/579

(58) Field of Classification Search
USPC ............................ 514/91; 548/579
See application file for complete search history.

(56) References Cited

U.S. PATENT DOCUMENTS

| | | | |
|---|---|---|---|
| 6,511,976 B1 * | 1/2003 | Andres-Gil et al. | 514/232.8 |
| 6,699,858 B2 * | 3/2004 | Andres-Gil et al. | 514/228.2 |
| 2008/0214572 A1 * | 9/2008 | Fernandez-Gadea et al. | 514/255.04 |

FOREIGN PATENT DOCUMENTS

| | | |
|---|---|---|
| WO | WO 97/38991 A | 10/1997 |
| WO | WO 99/19317 A | 4/1999 |
| WO | WO 03/040122 A | 5/2003 |
| WO | WO 03/048146 A1 | 6/2003 |
| WO | WO 03/048147 A2 | 6/2003 |

OTHER PUBLICATIONS

Green, et al., Treatment of Schizophrenia and Comorbid Substance Use Disorder, Current Drug Targets—CNS & Neurological Disorders, 129-139 (2002).*

International Search Report and Written Opinion from the International Searching Authority, dated Nov. 28, 2007, 10 pages.
Meert, T.F., et al., "Partial and Complete Blockade of 5-Hydroxytrytophan (5-HTP)-Induced Head Twitches in the Rat: A Study of Ritanserin (R 55 667), Risperidone (R 64 766), and Related Compounds", Drug Development Research, (1988), vol. 13, pp. 237-244.
Monkovic, Y.G., et al., "Substituted Tetrahydrofurfurylamines as Potential Antidepressants", Journal of Medicinal Chemistry, (1973), vol. 16, No. 4, pp. 403-407.
Stella, V.J., et al., "Prodrugs Do They Have Advantages in Clinical Practice?", Drugs, (1985), vol. 29, pp. 455-473.
Fishman, M., "Studies in Alkylation. I. Synthesis and Reactions of Spiro{Oxirane-2,4'-Piperidines}", Journal of Heterocyclic Chemistry, (1968), vol. 5, No. 4, pp. 467-469.
Stella, V.J., et al., "Prodrugs: the control of drug delivery via bioreversible chemical modification", Drug Delivery Systems, (1980), pp. 112-176, ISBN 0-19502700-0, Oxford University Press, Inc.
FernéMandez, J., et al., "Discovery of New Tetracyclic Tetrahydrofuran Derivatives As Potential Broad-Spectrum Psychotropic Agents", Journal of Medicinal Chemistry, (2005), vol. 48, No. 6, pp. 1709-1712.
Cid J et al: "Synthesis and structure-activity relationship of 2-(aminoalkyl)-3,3a,8,12b-tetrahydro-2H-di benzocyclohepta[1,2-b]furan derivatives: a novel series of 5-HT2A-2C receptor antagonists" Bioorganic & Medicinal Chemistry Letters, Oxford, GB, vol. 14, No. 11, Jun. 7, 2004, pp. 2765-2771, XP004841284 ISSN: 0960-894X.

* cited by examiner

Primary Examiner — Erich A Leeser

(57) ABSTRACT

This invention concerns novel substituted tetracyclic tetrahydrofuran derivatives containing a cyclic amine side chain with binding affinities towards dopamine receptors, in particular dopamine $D_2$ receptors, towards serotonin receptors, in particular 5-$HT_{2A}$ and 5-$HT_{2C}$ receptors, and pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.
The compounds according to the invention can be represented by general Formula (I)

(I)

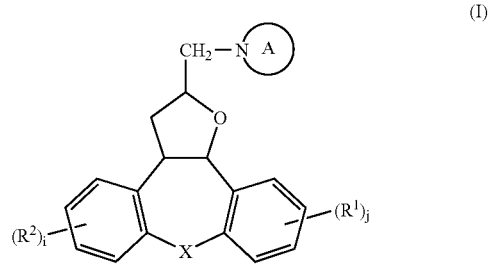

and comprises also a pharmaceutically acceptable acid or base addition salt thereof, an N-oxide form thereof or a quaternary ammonium salt thereof, wherein all substituents are defined as in Claim 1.

7 Claims, No Drawings

TETRACYCLIC TETRAHYDROFURAN DERIVATIVES CONTAINING CYCLIC AMINE SIDE CHAIN

FIELD OF THE INVENTION

This invention concerns novel substituted tetracyclic tetrahydrofuran derivatives containing a cyclic amine side chain with binding affinities towards dopamine receptors, in particular dopamine $D_2$ receptors, towards serotonin receptors, in particular 5-$HT_{2A}$ and 5-$HT_{2C}$ receptors, and pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.

BACKGROUND PRIOR ART

WO 97/38991, published Oct. 23, 1997 (Janssen Pharmaceutica N.V.) discloses substituted tetracyclic tetrahydrofuran derivatives that may be used as therapeutic agents in the treatment or prevention of CNS disorders, cardiovascular disorders or gastrointestinal disorders. In particular, the compounds show affinity for the serotonin 5-$HT_2$ receptors, particularly for the 5-$HT_{2A}$ and 5-$HT_{2C}$-receptors. A number of compounds with a cyclic amine side chain were disclosed which are excluded from this application by way of a disclaimer. The same compounds were also disclosed in Cid J. et al. Bioorganic & Medicinal Chemistry Letters, 14 (2004) 2765-2771.

WO 99/19317, published Apr. 22, 1999 (Janssen Pharmaceutica N.V.) discloses substituted tetracyclic tetrahydrofuran derivatives with a specific halogen substitution pattern on the dibenzoazepine, dibenzooxepine, dibenzothiepine or dibenzosuberane ring. The compounds are useful in the treatment or prevention of CNS disorders, cardiovascular disorders or gastrointestinal disorders and show a faster onset of action over the compounds as disclosed in WO 97/38991. Also, a test was reported (ATN test) on the dopamine antagonizing properties of a number of compounds with a linear amine side chain (by preventing the symptoms elicited with the dopamine agonist apomorphine, such as, for example, agitation and stereotypy), where it was shown that the specific halogen substitution contributed positively to the dopamine antagonism. Such effect was not demonstrated nor suggested for compounds containing a cyclic amine side chain. A number of compounds with a cyclic amine side chain were disclosed which are excluded from this application by way of a disclaimer.

Both WO 03/048146, published Jun. 12, 2003 (Janssen Pharmaceutica N.V.) and WO 03/048147, published Jun. 12, 2003 (Janssen Pharmaceutica N.V.) disclose processes for the preparation of each of the four diastereomers of trans-, respectively cis-fused 3,3a,8,12b-tetrahydro-2H-dibenzo[3,4:6,7]cyclohepta[1,2-b]furan derivatives in a stereochemically pure form from a single enantiomerically pure precursor. The compounds of WO 03/048146 show affinity for 5-$HT_2$ receptors, particularly for 5-$HT_{2A}$ and 5-$HT_{2C}$ receptors. The compounds of WO 03/048147 show affinity for the serotonin 5-$HT_{2A}$, 5-$HT_{2C}$ and 5-$HT_7$ receptors, the $H_1$-receptors (p$IC_{50}$=7.15-7.89), D2 and/or D3 receptors and for the norepinephrine reuptake transporters (p$IC_{50}$=6.03-7.34). The compounds disclosed in the latter two publications do not contain a cyclic amine side chain.

WO 03/040122, published May 15, 2003 (Janssen Pharmaceutica N.V.) discloses mandelate salts of the compounds according to WO 97/38991 and WO 99/19317. Said salts were surprisingly found to be more stable at enhanced temperature and relative humidity than the compounds disclosed in WO 97/38991 and WO 99/19317.

DESCRIPTION OF THE INVENTION

It is the object of the present invention to provide novel analogues of the tetracyclic tetrahydrofuran derivatives of PCT specifications WO 97/38991 and WO 99/19317 which have an advantageous pharmacological profile, in particular $D_2$ activity, in comparison with the compounds disclosed in said PCT specifications.

This goal is achieved by the present novel compounds according to Formula (I):

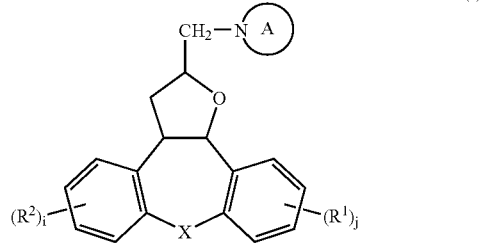

(I)

a pharmaceutically acceptable acid or base addition salt thereof, an N-oxide form thereof or a quaternary ammonium salt thereof, wherein:

i, j are integers, each selected independently from zero, 1, 2, 3 and 4;

each $R^1$ and $R^2$ is independently selected from the group of halo; cyano; hydroxy; carboxyl; nitro; amino; mono- or di(alkyl)amino; mono- or di(alkyl-carbonyl)amino; aminosulphonyl; mono- or di(alkyl)aminosulphonyl; alkyl; alkenyl; alkyloxy; alkylcarbonyl and alkyloxycarbonyl;

A represents a radical selected from Formula (a), (b), (c) and (d)

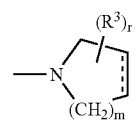

(a)

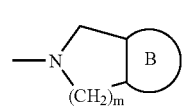

(b)

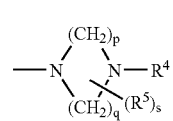

(c)

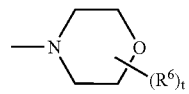

(d)

wherein:
m is an integer equal to zero, 1, 2 or 3;
n is an integer equal to 2 or 3;
p is an integer equal to 1, 2, 3 or 4;
q is an integer equal to 1 or 2;
r is an integer equal to 1, 2 or 3;
s is an integer equal to zero, 1 or 2;
t is an integer equal to 1 or 2;
the dotted line in Formula (a) represents a bond when m is 1, 2 or 3; and the dotted line is absent when m is zero;
ring B represents a fused benzene ring; or a fused five or six-membered monocyclic ring containing 1, 2 or 3 heteroatoms selected from oxygen, nitrogen and sulphur; wherein each ring B is optionally substituted with alkyl or alkyloxy;

$R^3$ is selected from the group of hydroxy; carboxyl, cyano; oxo; alkyl; alkyloxyalkyl; aryloxyalkyl; alkylcarbonyloxyalkyl; alkyloxycarbonyloxy-alkyl; mono- or di(alkyl)aminocarbonyloxyalkyl; mono- or di(aryl)amino-carbonyloxyalkyl; mono- or di(arylalkyl)aminocarbonyloxyalkyl; alkyloxy-carbonylalkyl; aryloxycarbonylalkyl; alkyloxycarbonylmethylidene; alkenyl; aryl; Het; alkyloxy; aryloxy; alkylcarbonyloxy; arylcarbonyloxy; arylalkylcarbonyloxy; Het-carbonyloxy; alkylcarbonyl; Het-carbonyl; aryl-Het-carbonyl; arylalkenyl-Het-carbonyl; alkyloxycarbonyl; aryloxy-carbonyl; mono- or di(alkyl)aminocarbonyl; mono- or di(alkyloxyalkyl)-aminocarbonyl; mono- or di(alkylthioalkyl)aminocarbonyl; mono- or di(arylalkyl)aminocarbonyl; mono- or di(Het-alkyl)aminocarbonyl; (mono- or di(alkyl)aminoalkyl)(alkyl)aminocarbonyl; (aryl)(alkyloxycarbonyl-alkyl) aminocarbonyl; mono- or di(alkenyl)aminocarbonyl; (alkyl)(alkenyl)-aminocarbonyl; mono- or di(aryl)aminocarbonyl; mono- or di(Het)amino-carbonyl; mono- or di(alkyl)amino; mono- or di(alkylcarbonyl)amino; mono- or di(alkyloxycarbonyl)amino; mono- or di(alkyloxyalkyloxycarbonyl)amino; mono- or di(aryloxyalkylcarbonyl)amino; mono- or di(arylthioalkylcarbonyl)amino; mono- or di(arylalkylcarbonyl)amino; mono- or di(Het-alkylcarbonyl)amino; mono- or di(alkynyloxycarbonyl)-amino; mono- or di(arylcarbonyl)amino; mono- or di(arylarylcarbonyl)-amino; mono- or di(Het-carbonyl)amino; mono- or di(aryl-Het-carbonyl)-amino; mono- or di(alkyloxycarbonyl)amino; mono- or di(arylalkyloxy-carbonyl)amino; mono- or di(aryloxycarbonyl)amino; mono- or di(amino-alkylaminothiocarbonyl)amino; mono- or di(alkylaminocarbonyl)amino; mono- or di(mono- or di(alkyloxyalkyl)aminothiocarbonyl)amino; mono- or di(mono- or di(arylalkyl)aminocarbonyl)amino; mono- or di(mono- or di(alkylsulphonylalkyl)aminothiocarbonyl)amino; mono- or di(mono- or di(Het-alkyl)aminothiocarbonyl)amino; mono- or di(mono- or di(alkyloxy-carbonylalkyl)aminocarbonyl)amino; mono- or di(mono- or di(aryl)amino-carbonyl)amino; mono- or di(mono- or di(aryl)aminothiocarbonyl)amino; mono- or di(mono- or di(aryloxyaryl)aminocarbonyl)amino; mono- or di(mono- or di(Het)aminothiocarbonyl)amino; and mono- or di(mono- or di(Het)aminocarbonyl)amino;

$R^4$ is selected from the group of alkyl; alkyloxyarylalkyl; arylalkyl; alkyloxy-carbonylarylalkyl; aryloxyarylalkyl; Het-alkyl; aryl-Het-alkyl; aryl-sulphonyl-Het-alkyl; arylalkyloxyalkyl; aryloxyalkyl; Het-alkyloxy-alkyl; arylcarbonyloxyalkyl; Het-carbonyloxyalkyl; alkylsulphonyloxyalkyl; alkylcarbonyloxyalkyl; arylalkyl-carbonylalkyl; arylcarbonylalkyl; Het-carbonylalkyl; alkenyl; arylalkenyl; Het-alkenyl; alkyloxyaryl; Het; alkylcarbonyl; alkyloxyalkylcarbonyl; arylalkylcarbonyl; arylcarbonyl; Het-carbonyl; arylalkyloxycarbonyl; aryloxycarbonyl; alkenyloxycarbonyl; mono- or di(alkyl)aminocarbonyl; mono- or di(alkyl)aminothiocarbonyl; mono- or di(alkyloxyalkyl)aminocarbonyl; mono- or di(alkylthioalkyl)-aminocarbonyl; mono- or di(arylalkyl)aminocarbonyl; mono- or di(aryl-alkyl)aminothiocarbonyl; mono- or di(Het-alkyl)aminocarbonyl; mono- or di(alkyloxycarbonylalkyl)aminocarbonyl; mono- or di(alkyloxycarbonyl-alkyl)aminothiocarbonyl; mono- or di(aryl)aminocarbonyl; mono- or di(aryl)aminothiocarbonyl; mono- or di(Het)aminocarbonyl; mono- or di(arylcarbonyl)aminothiocarbonyl; mono- or di(arylcarbonyl)amino-carbonyl; mono- or di(Het-carbonyl)aminocarbonyl; alkylsulphonyl; arylalkylsulphonyl; alkenylsulphonyl; and arylsulphonyl;

or, when p and q are not both 2 and/or s is not zero, $R^4$ additionally represents hydrogen, alkyl, or alkylcarbonyloxyalkyl;

$R^5$ represents alkyl;

$R^6$ is selected from the group of alkyl; alkyloxyalkyl; aryloxyalkyl; hydroxycarbonylalkyl; alkyloxycarbonylalkyl; mono- or di(alkyl)-aminocarbonylalkyl; mono- or di(alkyl)aminocarbonyloxyalkyl; mono- or di(aryl)aminocarbonylalkyl; mono- or di(alkyl)aminoalkyl and alkyl-sulphonyloxyalkyl;

X is selected from the group of $CR^7R^8$; O; S; $S(=O)$; $S(=O)_2$; and $NR^9$;

wherein:
$R^7$ and $R^8$ each independently are selected from the group of hydrogen; hydroxy; alkyl; and alkyloxy; or $R^7$ and $R^8$ taken together form the radical methylene; or a bivalent radical of Formula —$(CH_2)_2$—; —$(CH_2)_3$—; —$(CH_2)_4$—; —$(CH_2)_5$—; —O—$(CH_2)_2$—O—; or —O$(CH_2)_3$O—; or, together with the carbon atom to which they are attached, form a carbonyl radical; and $R^9$ is selected from hydrogen; alkyl; alkylcarbonyl; arylcarbonyl; arylalkyl; arylalkylcarbonyl; alkylsulphonyl; arylsulphonyl and arylalkylsulphonyl;

alkyl represents a straight or branched saturated hydrocarbon radical having from 1 to 10 carbon atoms, a cyclic saturated hydrocarbon radical having from 3 to 8 carbon atoms or a saturated hydrocarbon radical containing a straight or branched moiety having from 1 to 10 carbon atoms and a cyclic moiety having from 3 to 8 carbon atoms; each radical being optionally substituted with one or more substituents selected from the group of halo; nitro; cyano; oxo; hydroxy; formyl; carboxyl and amino radicals;

alkenyl represents a straight or branched unsaturated hydrocarbon radical having from 1 to 10 carbon atoms, a cyclic unsaturated hydrocarbon radical having from 3 to 8 carbon atoms or an unsaturated hydrocarbon radical containing a straight or branched moiety having from 1 to 10 carbon atoms and a cyclic moiety having from 3 to 8 carbon atoms; said radical having one or more double bonds and said radical being optionally substituted with one or more substituents selected from the group of halo; nitro; cyano; oxo; hydroxy; formyl; carboxyl and amino radicals;

aryl is phenyl or naphthyl, each being optionally substituted with one or more substituents selected from halo; nitro; cyano; hydroxy; alkyloxy; alkylthio; haloalkyl, alkyloxycarbonyl and alkyl radicals; or with a bivalent radical of Formula —$(CH_2)_3$—;

Het represents a saturated or unsaturated four, five or six-membered monocyclic ring containing one, two or three heteroatoms selected from oxygen, nitrogen and sulphur, optionally fused to a benzene ring or to a further ring containing one, two or three heteroatoms selected from oxygen, nitrogen and sulphur; each of said rings being optionally substituted with one or more substituents selected from cyano, alkyl, haloalkyl, alkyloxy, alkylthio, alkylcarbonyl, alkyloxycarbonyl and mono- or di-alkylaminocarbonylalkyl radicals; and halo represents fluoro; chloro; bromo or iodo;

with the provision that the following compounds are excluded:

4-phenyl-1-(3,3a,8,12b-tetrahydro-2H-1-oxa-dibenzo[e,h]azulen-2-ylmethyl)-piperidine;
4-phenyl-1-(11-fluoro-3,3a, 8,12b-tetrahydro-2H-1-oxa-dibenzo[e,h]azulen-2-yl-methyl)-piperidine;
4-phenyl-1-(5-fluoro-3,3a, 8,12b-tetrahydro-2H-1-oxa-dibenzo[e,h]azulen-2-yl-methyl)-piperidine;
(4-fluorophenyl)-[1-(3,3a,8,12b-tetrahydro-2H-1-oxa-dibenzo[e,h]azulen-2-yl-methyl)-piperidin-4-yl]-methanone;
(4-fluorophenyl)-[1-(11-fluoro-3,3a,8,12b-tetrahydro-2H-1-oxa-dibenzo[e,h]azulen-2-ylmethyl)-piperidin-4-yl]-methanone;
(4-fluorophenyl)-[1-(5-fluoro-3,3a, 8,12b-tetrahydro-2H-1-oxa-dibenzo[e,h]azulen-2-ylmethyl)-piperidin-4-yl]-methanone;
1-methyl-4-(3,3a, 8,12b-tetrahydro-2H-1-oxa-dibenzo[e,h]azulen-2-ylmethyl)-piperazine;
1-methyl-4-(11-fluoro-3,3a, 8,12b-tetrahydro-2H-1-oxa-dibenzo[e,h]azulen-2-yl-methyl)-piperazine;
1-methyl-4-(5,11-difluoro-3,3a,8,12b-tetrahydro-2H-1-oxa-dibenzo[e,h]azulen-2-ylmethyl)-piperazine;
2-[4-(3,3a, 8,12b-tetrahydro-2H-1-oxa-dibenzo[e,h]azulen-2-ylmethyl)-piperazin-1-yl]-ethanol;
2-[4-(5,11-difluoro-3,3a,8,12b-tetrahydro-2H-1-oxa-dibenzo[e,h]azulen-2-yl-methyl)-piperazin-1-yl]-ethanol
2-[4-(11-fluoro-3,3a, 8,12b-tetrahydro-2H-1-oxa-dibenzo[e,h]azulen-2-ylmethyl-piperazin-1-yl]-ethanol;
4-phenyl-1-(2,3,3a, 12b-tetrahydro-1-oxa-8-thia-dibenzo[e,h]azulen-2-ylmethyl)-piperidine; and
1-methyl-4-(2,3,3a, 12b-tetrahydro-1-oxa-8-thia-dibenzo[e,h]azulen-2-ylmethyl)-piperazine.

It is understood that in the following, the abovementioned compounds are excluded from the invention, in particular from the scope related to compounds, pharmaceutical compositions, processes and uses.

The compounds according to the invention are structurally characterized by the presence of a substituted cyclic amine side chain in the 2-position. It has been found that the presence of this side chain provides compounds which have a potent affinity for the $D_2$ receptor, an activity not attributed to the compounds in the above-mentioned PCT specifications WO 97/38991 and WO 99/19317, which renders the compounds according to the invention especially suitable for use in the treatment of psychoses such as mania, excitement, aggression, and the positive symptoms of schizophrenia. In contrast, the compounds according to the invention do not show any significant inhibitory activity against norepinephrine transporter reuptake (NET), which indicates that they do not have a useful antidepressant activity. The absence of such antidepressant activity may be advantageous when selecting a compound for a certain therapeutic profile, particularly since the compounds further have affinity towards the $5\text{-}HT_{2A}$ and $5\text{-}HT_{2C}$ receptors. Such a profile of activity for the compounds according to the invention is not taught or suggested in the above PCT specifications.

The skilled person can easily make a selection of compounds based on such pharmacological profile. Any selection of compounds is embraced within this invention.

For example, the invention relates to a compound according to the invention of general Formula (I), a pharmaceutically acceptable acid or base addition salt thereof, an N-oxide form thereof or a quaternary ammonium salt thereof, wherein:

i, j are integers, each selected independently from zero and 1;

each $R^1$ and $R^2$
is independently selected from the group of halo; cyano and alkyloxy;

A represents a radical selected from Formula (a), (b), (c) and (d)

wherein:
m is an integer equal to zero, 1 or 2;
n is an integer equal to 2;
p is an integer equal to 2 or 3;
q is an integer equal to 2;
r is an integer equal to 1 or 2;
s is an integer equal to zero or 2;
t is an integer equal to 1;
ring B represents a fused benzene ring; or a fused five-membered monocyclic ring containing 1 oxygen heteroatom; wherein each ring B is optionally substituted with alkyl or alkyloxy;

$R^3$ is selected from the group of hydroxy; carboxyl, cyano; oxo; alkyl; alkyloxyalkyl; aryloxyalkyl; alkyloxycarbonyloxyalkyl; mono- or di(alkyl)aminocarbonyloxyalkyl; mono- or di(aryl)aminocarbonyloxyalkyl; mono- or di(arylalkyl)aminocarbonyloxyalkyl; alkyloxycarbonylalkyl; alkyloxycarbonylmethylidene; alkenyl; aryl; Het; alkyloxy; aryloxy; alkylcarbonyloxy; arylcarbonyloxy; arylalkylcarbonyloxy; alkylcarbonyl; Het-carbonyl; aryl-Het-carbonyl; arylalkenyl-Het-carbonyl; alkyloxy-carbonyl; mono- or di(alkyl)aminocarbonyl; mono- or di(alkylthioalkyl)-aminocarbonyl; mono- or di(arylalkyl)aminocarbonyl; mono- or di(Het-alkyl)aminocarbonyl; (mono- or di(alkyl)aminoalkyl)(alkyl)aminocarbonyl; (aryl)(alkyloxycarbonylalkyl)aminocarbonyl; mono- or di(alkenyl)amino-carbonyl; (alkyl)(alkenyl)aminocarbonyl; mono- or di(aryl)aminocarbonyl; mono- or di(Het)aminocarbonyl; mono- or di(alkylcarbonyl)amino; mono- or di(alkyloxycarbonyl)amino; mono- or di(alkyloxyalkyloxycarbonyl)-amino; mono- or di(arylthioalkylcarbonyl)amino; mono- or di(arylalkyl-carbonyl)amino; mono- or di(Het-alkylcarbonyl)amino; mono- or di(alkynyloxycarbonyl)amino; mono- or di(arylcarbonyl)amino; mono- or di(arylarylcarbonyl)amino; mono- or di(Het-carbonyl)amino; mono- or di(aryl-Het-carbonyl)amino; mono- or di(alkyloxycarbonyl)amino; mono- or di(arylalkyloxycarbonyl)amino; mono- or di(aryloxycarbonyl)amino; mono- or di(aminoalkylaminothiocarbonyl)amino; mono- or di(alkylamino-carbonyl)amino; mono- or di(mono- or di(alkyloxyalkyl)aminothio-carbonyl)amino; mono- or di(mono- or di(arylalkyl)aminocarbonyl)amino; mono- or di(mono- or di(alkylsulphonylalkyl)aminothiocarbonyl)amino; mono- or di(mono- or di(Het-alkyl)aminothiocarbonyl)amino; mono- or di(mono- or di(alkyloxycarbonylalkyl)aminocarbonyl) amino; mono- or di(mono- or di(aryl)aminocarbonyl) amino; mono- or di(mono- or di(aryl)aminothiocarbonyl)amino; mono- or di(mono- or di(aryloxyaryl)-aminocarbonyl)amino; mono- or di(mono- or di(Het)aminothiocarbonyl)-amino; and mono- or di(mono- or di(Het)aminocarbonyl)amino;

$R^4$ is selected from the group of alkyl; alkyloxyarylalkyl; arylalkyl; alkyloxy-carbonylarylalkyl; aryloxyarylalkyl; Het-alkyl; aryl-Het-alkyl; aryl-sulphonyl-Het-alkyl; aryloxyalkyl; Het-alkyloxyalkyl; alkylsulphonyloxy-alkyl; arylcarbonylalkyl; arylalkenyl; alkyloxyaryl; Het; alkylcarbonyl; alkyloxyalkylcarbonyl; arylcarbonyl; Het-carbonyl; arylalkyloxycarbonyl; aryloxycarbonyl; alkenyloxycarbonyl; mono- or di(alkyl)aminocarbonyl; mono- or di(alkyl)aminothiocarbonyl; mono- or di(alkyloxyalkyl)amino-carbonyl; mono- or di(alkylthioalkyl)aminocarbonyl; mono- or di(aryl-alkyl)aminocarbonyl; mono- or di(arylalkyl)aminothiocarbonyl; mono- or di(Het-alkyl)aminocarbonyl; mono- or di(alkyloxycarbonylalkyl)amino-carbonyl; mono- or di(alkyloxycarbonylalkyl)aminothiocarbonyl; mono- or di(aryl)aminocarbonyl; mono- or di(aryl)aminothiocarbonyl; mono- or di(arylcarbonyl)aminothiocarbonyl; alkylsulphonyl; arylalkylsulphonyl; alkenylsulphonyl; and arylsulphonyl;

or, when p and q are not both 2 and/or s is not zero, $R^4$ additionally represents hydrogen, alkyl, or alkylcarbonyloxyalkyl;

$R^5$ represents alkyl;

$R^6$ is selected from the group of alkyl; alkyloxyalkyl; aryloxyalkyl; hydroxycarbonylalkyl; alkyloxycarbonylalkyl; mono- or di(alkyl)-aminocarbonylalkyl; mono- or di(alkyl)aminocarbonyloxyalkyl; mono- or di(aryl)aminocarbonylalkyl; mono- or di(alkyl)aminoalkyl and alkyl-sulphonyloxyalkyl;

X is selected from the group of $CR^7R^8$; O; S and $NR^9$; wherein:
$R^7$ and $R^8$ each independently are selected from the group of hydrogen and alkyl; and
$R^9$ is alkyl;

More in particular, the invention relates to a compound according to the invention of general Formula (I), a pharmaceutically acceptable acid or base addition salt thereof, an N-oxide form thereof or a quaternary ammonium salt thereof, wherein:
i is zero
j is 1;
$R^1$ is halo;
A represents a radical of Formula (a) wherein:
(i) m is 1;
r is 1; and
$R^3$ is hydroxy, oxo or alkyloxycarbonyl; or
(ii) m is 2;
r is 1; and
$R^3$ is selected from the group of hydroxy; alkyl; alkyloxyalkyl; a alkyloxycarbonyl; alkyloxycarbonylalkyl; and alkylenedioxy; or
A represents a radical of Formula (b) wherein:
n is 2; and
ring A represents a fused benzene ring or a fused five-membered ring containing an oxygen heteroatom; said ring being optionally substituted with alkyl or alkyloxy; or
A represents a radical of Formula (c) wherein:
p and q are each equal to 2; and
$R^4$ is selected from the group of Het-alkyl; alkylcarbonyl; arylcarbonyl; and alkylaminocarbonyl; or
A represents a radical of Formula (d) wherein
t is 1; and
$R^6$ is alkyl, optionally substituted with hydroxyl; and
X is —$CH_2$— or —O—.

More in particular, the invention relates to a compound according to the general Formula (I), a pharmaceutically acceptable acid or base addition salt thereof, an N-oxide form thereof or a quaternary ammonium salt thereof, wherein:
i is zero
j is 1;
$R^1$ is fluoro;
A represents a radical of Formula (a) wherein:
(i) m is 1;
r is 1; and
$R^3$ is 3-hydroxy, 3-oxo or 3-alkyloxycarbonyl; or
(ii) m is 2;
r is I or 2; and
$R^3$ is 3- or 4-hydroxy; 3- or 4-$C_{1-3}$alkyl substituted with hydroxy; or 3- or 4-alkyloxyalkyl; 3- or 4-alkyloxycarbonyl; 3- or 4-alkyloxycarbonylalkyl; or 4,4-(hydroxy)(alkyloxyalkyl); or 4,4-ethylenedioxy; or
A represents a radical of Formula (b) wherein:
n is 2; and
ring A represents a fused benzene ring or a fused five-membered ring containing an oxygen heteroatom; said ring being substituted with hydroxyalkyl or alkyloxy; or
A represents a radical of Formula (c) wherein:
p and q are each 2; and
$R^4$ is furylalkyl; cyclopropylcarbonyl; phenylcarbonyl; or cyclopropylaminocarbonyl; or
A represents a radical of Formula (d) wherein:
t is 1; and
$R^6$ is alkyl substituted with hydroxyl; and
X is —$CH_2$— or —O—.

In particular, the following compounds are preferred:

1-(11-fluoro-3,3a, 8,12b-tetrahydro-2H-1-oxa-dibenzo[e,h]azulen-2-ylmethyl)-pyrrolidin-3-one;

1-(11-fluoro-3,3a, 8,12b-tetrahydro-2H-1-oxa-dibenzo[e,h]azulen-2-ylmethyl)-pyrrolidine-3-carboxylic acid methyl ester;

1-(11-fluoro-3,3a,8,12b-tetrahydro-2H-1-oxa-dibenzo[e,h]azulen-2-ylmethyl)-4-furan-3-ylmethyl-piperazine;

cyclopropyl-[4-(11-fluoro-3,3a,8,12b-tetrahydro-2H-1-oxa-dibenzo[e,h]azulen-2-ylmethyl)-piperazin-1-yl]-methanone;

[4-(11-fluoro-3,3a, 8,12b-tetrahydro-2H-1-oxa-dibenzo[e,h]azulen-2-ylmethyl)-piperazin-1-yl]-phenyl-methanone;

4-(11-fluoro-3,3a, 8,12b-tetrahydro-2H-1-oxa-dibenzo[e,h]azulen-2-ylmethyl)-piperazine-1-carboxylic acid cyclopropylamide;

[4-(11-fluoro-3,3a, 8,12b-tetrahydro-2H-1-oxa-dibenzo[e,h]azulen-2-ylmethyl)-morpholin-2-yl]-methanol;

1-(11-fluoro-3,3a,8,12b-tetrahydro-2H-1-oxa-dibenzo[e,h]azulen-2-ylmethyl)-piperidin-3-ol;

[1-(11-fluoro-3,3a, 8,12b-tetrahydro-2H-1-oxa-dibenzo[e,h]azulen-2-ylmethyl)-piperidin-3-yl]-methanol;

[1-(11-fluoro-3,3a, 8,12b-tetrahydro-2H-1-oxa-dibenzo[e,h]azulen-2-ylmethyl)-piperidin-4-yl]-methanol;

3-[1-(11-fluoro-3,3a, 8,12b-tetrahydro-2H-1-oxa-dibenzo[e,h]azulen-2-ylmethyl)-piperidin-4-yl]-propan-1-ol;

1-(11-fluoro-3,3a, 8,12b-tetrahydro-2H-1-oxa-dibenzo[e,h]azulen-2-ylmethyl)-piperidine-4-carboxylic acid ethyl ester;

[1-(11-fluoro-3,3a, 8,12b-tetrahydro-2H-1-oxa-dibenzo[e,h]azulen-2-ylmethyl)-piperidin-4-yl]-acetic acid ethyl ester;

[5-(11-fluoro-3,3a, 8,12b-tetrahydro-2H-1-oxa-dibenzo[e,h]azulen-2-ylmethyl)-octahydro-furo[3,2-c]pyridin-2-yl]-methanol;

1-(11-fluoro-3,3a,8,12b-tetrahydro-2H-1-oxa-dibenzo[e,h] azulen-2-ylmethyl)-pyrrolidin-3-ol;

1-(11-fluoro-3,3a,8,12b-tetrahydro-2H-1-oxa-dibenzo[e,h] azulen-2-ylmethyl)-piperidin-4-ol;

2-[1-(11-fluoro-3,3a, 8,12b-tetrahydro-2H-1-oxa-dibenzo[e, h]azulen-2-ylmethyl)-piperidin-4-yl]-ethanol;

1-(11-fluoro-3,3a,8,12b-tetrahydro-2H-1-oxa-dibenzo[e,h] azulen-2-ylmethyl)-4-methoxymethyl-piperidin-4-ol;

2-(11-fluoro-3,3a,8,12b-tetrahydro-2H-1-oxa-dibenzo[e,h] azulen-2-ylmethyl)-6,7-dimethoxy-1,2,3,4-tetrahydro-isoquinoline; and 8-(11-fluoro-3,3a,8,12b-tetrahydro-2H-1-oxa-dibenzo[e,h] azulen-2-ylmethyl)-1,4-dioxa-8-aza-spiro[4.5]decane.

More in particular, the invention concerns the [2R-(2α, 3aα, 12bβ)]-isomer of the compounds according to the invention, in particular of the above mentioned compounds.

More in particular, the invention relates to an oxalate salt, in particular the (1:1) oxalate salt, and a trifluoroacetate salt, in particular the (1:1) trifluoroacetate salt of the compounds according to the invention, in particular of the above mentioned compounds.

Particularly preferred compounds according to the invention include the following compounds:

[2R-(2α, 3aα, 12bβ)]1-(11-fluoro-3,3a,8,12b-tetrahydro-2H-1-oxa-dibenzo[e,h]-azulen-2-ylmethyl)-pyrrolidin-3-one (compound 7);

[2R-(2α, 3aα, 12bβ)]-(3'RS) 1-(11-fluoro-3,3a,8,12b-tetrahydro-2H-1-oxa-dibenzo[e,h]azulen-2-ylmethyl)-pyrrolidine-3-carboxylic acid methyl ester.oxalate (1:1) (compound 11);

[2R-(2α, 3aα, 12bβ)]1-(11-fluoro-3,3a,8,12b-tetrahydro-2H-1-oxa-dibenzo[e,h]-azulen-2-ylmethyl)-4-furan-3-yl-methyl-piperazine.trifluoroacetate (1:1) (compound 61);

[2R-(2α, 3aα, 12bβ)]cyclopropyl-[4-(11-fluoro-3,3a, 8,12b-tetrahydro-2H-1-oxa-dibenzo[e,h]azulen-2-ylmethyl)-piperazin-1-yl]-methanone.oxalate (1:1) (compound 78);

[2R-(2α, 3aα, 12bβ)][4-(11-fluoro-3,3a,8,12b-tetrahydro-2H-1-oxa-dibenzo[e,h]azulen-2-ylmethyl)-piperazin-1-yl]-phenyl-methanone.oxalate (1:1) (compound 82)

[2R-(2α, 3aα, 12bβ)]4-(11-fluoro-3,3a,8,12b-tetrahydro-2H-1-oxa-dibenzo[e,h]azulen-2-ylmethyl)-piperazine-1-carboxylic acid cyclopropylamide.oxalate (1:1) (compound 94);

[2R-(2aα, 3aα, 12bβ)]-(3'RS)-[4-(11-fluoro-3,3a,8,12b-tetrahydro-2H-1-oxa-dibenzo[e,h]azulen-2-ylmethyl)-morpholin-2-yl]-methanol.oxalate (1:1) (compound 128);

[2R-(2α, 3aα, 12bβ)]-(3'RS)-1-(11-fluoro-3,3a,8,12b-tetrahydro-2H-1-oxa-dibenzo[e,h]azulen-2-ylmethyl)-piperidin-3-ol (compound 140);

[2R-(2α, 3aα, 12bβ)]-(3'RS)-[1-(11-fluoro-3,3a,8,12b-tetrahydro-2H-1-oxa-dibenzo[e,h]azulen-2-ylmethyl)-piperidin-3-yl]-methanol.oxalate (1:1) (compound 147);

[2R-(2α, 3aα, 12bβ)][1-(11-fluoro-3,3a,8,12b-tetrahydro-2H-1-oxa-dibenzo[e,h]azulen-2-ylmethyl)-piperidin-4-yl]-methanol (compound 150);

[2R-(2α, 3aα, 12bβ)]3-[1-(11-fluoro-3,3a,8,12b-tetrahydro-2H-1-oxa-dibenzo[e,h]azulen-2-ylmethyl)-piperidin-4-yl]-propan-1-ol.oxalate (1:1) (compound 155);

[2R-(2α, 3aα, 12bβ)]1-(11-fluoro-3,3a,8,12b-tetrahydro-2H-1-oxa-dibenzo[e,h]azulen-2-ylmethyl)-piperidine-4-carboxylic acid ethyl ester (compound 161);

[2R-(2α, 3aα, 12bβ)][1-(11-fluoro-3,3a,8,12b-tetrahydro-2H-1-oxa-dibenzo[e,h]azulen-2-ylmethyl)-piperidin-4-yl]-acetic acid ethyl ester.oxalate (1:1) (compound 164); and

[2R-(2α, 3aα, 12bβ)]-(2'RS,3a'RS, 7a'RS)[5-(11-fluoro-3, 3a,8,12b-tetrahydro-2H-1-oxa-dibenzo[e,h]azulen-2-ylmethyl)-octahydro-furo[3,2-c]pyridin-2-yl]-methanol.oxalate (1:1) (compound 274).

Most particularly preferred compounds according to the invention include the following compounds:

[2R-(2α, 3aα, 12bβ)]-(3'RS) 1-(11-fluoro-3,3a,8,12b-tetrahydro-2H-1-oxa-dibenzo[e,h]azulen-2-ylmethyl)-pyrrolidin-3-ol.oxalate (1:1) (compound 1);

[2R-(2α, 3aα, 12bβ)]1-(11-fluoro-3,3a,8,12b-tetrahydro-2H-1-oxa-dibenzo[e,h]azulen-2-ylmethyl)-piperidin-4-ol.oxalate (1:1) (compound 144);

[2R-(2α, 3aα, 12bβ)]2-[1-(11-fluoro-3,3a,8,12b-tetrahydro-2H-1-oxa-dibenzo[e,h]-azulen-2-ylmethyl)-piperidin-4-yl]-ethanol (compound 153);

[2R-(2α, 3aα, 12bβ)]2-(11-fluoro-3,3a,8,12b-tetrahydro-2H-1-oxa-dibenzo[e,h]azulen-2-ylmethyl)-6,7-dimethoxy-1,2,3,4-tetrahydro-isoquinoline.trifluoroacetate (1:1) (compound 272);

[2R-(2α, 3aα, 12bβ)]1-(11-fluoro-3,3a,8,12b-tetrahydro-2H-1-oxa-dibenzo[e,h]azulen-2-ylmethyl)-4-methoxymethyl-piperidin-4-ol.trifluoroacetate (1:1) (compound 276); and

[2R-(2α, 3aα, 12bβ)]8-(11-fluoro-3,3a,8,12b-tetrahydro-2H-1-oxa-dibenzo[e,h]azulen-2-ylmethyl)-1,4-dioxa-8-aza-spiro[4.5]decane (compound 277).

DETAILED DESCRIPTION OF THE INVENTION

In the framework of this application, alkyl includes for example methyl, ethyl, propyl, butyl, 1-methylpropyl, 1,1-dimethylethyl, pentyl, hexyl; cyclopropyl, methylcyclopropyl, cyclobutyl, cyclopentyl and cyclohexyl.

In the framework of this application, with "compound according to the invention" is meant a compound according to the general Formula (I), a pharmaceutically acceptable acid or base addition salt thereof, an N-oxide form thereof or a quaternary ammonium salt thereof.

The pharmaceutically acceptable acid addition salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid.

Conversely, said acid addition salts forms can be converted into the free forms by treatment with an appropriate base.

The compound according to Formula (I) containing an acidic proton may also be converted into a therapeutically active non-toxic metal or amine addition salt form (base addition salt) by treatment with an appropriate organic and inorganic base. Appropriate base salt forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salt form can be converted into the free form by treatment with an appropriate acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g. particularly those tertiary nitrogens bearing the $R^1$ and $R^2$ substituents) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds according to the invention possess at least one oxidizable nitrogen (tertiary amine moiety). It is therefore highly likely that N-oxides are formed in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A quaternary ammonium salt of compound according to Formula (I) defines said compound which is able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has at least one positively charged nitrogen. Pharmaceutically acceptable counterions include chloro, bromo, iodo, trifluoroacetate and acetate ions.

The invention also inherently comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473. Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the Formula —COOR$^x$, where R$^x$ is a $C_{1-6}$alkyl, phenyl, benzyl or one of the following groups:

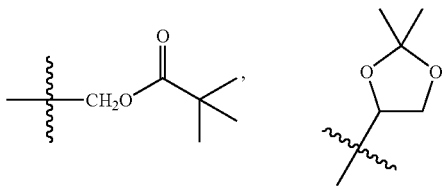

Amidated groups include groups of the Formula —CONR$^y$R$^z$, wherein R$^y$ is H, $C_{1-6}$alkyl, phenyl or benzyl and R$^z$ is —OH, H, $C_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

In the framework of this application, a compound according to the invention is inherently intended to comprise all stereochemically isomeric forms thereof. The term "stereochemically isomeric form" as used herein defines all the possible stereochemically isomeric forms that a compound of Formula (I) may possess. Unless otherwise mentioned or indicated, the chemical designation of a compound denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Hence, all stereochemically isomeric forms of a compound of Formula (I) are intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in a compound according to Formula (I)) relative to the position of the highest priority substituent on the reference atom is denominated "α", if it is on the same side of the mean plane determined by the ring system, or "β", if it is on the other side of the mean plane determined by the ring system.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluor is mentioned, it is understood to refer to $^{18}F$, $^{19}F$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), a pharmaceutically acceptable acid or base addition salt thereof, an N-oxide form thereof, or a quaternary ammonium salt thereof, which contains at least one radioactive atom. For example, a compound can be labelled with positron or with gamma emitting radioactive isotopes. For radioligand-binding techniques (membrane receptor assay), the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

The numbering of the tetracyclic ring-system present in the compounds of Formula (I), as defined by Chemical Abstracts nomenclature is shown in the Formula below.

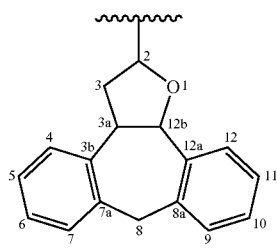 [SMILES: *C1CC2c3ccccc3Cc3ccccc3C2O1]

The compounds of Formula (I) have at least three stereogenic centers in their chemical structure, namely carbon atom 2, 3a and 12b. Said asymmetric center and any other asymmetric center which may be present, are indicated by the descriptors R and S.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

The compounds of the present invention show affinity for 5-HT$_2$ receptors, particularly for 5-HT$_{2A}$ and 5-HT$_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden) and affinity for the D$_2$ receptor. The serotonin antagonistic properties of the present compounds may be demonstrated by their inhibitory effect in the "5-hydroxytryptophan Test on Rats" which is described in Drug Dev. Res., 13, 237-244 (1988).

The compounds of the present invention also have favourable physicochemical properties. For instance, they are chemically stable compounds.

In view of their capability to block the 5-HT$_2$ receptors, and in particular to block 5-HT$_{2A}$ and 5-HT$_{2C}$ receptors, as well as the D$_2$ receptor the compounds according to the invention are useful as a medicine, in particular in the prophylactic and therapeutic treatment of conditions mediated through either of these receptors.

The invention therefore relates to a compound according to the general Formula (I), a pharmaceutically acceptable acid or base addition salt thereof, an N-oxide form thereof or a quaternary ammonium salt thereof, for use as a medicine.

The invention also relates to the use of a compound according to the general Formula (I), a pharmaceutically acceptable acid or base addition salt thereof, an N-oxide form thereof or a quaternary ammonium salt thereof, for the manufacture of a medicament for treating, either prophylactic or therapeutic or both, conditions mediated through the 5-HT$_2$ receptors.

The invention also relates to the use of a compound according to the general Formula (I), a pharmaceutically acceptable acid or base addition salt thereof, an N-oxide form thereof or a quaternary ammonium salt thereof, for the manufacture of a medicament for treating, either prophylactic or therapeutic or both, conditions mediated through the D$_2$ receptors.

The invention also relates to the use of a compound according to the general Formula (I), a pharmaceutically acceptable acid or base addition salt thereof, an N-oxide form thereof or a quaternary ammonium salt thereof, for the manufacture of a medicament for treating, either prophylactic or therapeutic or both, conditions mediated through the 5-HT$_2$, and/or D$_2$ receptors.

In view of these pharmacological and physicochemical properties, the compounds of Formula (I) are useful as therapeutic agents in the treatment or the prevention of central nervous system disorders like anxiety, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children such as ADHD, aggression, memory disorders and attitude disorders in older people, addiction, obesity, bulimia and similar disorders. In particular, the present compounds may be used as anxiolytics, antipsychotics, anti-schizophrenia agents, anti-migraine agents and as agents having the potential to overrule the addictive properties of drugs of abuse.

The compounds of Formula (I) may also be used as therapeutic agents in the treatment of motor disorders. It may be advantageous to use the present compounds in combination with classical therapeutic agents for such disorders.

The compounds of Formula (I) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of Formula (I), it follows that the present invention also provides a method of treating warm-blooded animals suffering from such diseases, said method comprising the systemic administration of a therapeutic amount of a compound of Formula (I) effective in treating the above described disorders, in particular, in treating anxiety, psychosis, migraine and addictive properties of drugs of abuse.

The present invention thus also relates to compounds of Formula (I) as defined hereinabove for use as a medicine, in particular, the compounds of Formula (I) may be used for the manufacture of a medicament for treating anxiety, psychosis, migraine and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to the invention, in particular a compound according to Formula (I), a pharmaceutically acceptable acid or base addition salt thereof, an N-oxide form thereof or a quaternary ammonium salt thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, an N-oxide form thereof or a quaternary ammonium salt thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also cosolvents such as alcohols may improve the solubility and/or the stability of the compounds according to the invention in pharmaceutical compositions.

Preparation

The compounds of Formula (I) can generally be prepared by N-alkylating an intermediate compound of Formula (II) with an intermediate compound of Formula (III) wherein W is a suitable leaving group such as halo for example bromo, or an organosulfonyl group such as p-toluenesulfonyl.

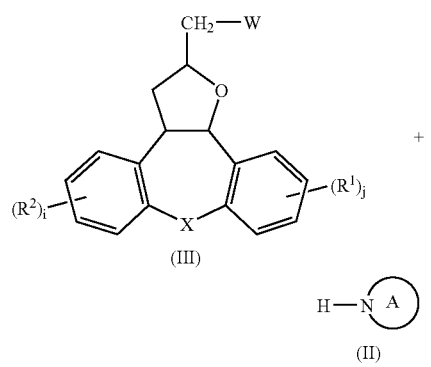

In the intermediate compounds (II) and (III), i j, $R^1$, $R^2$, X and the cyclic moiety A are as defined in the compounds of Formula (I). Said N-alkylation can conveniently be carried out in a reaction-inert solvent such as, for example, methanol, ethanol, tetrahydrofuran, methylisobutyl ketone, N,N-dimethylformamide, dimethylsulfoxide or acetonitrile and optionally in the presence of a suitable base such as calcium oxide. Stirring and elevated temperatures, for instance reflux temperature, may enhance the rate of the reaction.

Alternatively, said N-alkylation may also be performed using the procedure described by Monkovic et al. (*J. Med. Chem.* (1973), 16(4), p. 403-407) which involves the use of a pressurised reaction vessel.

Alternative processes for the preparation of compounds of Formula (I) include those described below.

The compounds of Formula (I) in which A is a radical of Formula (a) in which $R^3$ is Het-carbonyl; aryl-Het-carbonyl; arylalkenyl-Het-carbonyl in which the Het-moiety is bonded to the carbonyl via a ring nitrogen heteroatom; or $R^3$ is mono- or di(alkyl)aminocarbonyl; mono- or di(alkylthioalkyl)aminocarbonyl; mono- or di(aryl-alkyl)aminocarbonyl; mono- or di(Het-alkyl)aminocarbonyl; mono- or di(mono- or di-(alkyl)aminoalkyl)aminocarbonyl; (aryl)(alkyloxycarbonylalkyl)aminocarbonyl; (alkyl)(alkenyl)aminocarbonyl; or mono- or di(aryl)aminocarbonyl; represented by Formula (Ib) in which —NR$^a$R$^b$ is N-Het-; N-aryl-Het-; N-arylalkenyl-Het-; or mono- or di(alkyl)amino; mono- or di(alkylthioalkyl)amino; mono- or di(arylalkyl)amino; mono- or di(Het-alkyl)amino; mono- or di(mono- or di(alkyl)aminoalkyl)amino; aryl-(alkyloxycarbonyl)alkylamino; (alkyl)(alkenyl)aminocarbonyl; or mono- or di(aryl)amino, may be prepared by reacting a compound of Formula (IV) in which L is a leaving group such as halo e.g. chloro, with a compound of Formula (V), in a suitable solvent such as dichloromethane, together with for example polymer-supported trisamine, MP-carbonate, polymer-supported isocyanate, and polymer-supported DIEA with Me$_2$NCHO.

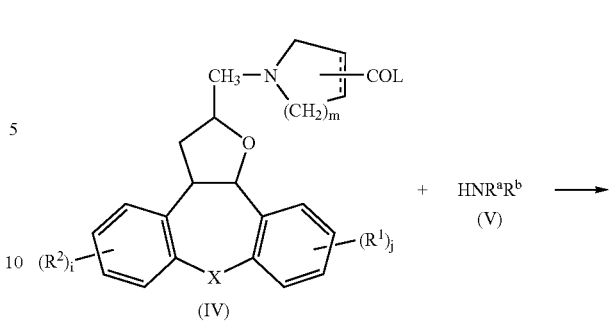

The compounds of Formula (I) in which A is a radical of Formula (c) in which $R^4$ is hydroxyalkyl, alkyloxycarbonylalkyl, arylsulphonyl or Het, represented by Formula (Ic) in which $R^c$ is hydroxyalkyl, alkyloxycarbonylalkyl, arylsulphonyl or Het, may be prepared by reacting a compound of Formula (VI) with a compound of Formula (VII) in which $L^1$ is a leaving group such as halo, e.g. chloro, in a suitable solvent such as dimethylformamide, dichloromethane, acetonitrile or dimethylsulphoxide, if desired in the presence of a base such sodium hydride or potassium carbonate.

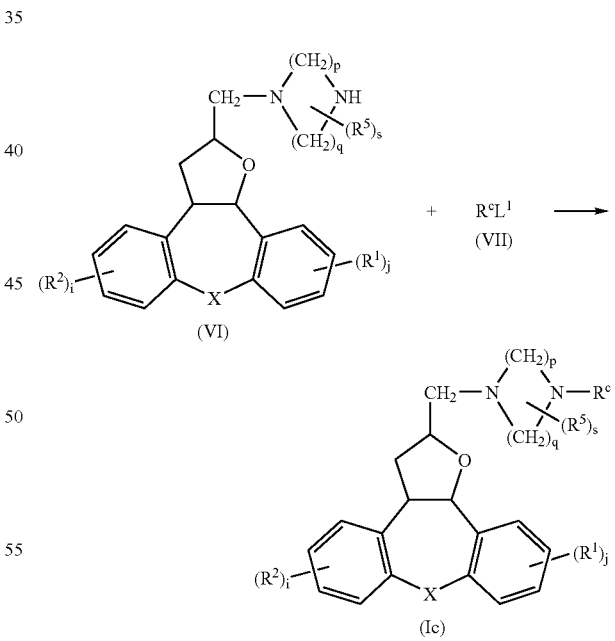

The compounds of Formula (I) in which A is a radical of Formula (c) in which $R^4$ is alkenyloxycarbonyl, aryloxycarbonyl or arylalkyloxycarbonyl, represented by Formula (Id) in which $R^d$ is alkenyl, aryl or arylalkyl, may be prepared by reacting a compound of Formula (VI) with a compound of Formula (VIII) in which $L^2$ is a leaving group such as halo, e.g. chloro, in a suitable solvent such as dichloromethane, in the presence of a base such as sodium hydride.

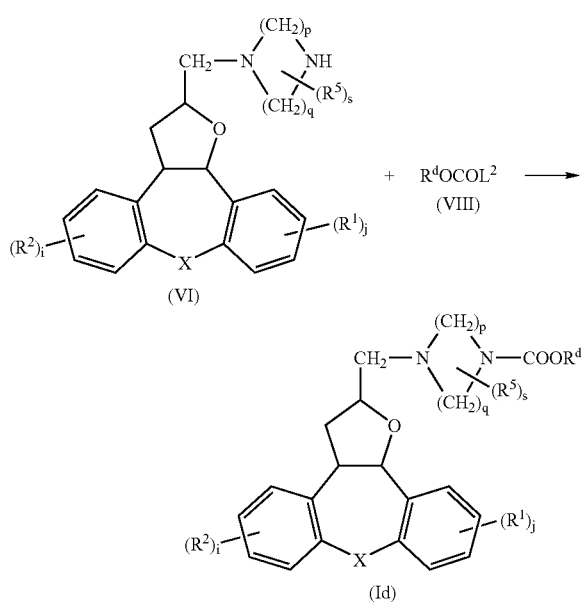

The compounds of Formula (I) in which A is a radical of Formula (c) in which $R^4$ is alkyl, arylalkenyl, Het-alkyl, aryl-Het-alkyl, alkyloxyarylalkyl, arylalkyl, aryloxyarylalkyl, alkyloxyarylalkyl, or arylsulphonyl-Het-alkyl, represented by Formula (Ie) in which $R^e$ is alkyl, arylalkenyl, Het-alkyl, aryl-Het-alkyl, alkyloxyaryl-alkyl, arylalkyl, aryloxyarylalkyl, alkyloxyarylalkyl, or arylsulphonyl-Het-alkyl ($CH_2R^e$ forming the final $R^4$ group), may be prepared by reacting a compound of Formula (VI) with a compound of Formula (IX) for example in the presence of polymer supported sodium cyanoborohydride (PS-CNBH$_4$Na) and polymer supported sulphonic acid (PS-SO$_3$H) in tetrahydofuran/acetic acid and dichloromethane with TFA.

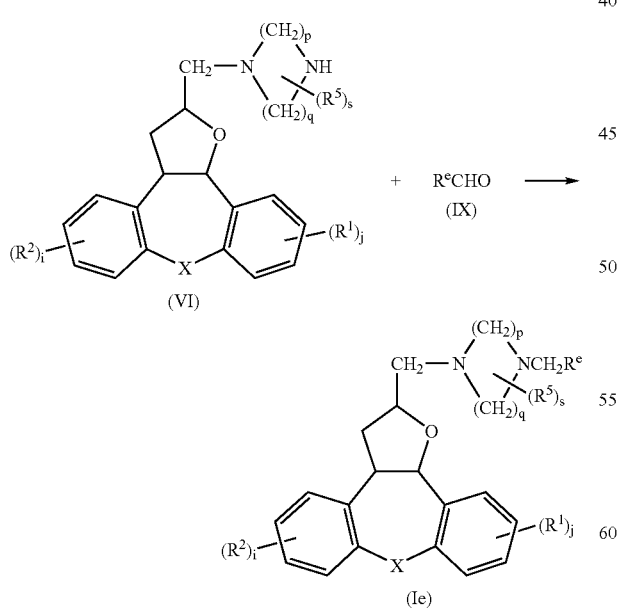

The compounds of Formula (I) in which A is a radical of Formula (c) in which $R^4$ is mono- or di(alkyl)aminocarbonyl, mono- or di(arylalkyl)aminocarbonyl, mono- or di(alkylthio-alkyl)aminocarbonyl, mono- or di(Het-alkyl)aminocarbonyl or mono- or di(alkyloxyalkyl)aminocarbonyl, represented by Formula (If) in which $R^f$ is alkyl, arylalkyl, alkylthioalkyl, Het-alkyl or alkyloxyalkyl, may be prepared by reacting a compound of Formula (VI) with a compound of Formula (X) in the presence of a base such as triethylamine and in a suitable solvent such as dichloromethane or acetonitrile:

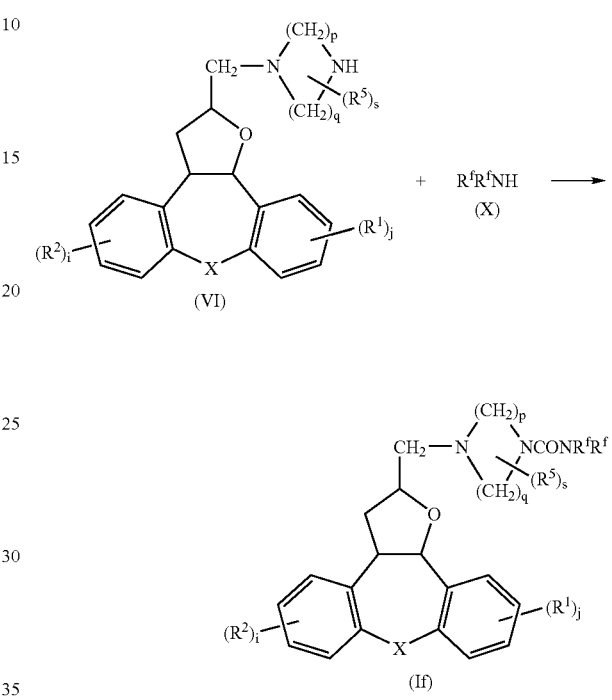

The compounds of Formula (I) in which A is a radical of Formula (a) in which r is 1 and $R^3$ is alkyloxycarbonylamino, alkynyloxycarbonylamino, alkyloxyalkyloxy-carbonylamino, aryloxycarbonylamino, mono- or dialkylaminocarbonylamino, Het-carbonylamino, arylcarbonylamino, arylalkylcarbonylamino, aryl-Het-carbonylamino, alkylcarbonylamino, arylarylcarbonylamino, Het-alkylcarbonylamino, arylthioalkylcarbonylamino or arylalkyloxycarbonylamino, represented by Formula (Ig) in which $R^g$ is alkyloxy, alkynyloxy, alkyloxyalkyloxy, aryloxy, mono- or dialkylamino, Het, aryl, arylalkyl, aryl-Het, alkyl, arylaryl, Het-alkyl, arylthioalkyl or arylalkyloxy, may be prepared by reacting a compound of Formula (XI) with a compound of Formula (XII) in which $L^3$ is a leaving group such as halo, e.g. chloro, with R-DIEA, R-Trisamine and R-NCO, in a suitable solvent such as dichloromethane:

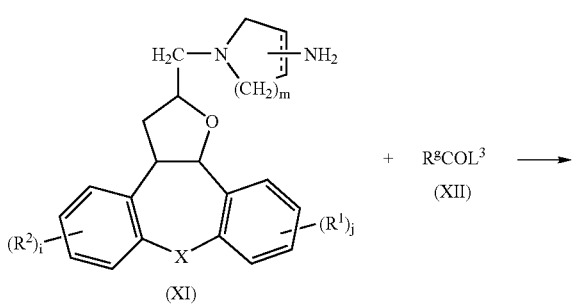

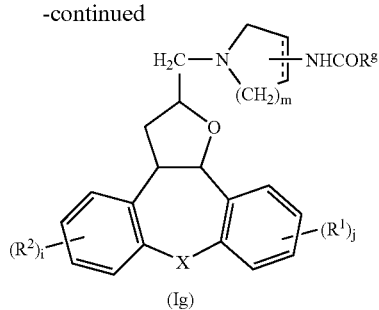

(Ig)

The compounds of Formula (I) in which A is a radical of Formula (a) in which r is 1 and $R^3$ is alkylaminocarbonylamino, arylalkylaminocarbonylamino, arylamino-carbonylamino, aryloxyarylaminocarbonylamino, arylaminothiocarbonylamino, Het-aminothiocarbonylamino, alkyloxycarbonylalkylaminocarbonylamino, amino-alkylaminothiocarbonylamino, Het-alkylaminothiocarbonylamino, alkyloxyalkyl-aminothiocarbonylamino or alkylsulphonylalkylaminothiocarbonylamino, represented by Formula (Ih) in which $R^h$ is alkyl, arylalkyl, aryl, aryloxyaryl or alkyloxycarbonyl-alkyl when X is oxygen, or aryl, Het-, aminoalkyl, Het-alkyl, alkyloxyalkyl or alkylsulphonylalkyl when X is sulphur, may be prepared by reacting a compound of Formula (XI) with a compound of Formula (XIII) where X is O for the preparation of carbonylamino compounds or S for the preparation of thiocarbonylamino compounds, and R-DIEA, R-Trisamine, R-NCO in a suitable solvent such as dichloromethane:

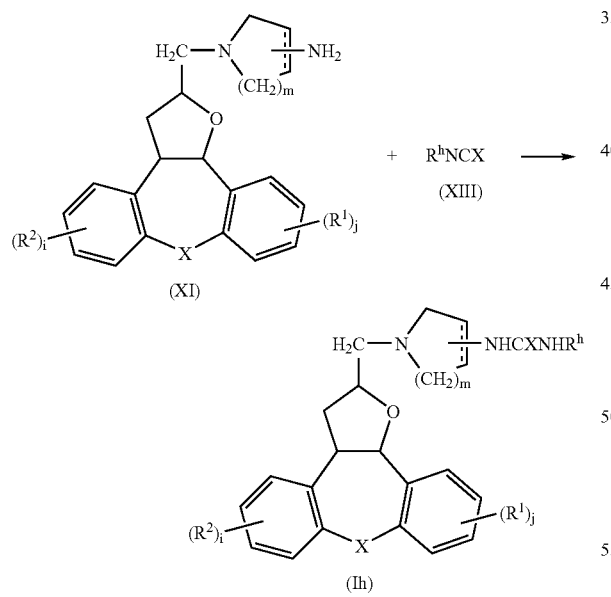

The compounds of Formula (I) in which A is a radical of Formula (c) in which $R^4$ is alkylaminothiocarbonyl, alkyloxycarbonylaminothiocarbonyl, arylaminothiocarbonyl, arylalkylaminothiocarbonyl or arylcarbonylaminothiocarbonyl, represented by Formula (Ii) in which $R^i$ is alkyl, alkyloxycarbonyl, aryl, arylalkyl or arylcarbonyl, may be prepared by reacting a compound of Formula (VI) with a compound of Formula (XIV) and polystyrene-isocyanate in a suitable solvent such as dichloromethane:

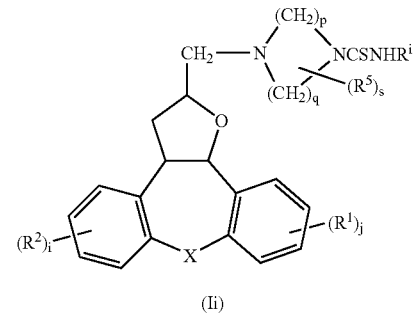

In an analogous manner to the previous process, the compounds of Formula (I) in which A is a radical of Formula (c) in which $R^4$ is alkylaminocarbonyl, arylaminocarbonyl or alkyloxycarbonylalkylaminocarbonyl, represented by Formula (Ij) in which $R^j$ is alkyl, aryl, or alkyloxycarbonylalkyl, may be prepared by reacting a compound of Formula (VI) with a compound of Formula (XV) and polystyrene-isocyanate in a suitable solvent such as dichloromethane:

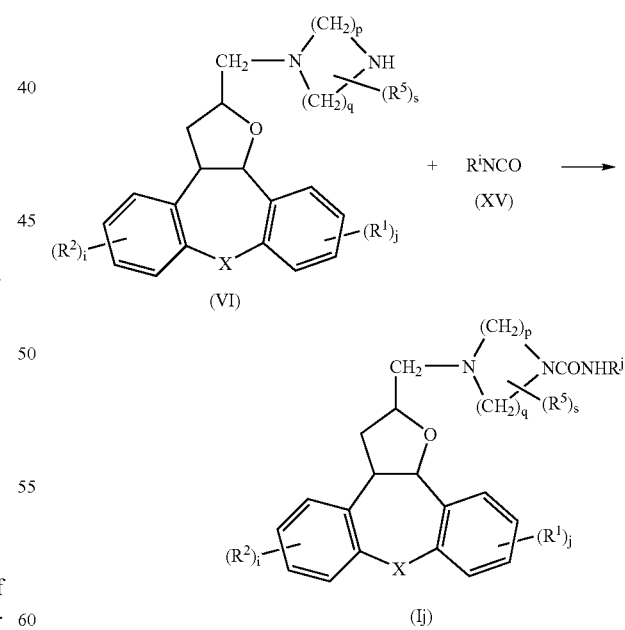

The compounds of Formula (I) in which A is a radical of Formula (c) in which p and q are each 2 and $R^4$ is alkylsulphonyloxyalkyl, represented by Formula (Ik) in which $R^k$ is alkylsulphonyl, may be prepared by reacting a compound of Formula (XVI) with a compound of Formula (XVII) in which $L^4$ is a leaving group such as halo, e.g. chloro, in the presence of a base such as triethylamine, and in a suitable solvent such as dichloromethane:

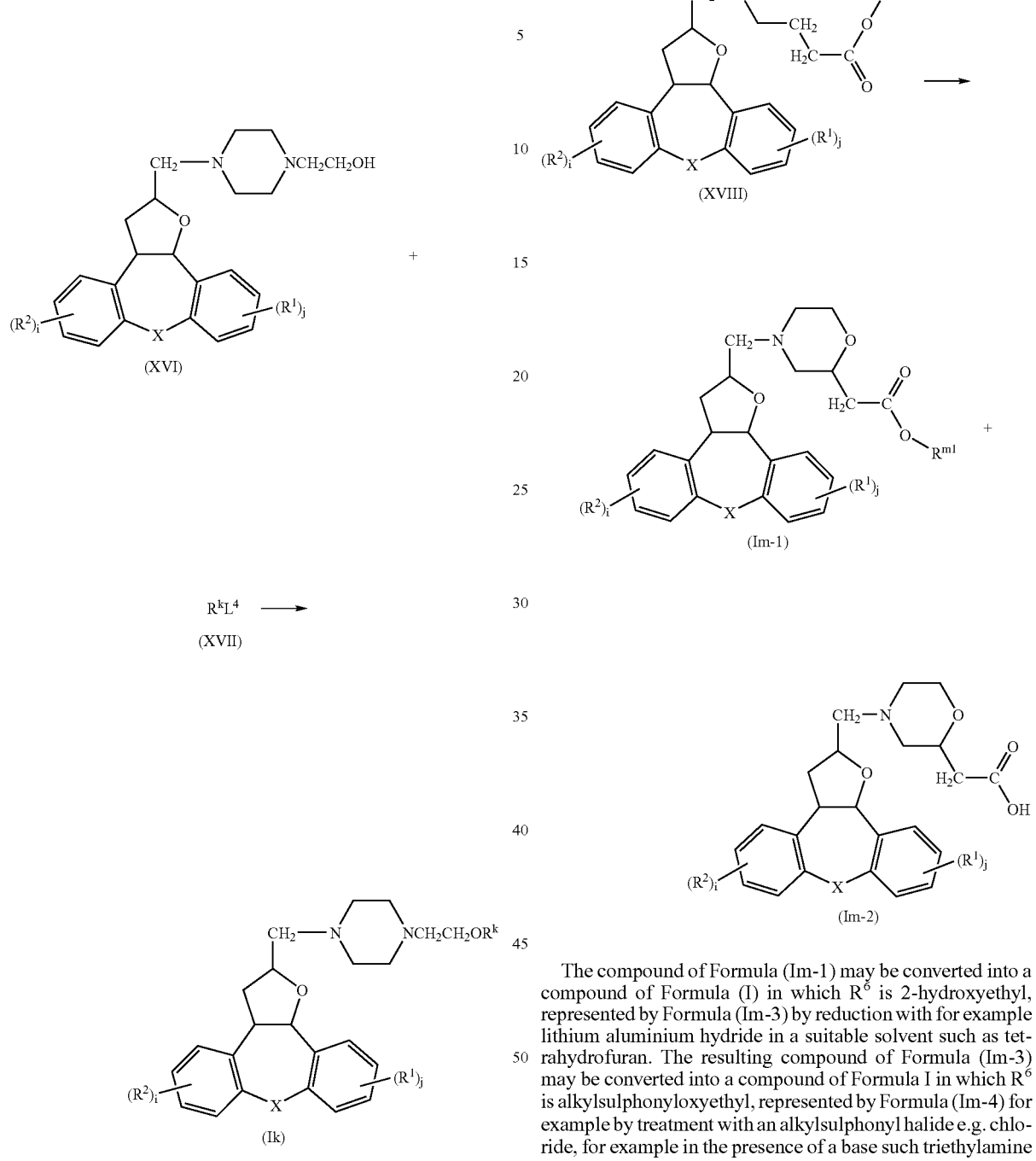

The compounds of Formula (I) in which A is a radical of Formula (d) in which the group $R^6$ is in the 3-position and is alkyloxycarbonylmethyl or hydroxycarbonylmethyl, represented by formulae (Im-1) and (Im-2) respectively in which $R^{m1}$ is alkyl, may be prepared by reacting a compound of Formula (XVIII) for example by treatment with a base such as potassium tert-butoxide in a suitable solvent such as tetrahydrofuran to effect ring closure to form a mixture of compounds of formulae (Im-1) and (Im-2), which may be separated in conventional manner for example by column chromatography:

The compound of Formula (Im-1) may be converted into a compound of Formula (I) in which $R^6$ is 2-hydroxyethyl, represented by Formula (Im-3) by reduction with for example lithium aluminium hydride in a suitable solvent such as tetrahydrofuran. The resulting compound of Formula (Im-3) may be converted into a compound of Formula I in which $R^6$ is alkylsulphonyloxyethyl, represented by Formula (Im-4) for example by treatment with an alkylsulphonyl halide e.g. chloride, for example in the presence of a base such triethylamine and in a suitable solvent such as dichloromethane. The compound of Formula (Im-4) may be converted into a compound of Formula (I) in which $R^6$ is alkyloxyethyl or aryloxyethyl, represented by Formula (Im-5) in which $R^{m2}$ is alkyl or aryl, for example by treatment with a compound of Formula $R^{m2}$-M where M is an alkali metal for example sodium, in a suitable solvent such as methanol or $(CH_3)_2CHO$. Alternatively the compound of Formula (Im-4) may be converted into a compound of Formula (I) in which $R^6$ is mono- or di-alkylaminoethyl, represented by Formula (Im-6) in which $R^{m3}$ is mono- or di-alkylamino, for example by treatment with a compound of Formula $R^{m3}H$ in the presence of a base such as calcium oxide in a suitable solvent such as tetrahydrofuran.

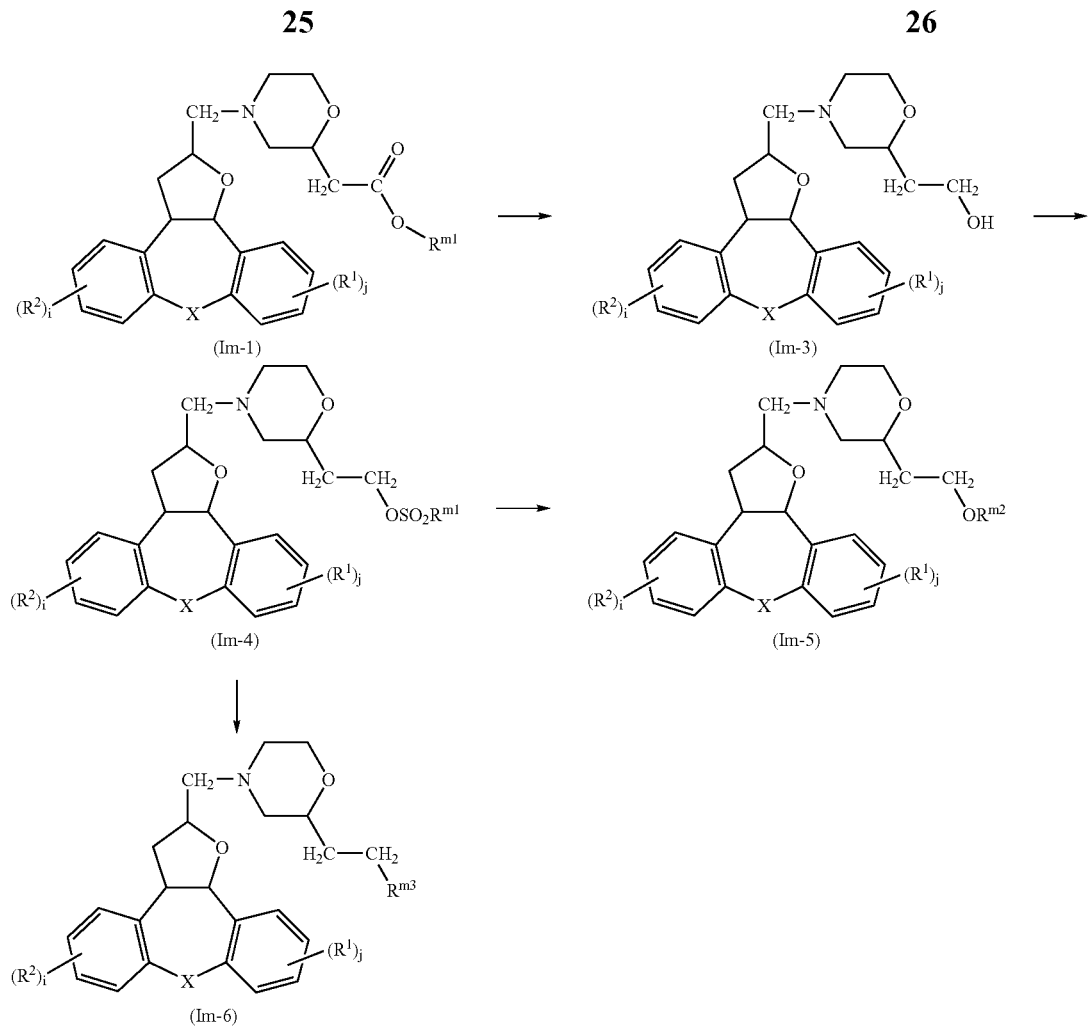

The compound of Formula (Im-2) may alternatively be converted into a compound of Formula (I) in which $R^6$ is mono- or di-alkylaminocarbonylmethyl or arylaminocarbonylmethyl, represented by Formula (Im-7) in which $R^{m4}$ is mono- or di-alkylamino or arylamino, by treatment with a compound of Formula $R^{m4}H$ in the presence of 1-hydroxy-1H-benzotriazole, $(CH_3)_2CHO$ and dicyclohexanecarbodiimide:

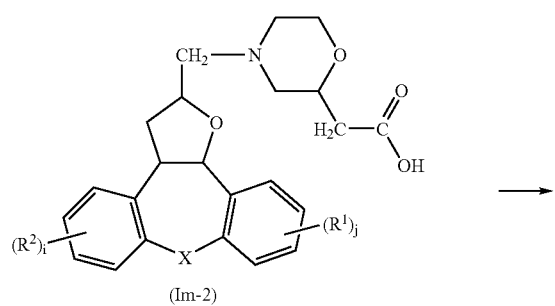

-continued

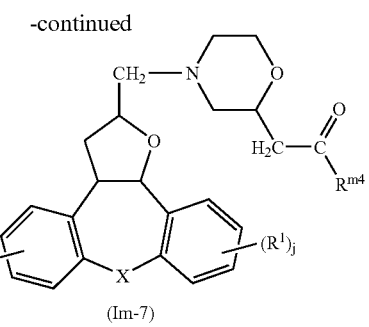

The compounds of Formula (XVIII) may be prepared in conventional for examples as described below in the Examples.

The compounds of Formula (I) may also be converted into each other following art-known transformation reactions, for example:

(a) a compound of Formula (I) in which $R^3$ is hydroxy may be converted into a corresponding compound of Formula (I) in which $R^3$ is oxo by treatment with an oxidizing agent such as ClCOCOCl, for example in the presence of a base such as triethylamine, generally in a solvent such as dichloromethane and/or DMSO;

(b) a compound of Formula (I) in which $R^3$ is oxo may be converted into a corresponding compound of Formula (I) in which $R^3$ is gem(hydroxy)(alkyl) by treatment with a Grignard reagent such as $CH_3MgCl$, generally in a solvent such as tetrahydrofuran;

(c) a compound of Formula (I) in which $R^3$ is hydroxy may be converted into a corresponding compound of Formula (I) in which $R^3$ is alkyloxy by treatment with an appropriate alkylating agent such as an alkyl halide for example an alkyl iodide, for example in the presence of a base such as sodium hydride, generally in a solvent such as 1,2-dimethoxyethane;

(d) a compound of Formula (I) in which $R^3$ is hydroxy may be converted into a corresponding compound of Formula (I) in which $R^3$ is aryloxy by treatment with an appropriate arylating agent such as the corresponding phenol in the presence for example of triphenylphosphine and $CH_3CH_2CON=NCOCH_2CH_3$, generally in a solvent such as tetrahydrofuran; in an analogous manner a compound of Formula (I) in which $R^3$ is hydroxyalkyl may be converted into a corresponding compound of Formula (I) in which $R^3$ is aryloxyalkyl;

(e) a compound of Formula (I) in which $R^3$ is alkyloxycarbonyl may be converted into a corresponding compound of Formula (I) in which $R^3$ is hydroxycarbonyl by hydrolysis under basic conditions for example in the presence of sodium hydroxide or lithium hydroxide, generally in an aqueous solvent such as dioxane;

(f) a compound of Formula (I) in which $R^3$ is alkyloxycarbonyl or alkyloxycarbonylalkyl may be converted into a corresponding compound of Formula (I) in which $R^3$ is hydroxyalkyl by reduction for example in the presence of lithium aluminium hydride, generally in a solvent such as tetrahydrofuran or diethyl ether;

(g) a compound of Formula (I) in which $R^2$ is halo (for example iodo) may be converted into a corresponding compound of Formula (I) in which $R^2$ is cyano by treatment with a cyanide compound, for example zinc cyanide, in the presence of a palladium compound such as $Pd(PPh_3)_4$, in a suitable solvent, for example N,N-dimethylformamide;

(i) a compound of Formula (I) in which $R^3$ is hydroxy may be converted into a corresponding compound of Formula (I) in which $R^3$ is alkylcarbonyloxy, arylcarbonyloxy or arylalkylcarbonyloxy by treatment with an appropriate acylating agent such as an acyl halide for example an acyl chloride, for example in the presence of polymer-supported-DIPEA, -DIEA or -Trisamine, generally in a solvent such as dichloromethane; (ii) a compound of Formula (I) in which $R^3$ is hydroxyalkyl may be converted into a corresponding compound of Formula (I) in which $R^3$ is alkyloxycarbonyloxyalkyl by treatment with an appropriate acylating agent such as an acyl halide for example an acyl chloride, for example in the presence of a base such as 4-dimethylaminopyridine, generally in a solvent such as dichloromethane;

(h) a compound of Formula (I) in which A is a radical of Formula (a), m is 2 and the two $R^3$ groups are hydroxy and 1-propenyl respectively, represented by Formula (In-1) below may be converted into a compound of Formula (In-2) for example by treatment with $I(Py)_2.BF_4$ in a suitable solvent, for example dichloromethane, which can then be converted into a compound of Formula (I) in which A is a radical of Formula (b) and ring B is substituted by a hydroxymethyl group, represented by Formula (In-3) below for example by treatment with sodium methoxide in a suitable solvent for example methanol:

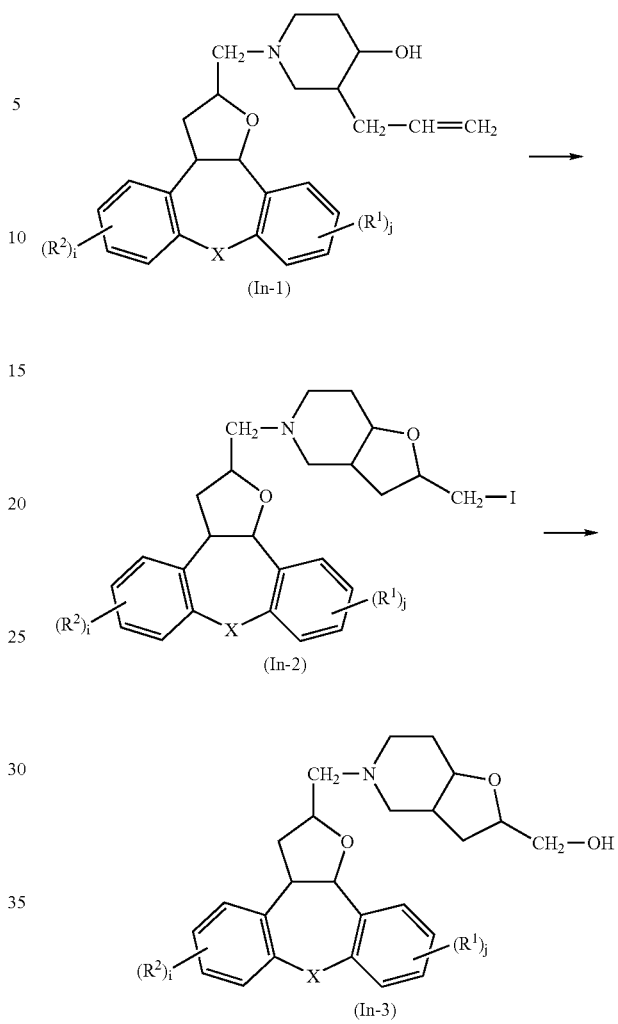

(j) a compound of Formula (I) in which A is a radical of Formula (a) in which $R^3$ is hydroxyalkyl may be converted into a corresponding compound of Formula (I) in which $R^3$ is alkylamino-carbonyloxyalkyl, arylaminocarbonyloxyalkyl or arylalkylaminocarbonyloxyalkyl, by treatment with an appropriate $R°NCO$ compound in which $R°$ is alkyl, aryl or arylalkyl, for example in the presence of a base such as triethylamine or 4-dimethylaminopyridine, generally in a solvent such as dichloromethane; in an analogous manner a compound of Formula (I) in which $R^6$ is hydroxyalkyl may be converted into a corresponding compound of Formula (I) in which $R^6$ is alkylaminocarbonyloxyalkyl.

The intermediate compounds mentioned hereinabove are either commercially available or may be made following art-known procedures. For instance, intermediate compounds of Formula (III) may be prepared according to the procedure described by Monkovic et al. (*J. Med. Chem.* (1973), 16(4), p. 403-407).

Alternatively, intermediate compounds of Formula (III) can also be prepared by reacting an epoxide derivative of Formula (XIX) with a Grignard reagent of Formula (XX) wherein X suitably is halo, thus forming an intermediate compound of Formula (XXI) which may subsequently be cyclized according to art-known methods such as the one described in Monkovic et al.

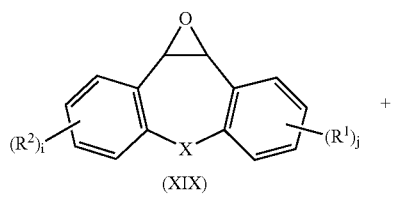

(XIX)

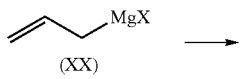

(XX)

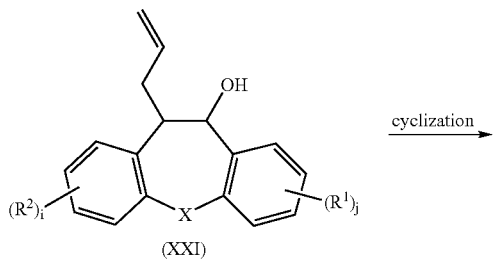

(XXI)

cyclization

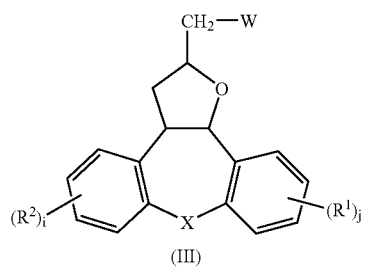

(III)

Epoxides of Formula (XIX) can be prepared using art-known procedures such as epoxidating an intermediate compound of Formula (XXII) with a suitable peroxide such as m-chloroperbenzoic acid.

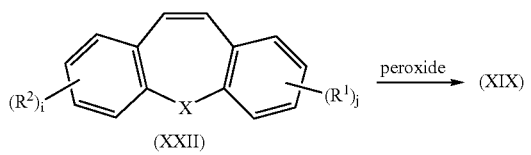

(XXII) peroxide → (XIX)

Pure stereochemically isomeric forms of the compounds of Formula (I) may be obtained by the application of art-known procedures. Diastereomers may be separated by physical methods such as selective crystallization and chromatographic techniques, e.g. counter-current distribution, liquid chromatography and the like.

Experimental Part

Hereinafter, "DMF" is defined as N,N-dimethylformamide, "DCM" is defined as dichloromethane, "DIPE" is defined as diisopropyl ether, "DMSO" is defined as dimethylsulfoxide, "Et$_2$O" is defined as diethyl ether, "EtOAc" is defined as ethyl acetate, "EtOH" is defined as ethanol, "MeOH" is defined as methanol, "TFA" is defined as trifluoroacetic acid, "THF" is defined as tetrahydrofuran.

A. Preparation of the intermediate compounds

EXAMPLE A1

Preparation of Intermediate 1

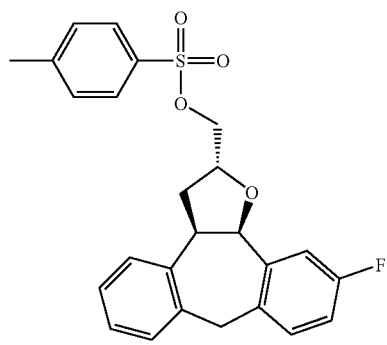

[2R-(2α,3aα,12bβ)]

[2R-(2α, 3aα, 12bβ)]-11-fluoro-2-hydroxymethyl-3,3a,8,12b-tetrahydro-2H-dibenzo [3,4:6,7]cyclohepta[1,2-b]furan (4.1 g, 0.0144 mol) was dissolved in DCM (20 ml). Triethylamine (0.0173 mol) was added and the mixture was cooled on an ice-bath. A solution of 4-methyl-benzenesulfonyl chloride (0.0159 mol) in DCM (10 ml) was added over ±5 min. The mixture was stirred for 2 hours at 0° C. then allowed to warm to room temperature. The reaction mixture was stirred overnight at room temperature. Water (20 ml) was added. The layers were separated. The organic phase was stirred in a 10% aqueous potassium carbonate solution for one hour. The layers were separated. The organic layer was dried (MgSO$_4$), filtered and the solvent evaporated. The residue was stirred in toluene (30 ml). A 10% aqueous potassium carbonate solution (30 ml) was added. The layers were separated. The organic layer was dried (MgSO$_4$), filtered and the solvent evaporated, yielding 5.8 g (92%) of [2R-(2α, 3aα, 12bβ)]11-fluoro-3,3a,8,12b-tetrahydro-2H-dibenzo[3,4:6,7]cyclohepta[1,2-b]furan-2-methanol-4-methylbenzenesulfonate, intermediate 1. An alternative method of preparing this intermediate is described in WO03/048146 [CAS number=543741-40-8].

EXAMPLE A2

Preparation of Intermediate 2

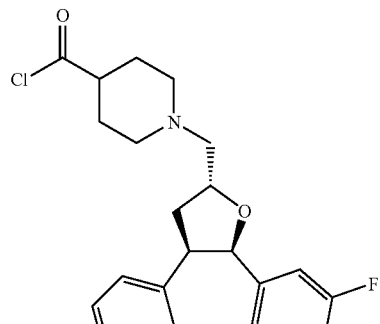

[2R-(2α,3aα,12bβ)]

Thionyl chloride (0.006325 mol) was added slowly at 0° C. to a mixture of compound 156 (0.001265 mol) in toluene (6 ml), the reaction mixture heated at 70° C. for 10 hours and then it was cooled to room temperature. Volatiles were evaporated in vacuo. Toluene (10 ml) was added and the mixture was evaporated in vacuo, yielding intermediate 2.

EXAMPLE A3

Preparation of Intermediate 3

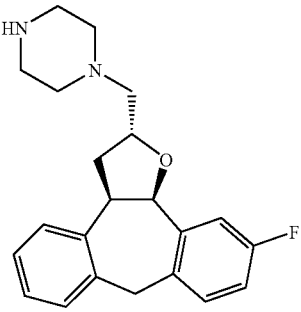

2R-(2α,3aα,12bβ)]

A mixture of intermediate 1 (0.023 mol), piperazine (0.23 mol) and calcium oxide (2.3 mol) in THF was stirred and heated for 16 hours at 140° C. (oil bath temperature), then the reaction mixture was cooled to room temperature. The solids were filtered off and the filtrate was evaporated. The residue was taken up in EtOAc and was washed two times with water.

The organic layer was separated, dried ($Na_2SO_4$), filtered and the solvent was evaporated (vac.), yielding intermediate 3 as a brown oil.

EXAMPLE A4 a) Preparation of Intermediate 4

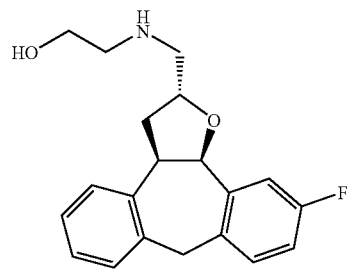

2R-(2α,3aα,12bβ)]

A mixture of intermediate 1 (0.0068 mol), 2-amino-ethanol (0.068 mol) and calcium oxide (0.068 mol) in THF (15 ml) was heated at 120° C. (oil bath temperature) for 16 hours. The resulting suspension was filtered through celite and the filtrate was evaporated under reduced pressure. The residue was partitioned between DCM/water; the organic layer was separated, washed with $NaHCO_3$, with water and with brine, then dried ($Na_2SO_4$), filtered off and the solvent was evaporated. The residual oil was purified by short open column chromatography over silica gel (eluent: DCM/MeOH 95/5). The product fractions were collected and the solvent was evaporated, yielding 2.2 g (99%) of intermediate 4.

b) Preparation of Intermediate 5

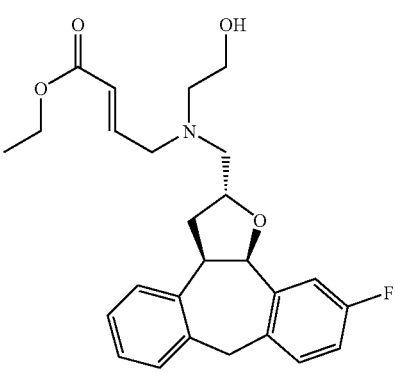

(E)-[2R-(2α,3aα,12bβ)]

A mixture of intermediate 4 (0.0067 mol), (E)-4-bromo-2-butenoic acid, ethyl ester (0.0067 mol) and triethylamine (0.0067 mol) in water (30 ml) was stirred and refluxed for 3 hours, then the reaction mixture was cooled to room temperature. Sodium hydroxide (0.010 mol) was added and the mixture was stirred for 30 minutes, then partitioned between DCM/water. The organic layer was separated, washed with water and with brine, dried ($MgSO_4$), filtered off and the solvent was evaporated, yielding 2.8 g of intermediate 5 (used as such in the next reaction step without further purification)

EXAMPLE A5

Preparation of Intermediate 6

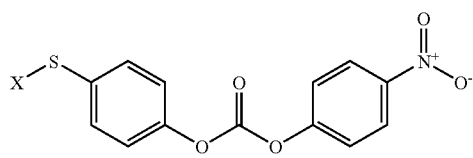

4-methylmorpholine (0.078 mol) and a solution of carbonochloridic acid, 4-nitrophenyl ester (0.0157 g) in DCM were added slowly to a suspension of polymer-bound 4-mercaptophenol (Aldrich, catalogue number 511714, 0.039 mol; loading 1.3 mmol/g) in DCM, anhydrous (200 ml) The pressure was removed and the mixture was stirred overnight at room temperature. The solids were filtered off, washed with THF/DCM (anhydrous) and dried (vac.), yielding intermediate 6.

EXAMPLE A6 a) Preparation of Intermediate 7

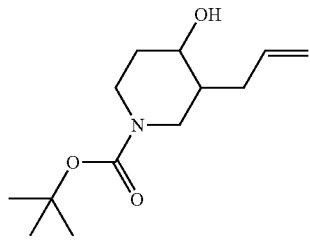

mixture of diastereoisomers 87:13

To a mixture of 4-oxo-3-(2-propenyl)-1-piperidinecarboxylic acid, 1,1-dimethylethyl ester (1.67 mmol) in THF (20 ml) and methanol (10 ml) at room temperature, sodium tetrahydroborate (3.33 mmol) was added portionwise. The resulting mixture was stirred for 3 hours at room temperature and then quenched with an aqueous saturated NH$_4$Cl solution and stirred for 10 minutes. The organic layer was separated, dried (Na$_2$SO$_4$), filtered and the solvent was evaporated, yielding 0.411 g intermediate 7.

b) Preparation of Intermediate 8

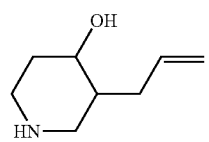

TFA (0.102 mol, 30% solution in DCM) was added to intermediate 7 (0.01019 mol) and the resulting solution was stirred at room temperature under N$_2$ for 4 hours. A 20% aqueous potassium carbonate solution was added and the resulting solution was stirred at room temperature for 1 hour. The organic layer was separated, dried (Na$_2$SO$_4$) and the solvent was evaporated under reduced pressure, yielding 2.45 g of intermediate 8 (colourless oil, used as such without further purification).

EXAMPLE A7 a) Preparation of Intermediate 9

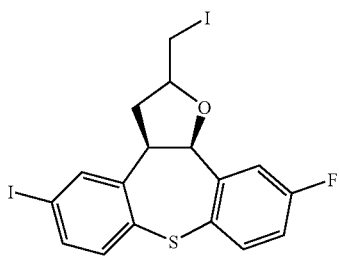

A mixture of

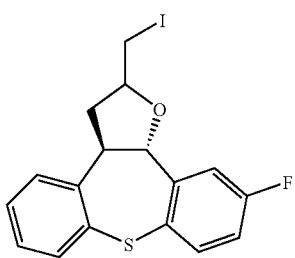

described in J. Med. Chem. 2005, Vol. 48 No. 6, pages 1709-1712 (0.0106 mol), bis(pyridine)iodonium tetrafluoroborate (0.0117 mol) and TFA (0.0212 mol) in DCM (50 ml) was stirred for one hour at room temperature, under N$_2$ atmosphere. The reaction mixture was washed with Na$_2$S$_2$O$_3$ (2×50 ml), and with brine (2×50 ml). The organic layer was separated, dried (Na$_2$SO$_4$), filtered and the solvent was evaporated. The residue (oil) was purified by short open column chromatography over silica gel (eluent: heptane/EtOAc 9/1). The product fractions were collected and the solvent was evaporated, yielding 3.9 g (68.4%) of intermediate 9.

EXAMPLE A8

Preparation of Intermediate 10

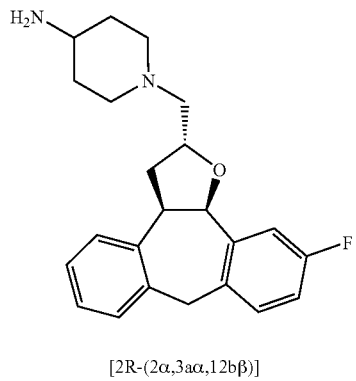 [SMILES: NC1CCN(C[C@H]2C[C@@H]3c4ccccc4Cc4ccc(F)cc4[C@@H]3O2)CC1]

[2R-(2α,3aα,12bβ)]

A mixture of intermediate 1 (0.01824 mol), tert-butyl 4-piperidylcarbamate (10 g) and calcium oxide (q.s.) in THF (q.s.) was stirred and heated at 130° C. (oil-bath temperature) for 8 hours. The mixture was cooled to room temperature and then filtered. The solvent was evaporated. The residue was taken up into EtOAc and washed with a saturated aqueous NaHCO$_3$ solution. The organic layer was separated, dried (Na$_2$SO$_4$), filtered and the solvent was evaporated (vacuum). The residue was taken up into a 25% TFA solution in DCM (deprotection). The mixture was stirred at room temperature for 3 hours and the solvent was evaporated. The residue was taken up into DCM and then washed twice with a saturated aqueous NaHCO$_3$ solution. The organic layer was separated, dried (Na$_2$SO$_4$), filtered and the solvent was evaporated (vacuum). The residue was purified by short open column chromatography. The product fractions were collected and the solvent was evaporated, yielding intermediate 10.

EXAMPLE A9

Preparation of Intermediate 11

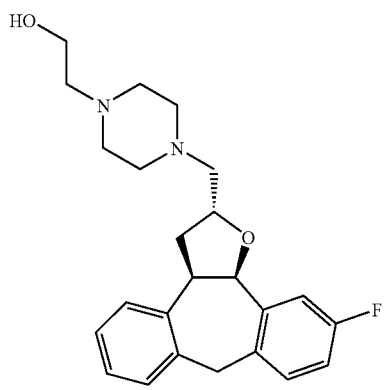

[2R-(2α,3aα,12bβ)]

[2R-(2α, 3aα, 12bβ)]11-Fluoro-3,3a,8,12b-tetrahydro-N-methyl-2H-dibenzo[3,4:6,7]cyclohepta[1,2-b]furan-2-methanamine (described in WO 03/048146) (0.0114 mol) and 1-piperazine-ethanol (0.0342 mol) were irradiated under microwave conditions (power: 500 Watt; 150° C.; 15 min). Then, the resulting mixture was diluted with EtOAc. The organic solution was washed with water, dried (Na$_2$SO$_4$), filtered and the solvent evaporated under reduced pressure. The residue was purified by short open column chromatography over silica gel (eluent: DCM/MeOH 97/3). The product fractions were collected and the solvent was evaporated, yielding 2.5 g of intermediate 11 as an orange oil which was used without further purification.

B. Preparation of the Final Compounds

EXAMPLE B1

Preparation of Compound 1

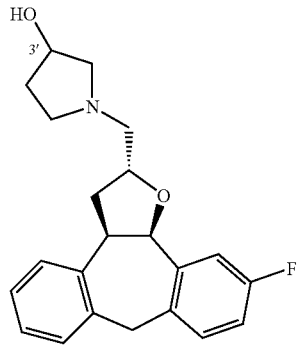

[2R-(2α,3aα,12bβ)](3'RS) C$_2$H$_2$O$_4$ (1:1);
mixture of diastereoisomers 1:1

A mixture of intermediate 1 (0.00253 mol), 3-pyrrolidinol (0.00759 mol) and calcium oxide (0.250 g) in THF (30 ml) was stirred and heated at 140° C. (oil bath temperature) for 8 hours, then the cooled mixture was filtered off and the solvent was evaporated. The residue was purified by high-performance liquid chromatography prep. The product fractions were collected and the solvent was evaporated. The residue (free base) was dissolved in diethyl ether and converted into the ethanedioate salt (1:1). The precipitate was filtered off, then dried, yielding compound 1.

EXAMPLE B2

Preparation of Compound 144

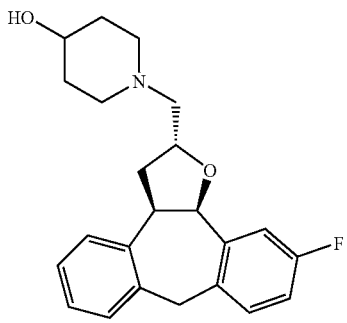

[2R-(2α,3aα,12bβ)]·C$_2$H$_2$O$_4$ (1:1)

Intermediate 1 (0.00096 mol), 4-piperidinol (0.0012 mol), calcium oxide (0.013 mol) and THF dry (q.s.) were heated at 140° C. (oil bath temperature) for 16 hours. The mixture was cooled to room temperature and the solid was filtered off. The solvent was evaporated (vac.) and the residue was taken up in DCM, washed with an aqueous saturated Na$_2$CO$_3$ solution and with water. The organic layer was separated, dried (MgSO$_4$) and the solvent was evaporated (vac.). The residue was purified by short open column chromatography (eluent: DCM/(MeOH/NH$_3$) 100/0, 98/2). The product fractions were collected and the solvent was evaporated. The residue was treated with ethanedioic acid and converted into the ethanedioate salt in Et$_2$O. The resulting precipitate was filtered off, washed with cold Et$_2$O and dried in vacuo, yielding 0.070 g of compound 144.

EXAMPLE B3

Preparation of Compounds 153 and 154

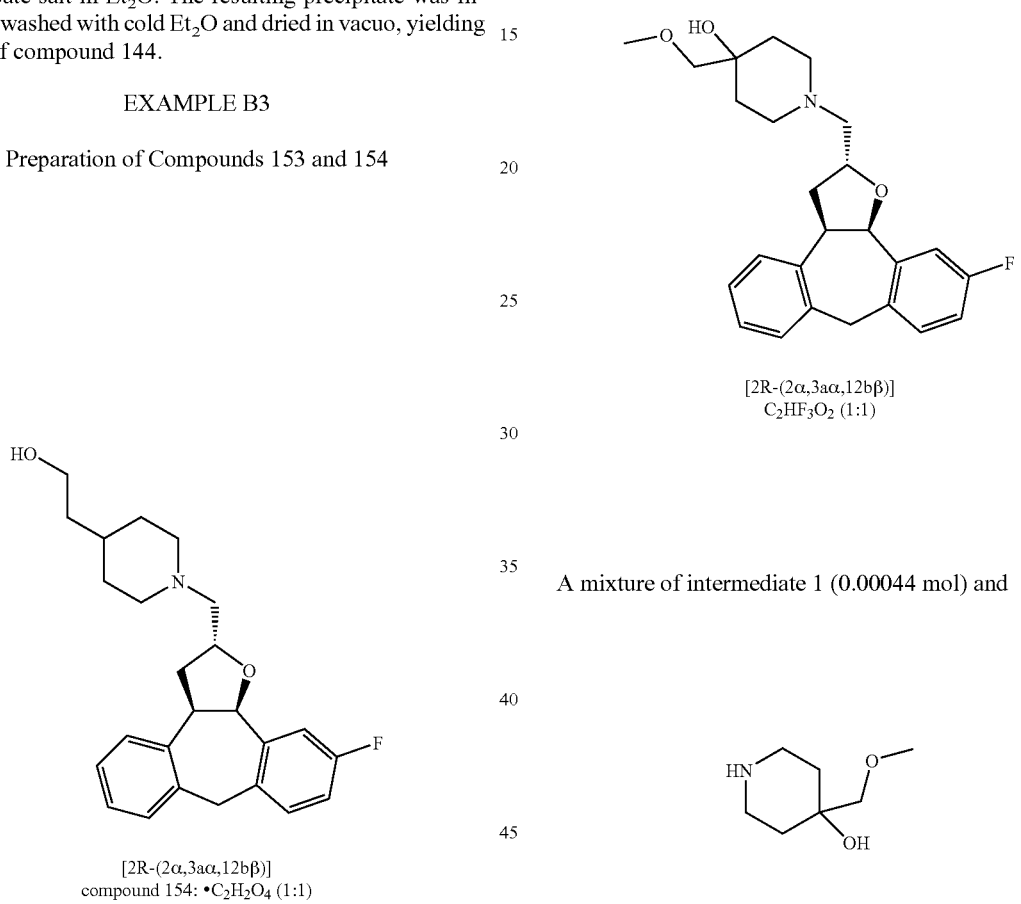

[2R-(2α,3aα,12bβ)]
compound 154: •C$_2$H$_2$O$_4$ (1:1)
compound 153: free base

A mixture of intermediate 1 (0.00091 mol), 4-piperidineethanol (0.00456 mol) and calcium oxide (0.0045 mol) in acetonitrile (q.s.) was stirred and heated in a sealed tube for 3 days at 100° C. The reaction mixture was filtered through a celite pad and the filtrate was evaporated. The residue thus obtained was purified by short open column chromatography (eluent: DCM/MeOH 98.5/1.5). The product fractions were collected and the solvent was evaporated, yielding 0.343 g of compound 153. Part of this fraction was converted into the ethanedioic acid salt by treatment with oxalic acid in Et$_2$O, the formed precipitate was filtered off, washed with cold Et$_2$O and dried, yielding compound 154.

EXAMPLE B4

Preparation of Compound 272

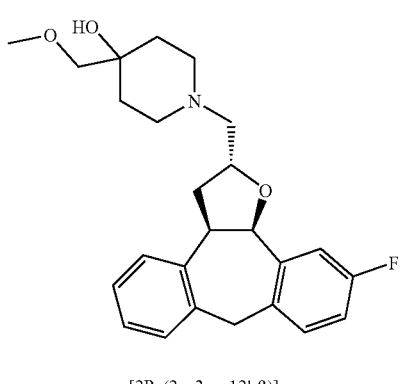

[2R-(2α,3aα,12bβ)]
C$_2$HF$_3$O$_2$ (1:1)

A mixture of intermediate 1 (0.00044 mol) and

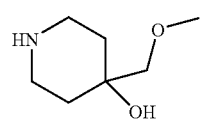

(0.00088 mol) [described in Journal of Heterocyclic Chemistry (1968), 5 (4), 467-9], potassium carbonate (0.00088 mol) and DMF (q.s.) was irradiated under microwave conditions at 160° C. for 20 minutes and the solvent was evaporated under N$_2$-flow. The residue was dissolved in THF, then polystyrene-methylisocyanate (3 eq., Aldrich, ref 47368-5: 200-400 mesh; loading 1.85 mmol/g)) (0.00044 mol) was added and the reaction mixture was shaken for 5 hours. The resin was filtered off and the filtrate was evaporated. The residue was dissolved in MeOH (5 ml), polystyrene-SO$_3$H (3 eq., Fluka, ref 06423, 20-50 mesh, loading 4.6 mmol/g) (0.00044 mol) was added, then the mixture was shaken for 3 hours, washed and treated twice with MeOH/NH$_3$ (saturated). The mixture was filtered off and the filtrate was evaporated. The residue was purified by preparative high-performance liquid chromatography. The product fractions were collected and

EXAMPLE B5

Preparation of Compound 276

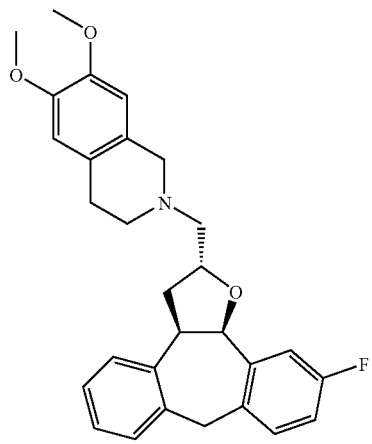

[2R-(2α,3aα,12bβ)]
C₂HF₃O₂ (1:1)

A mixture of intermediate 1 (1 mol.equiv.), 1,2,3,4-tetrahydro-6,7-dimethoxy-isoquinoline, hydrochloride (3 mol.equiv.) and potassium carbonate (2 mol.equiv.) in acetonitrile (10 ml) was stirred and heated at 130° C. for 45 minutes in a microwave oven (600 W). The solvent was evaporated and the residue was taken up in DCM, then the solids were filtered off and the solvent was evaporated. The residue was purified by reversed phase high-performance liquid chromatography. The product fractions were collected and the solvent was evaporated, yielding compound 276.

EXAMPLE B6

Preparation of Compounds 277 and 278

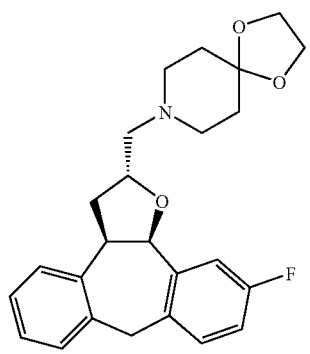

compound 277: [2R-(2α,3aα,12bβ)], free base
compound 278: [2R-(2α,3aα,12bβ)] C₂H₂O₄ (1:1)

A mixture of intermediate 1 (0.00137 mol), 1,4-dioxa-8-azaspiro[4.5]decane (0.00682 mol) and calcium oxide (0.00696 mol) in acetonitrile (20 ml) was heated in a sealed tube at 100° C. for 2 days, then the suspension was filtered through a celite pad and the filtrate was evaporated under reduced pressure. The residue was purified by short open column chromatography (eluent: DCM/MeOH 99/1). The product fractions were collected and the solvent was evaporated, yielding 0.300 g of compound 277 (free base). A part of the residue was converted into the ethanedioate salt by treatment with oxalic acid in Et₂O, the formed precipitate was collected by filtration, washed with cold Et₂O and dried in vacuo, yielding compound 278.

EXAMPLE B7 a) Preparation of Compounds 161 and 162

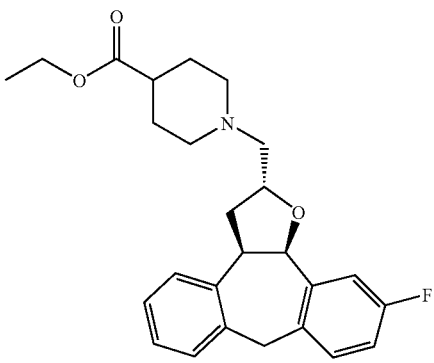

compound 161: [2R-(2α,3aα,12bβ)] free base
compound 162: [2R-(2α,3aα,12bβ)] •C₂H₂O₄ (1:1)

A mixture of intermediate 1 (0.000456 mol), 4-piperidinecarboxylic acid, ethyl ester (0.00458 mol) and calcium oxide (0.00232 mol) in acetonitrile (20 ml) was heated in a sealed tube at 100° C. for 3 days, then the suspension was filtered over celite and the filtrate was evaporated under reduced pressure. The residue was purified by short open column chromatography (eluent: DCM/MeOH 100/0→99/1) and then further purified by flash column chromatography (eluent: DCM/MeOH 99/1). The product fractions were collected and the solvent was evaporated, yielding 0.288 g of compound 161. The residual oil was converted into the ethanedioate salt which was collected and dried in vacuo, yielding 0.085 g of compound 162 (32.7%).

b) Preparation of Compounds 156 and 157

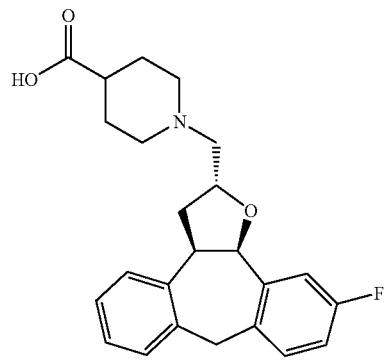

compound 156: [2R-(2α,3aα,12bβ)] free base
compound 157: [2R-(2α,3aα,12bβ)] •C₂H₂O₄ (1:1)

A mixture of compound 161 (0.01818 mol) and lithium hydroxide (aqueous solution, 20 ml, 0.02 mol) in 1,4-dioxane (70 ml) was stirred at room temperature for 16 hours, the reaction mixture was concentrated under reduced pressure and the residue was lyophilised, yielding 7 g (white solid) of compound 156. A part of this fraction was converted into the ethanedioate salt (1:1). The resulting precipitate was filtered off and dried, yielding the said salt, compound 157, as a grey solid.

c) Preparation of Compound 178

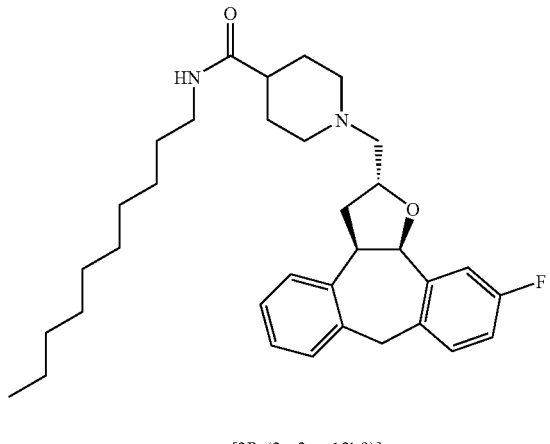

[2R-(2α,3aα,12bβ)]
•C₂HF₃O₂ (1:1)

1-Decanamine (0.00029 mol) and PS-Diisopropylamine (Aldrich, ref 53873-6; 100-200 mesh, loading 2.0-3.5 mmol/g) (0.000408 mol) were added to a mixture of intermediate 2 (0.0002415 mol) in DCM (2 ml) and TFA (cat.quant., 3 drops) and then the reaction mixture was stirred for 2 hours. A mixture of PS-TRIAMINE (Aldrich, ref 47,210-7; 200-400 mesh, loading 4.2 mmol/g) (0.0004 mol), MP-CARBONATE (Fluka, ref 21850; loading 3.5 mmol/g) (0.00096 mol) and PS-ISOCYANATE (3 eq., Aldrich, ref 47368-5: 200-400 mesh; loading 1.85 mmol/g) (0.0003 mol) in DMF (2 ml) was added and the resulting mixture was stirred for 24 hours. The crude was filtered off and the filtrate was evaporated, yielding compound 178.

EXAMPLE B8

Preparation of Compound 166

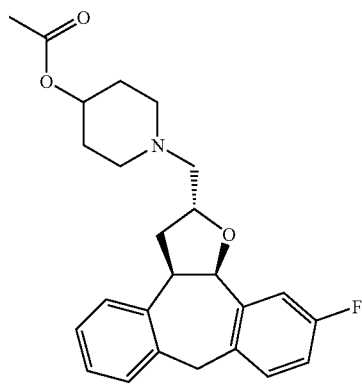

[2R-(2α,3aα,12bβ)]
•C₂H₂O₄ (1:1)

PS-Diisopropylamine (Aldrich, ref 53873-6; 100-200 mesh, loading 2.0-3.5 mmol/g) (0.200 g) was washed twice with DCM and then was suspended in DCM dry (15 ml). Compound 144 (0.00023 mol) and acetyl chloride (0.00025 mol) were added and the reaction mixture was shaken at room temperature overnight. The polymer was filtered off and washed with DCM. The organic filtrates were combined and evaporated. The residue was treated with ethanedioic acid and converted into the ethanedioate salt in Et₂O. The resulting precipitate was filtered off, washed with cold Et₂O and dried in vacuo, yielding 0.047 g of compound 166.

EXAMPLE B9

Preparation of Compound 86

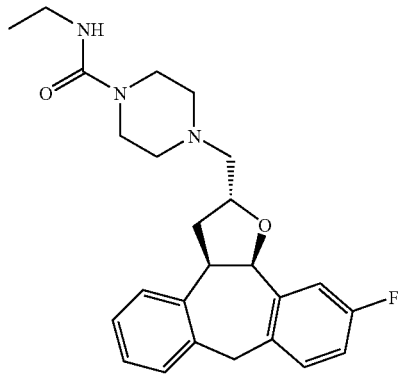

[2R-(2α,3aα,12bβ)]
•C₂H₂O₄ (1:1)

Ethylisocyanate (0.9 equiv.) was added at room temperature in one portion to a solution of intermediate 3 (1 equiv.) in DCM (6 ml). The reaction mixture was stirred at room temperature for 1 hour, then polystyrene-isocyanate (3 eq., Aldrich, ref 47368-5: 200-400 mesh; loading 1.85 mmol/g) was added and the mixture was stirred overnight. The polymer was filtered off and the solvent was evaporated. The residue was purified by short open column chromatography. The product fractions were collected and the solvent was evaporated, yielding the corresponding free base that was converted in the corresponding ethanodioic acid salt by treatment with oxalic acid in Et2O. The formed precipitate was filtered off, washed with cold Et2O and dried under vacuum yielding compound 86.

EXAMPLE B 10

Preparation of Compound 119

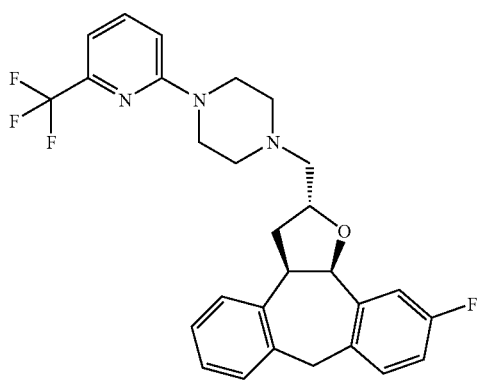

[2R-(2α,3aα,12bβ)]

$C_2HF_3O_2(1:1)$

A mixture of intermediate 3 (0.425 mmol) and 2-chloro-6-(trifluoromethyl)-pyridine (1.275 mmol) in DMSO (5 ml) was stirred at 140° C. for 45 minutes in a microwave oven at 300 Watt. Water was added and the reaction mixture was extracted with DCM. The separated organic layer was washed with brine, dried (Na2SO4), filtered and the solvent was evaporated. The residue was purified by high performance liquid chromatography over reversed phase. The desired fractions were collected and the solvent was evaporated. The residue was converted into the TFA salt, yielding compound 119.

EXAMPLE B 11

Preparation of Compound 78

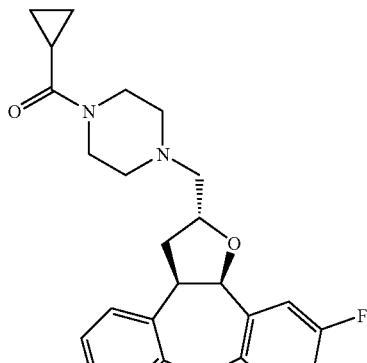

[2R-(2α,3aα,12bβ)]
•C2H2O4 (1:1)

Cyclopropanecarbonyl chloride (1.1 equiv) and triethylamine (2 equiv) were added to a solution of intermediate 3 (0.000567 mol, 1 equiv) in DCM (3 ml), stirred at room temperature. The reaction mixture was stirred for 6 hours at room temperature. PS-Trisamine (Aldrich, ref 47,210-7; 200-400 mesh, loading 4.2 mmol/g),1 equiv) was added to scavenge excess of cyclopropanecarbonyl chloride, while stirring for one hour. Then, the resin was filtered off and the filtrate was evaporated in vacuo. The residue was purified by short open column chromatography over silica gel. The product fractions were collected and the solvent was evaporated. The free base residue was dissolved in Et2O and converted into the ethanedioate salt (1:1). The precipitate was filtered off, washed with cold Et2O and dried in vacuo, yielding 0.04742 g of compound 78.

EXAMPLE B 12 a) Preparation of Compound 7

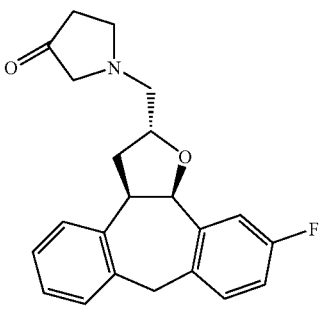 [SMILES: O=C1CCN(C[C@H]2C[C@@H]3c4ccccc4Cc4ccc(F)cc4[C@@H]3O2)C1]

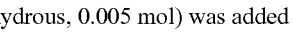

DMSO (anhydrous, 0.005 mol) was added at −60° C. to a solution of ethanedioyl dichloride (0.0025 mol) in DCM (anhydrous, 1 ml) under a nitrogen atmosphere and the reaction mixture was stirred for 5 min. at −60° C. A mixture of the free base of compound 1 (0.0005 mol) in DCM (2 ml) was added at −60° C. and the resulting mixture was stirred for 2 hours at −60° C. Triethylamine (0.007 mol) was added at −60° C. and then the reaction mixture was allowed to reach room temperature. An aqueous saturated $NaHCO_3$ solution was added; the organic layer was separated, dried ($Na_2SO_4$) and the solvent was evaporated. The residue was purified in a manifold (vac.) (eluent 1: DCM; eluent 2: DCM/EtOAc 4/1). The product fractions were collected and the solvent was evaporated. The residue was washed with DIPE and dried, yielding 0.077 g (22%) of compound 7.

b) Preparation of Compound 39

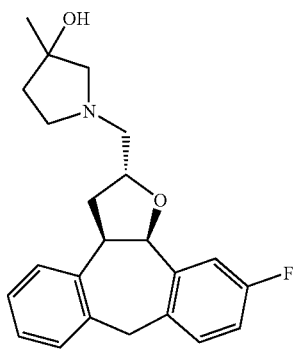

[2R-(2α,3aα,12bβ)]-(3'RS),
(1:1) mixture of diasteroisomers
•$C_2H_2O_4$ (1:1)

Chloromethyl-magnesium (0.00059 mol) was added at 0° C. to a solution of compound 7 (0.00028 mol) in THF dry (1 ml) under a nitrogen atmosphere and the reaction mixture was stirred for 1 hour at room temperature. A 10% aqueous $NH_4Cl$ solution was added and the mixture was extracted with DCM. The organic layer was separated, dried ($Na_2SO_4$) and the solvent was evaporated. The residue was purified by short open column chromatography (eluent 1: DCM/MeOH 95/5; eluent 2: DCM/(MeOH/$NH_3$) 95/5). The product fractions were collected and the solvent was evaporated. The residue was converted into the ethanedioate salt in ether. The resulting precipitate was collected, washed with cold Et2O and dried in vacuo, yielding 0.0985 g (77%) of compound 39.

EXAMPLE B13

Preparation of Compound 69

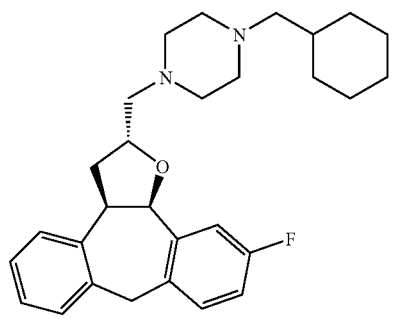

[2R-(2α,3aα,12bβ)]
•$C_2HF_3O_2$ (1:1)

PS-CNBH$_4$Na(Fluka, ref 17337; loading 2.5-4.5 mmol/g) (0.0006 mol) was added to a solution of intermediate 3 (0.0002414 mol) and cyclohexanecarboxaldehyde (0.0003621 mol) in THF/acetic acid (2.2 ml/0.14 ml) (2.34 ml) and the reaction mixture was stirred for 20 hours at room temperature. The mixture was filtered off and the solvent was evaporated. The crude residue was treated with PS-SO3H (3 eq., Fluka, ref 06423, 20-50 mesh, loading 4.6 mmol/g) and MeOH (0.000361 mol) and the mixture was stirred for 20 hours. The resin was filtered off and washed with MeOH. The resin was treated with MeOH saturated with amonia for 5 h. The resin was filtered off and the MeOH-amonia solution was concentrated in vacuo, yielding compound 69.

EXAMPLE B 14

Preparation of Compound 56

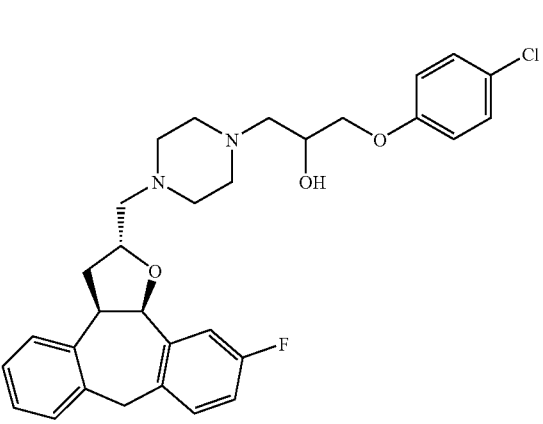

[2R-(2α,3aα,12bβ)]-(2'RS)
(1:1) mixture of diastereoisomers
$C_2H_2O_4$ (1:2)

A mixture of intermediate 3 (0.000567 mol) and 4-chlorophenylglycidyl ether (2 equiv) in 2-propanol (20 ml) was stirred overnight at 130° C. (oil-bath temperature). The reaction mixture was cooled to room temperature. The solvent was evaporated. The residue was purified by HPLC. The product fractions were collected and the solvent was evaporated, yielding the corresponding free base that was converted in the corresponding ethanodioic acid salt by treatment with oxalic acid in Et2O. The formed precipitate was filtered off, washed with cold Et2O and dried under vacuum yielding 0.05628 g of compound 56.

EXAMPLE B 15 a) Preparation of Compounds 159 and 160

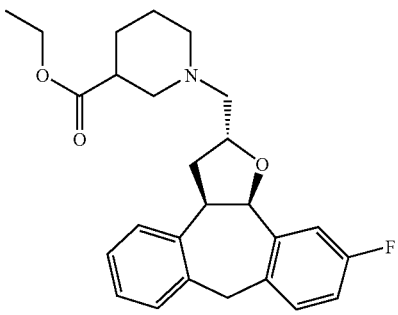

compound 159: [2R-(2α,3aα,12bβ)]-(3'RS)
(1:1) mixture of diastereoisomers, free base
compound 160: [2R-(2α,3aα,12bβ)]-(3'RS)
(1:1) mixture of diastereoisomers, •C₂H₂O₄ (1:1)

A mixture of intermediate 1 (0.00182 mol), 3-piperidinecarboxylic acid, ethyl ester (0.00914 mol) and calcium oxide (0.00928 mol) in acetonitrile (20 ml) was heated in a sealed tube at 100° C. for 2 days, then the suspension was filtered over celite and the filtrate was evaporated under reduced pressure. The residue was purified by short open column chromatography (eluent: DCM/MeOH 99/1). The product fractions were collected and the solvent was evaporated, yielding 0.4794 g of compound 159. A part of the residue was converted into the ethanedioate salt which was collected, washed with cold Et2O and dried in vacuo, yielding the corresponding ethanedioate salt, compound 160.

b) Preparation of Compound 147

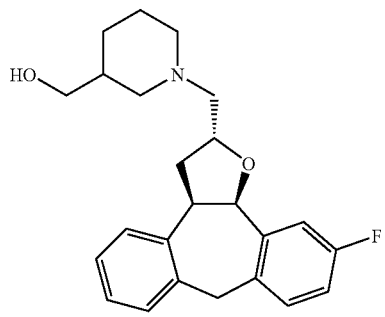

[2R-(2α,3aα,12bβ)]-(3'RS)
(1:1) mixture of diastereoisomers
•C₂H₂O₄ (1:1)

A mixture of compound 159 (0.000909 mol) in Et2O (20 ml) was stirred under N2 at −20° C. and LiAlH4 1M in THF (0.00136 mol) was added dropwise, then the reaction mixture was gradually warmed to room temperature and stirred for 1 hour. An aqueous 10% NH4Cl solution was added dropwise and the resulting mixture was filtered over a celite pad. The organic layer was separated, washed with water and with brine, dried (Na2SO4), filtered off and the solvent was evaporated under reduced pressure. The residue was purified by short open column chromatography over silica gel (eluent: DCM/MeOH 97/3). The product fractions were collected and the solvent was evaporated. The residue was converted into the ethanedioate salt which was collected, washed with cold Et2O and dried in vacuo, yielding 0.363 g (80.5%, mixture of two diastereoisomers) of compound 147.

EXAMPLE B 16 a) Preparation of Compounds 134 and 135

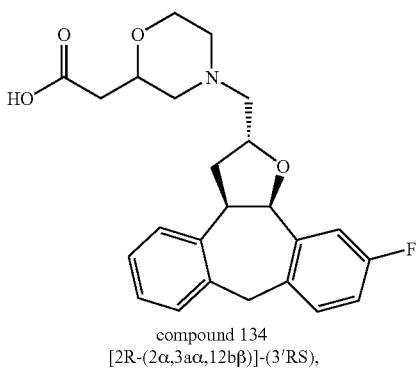

compound 134
[2R-(2α,3aα,12bβ)]-(3'RS),
(1:1) mixture of diastereoisomers
C₂H₂O₄ (1:1)
and

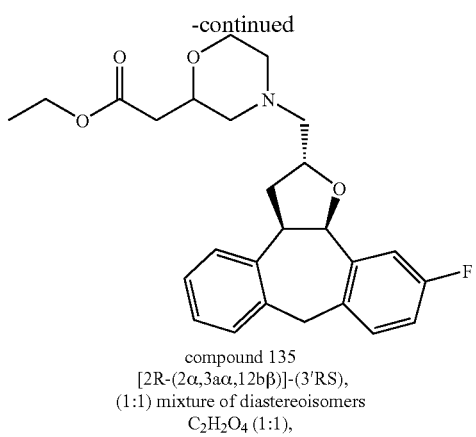

compound 135
[2R-(2α,3aα,12bβ)]-(3'RS),
(1:1) mixture of diastereoisomers
C₂H₂O₄ (1:1), A mixture of intermediate 5 (0.0055 mol) and 2-methyl-2-propanol, potassium salt (0.006 mol) in THF (10 ml) was stirred at −50° C. for 2 hours and then the reaction mixture was partitioned between DCM/water. The aqueous layer was extracted several times with DCM; the organic layers were combined, washed with brine, dried (Na₂SO₄), filtered off and the solvent was evaporated under reduced pressure. The residue was purified by short open column chromatography over silica gel (eluent 1: DCM/MeOH 99/1; eluent 2: DCM/MeOH 95/5). Two product fractions were collected and the solvents were evaporated. The two fractions were each converted into its ethanedioate salt; the resulting precipitates were each filtered off, washed and dried, yielding respectively compound 135 and compound 134.

b) Preparation of Compound 136

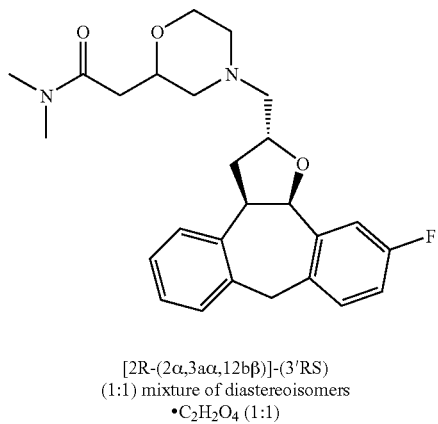 [SMILES: CN(C)C(=O)CC1CN(C[C@H]2C[C@@H]3c4ccccc4Cc4ccc(F)cc4[C@@H]3O2)CCO1]

[2R-(2α,3aα,12bβ)]-(3'RS)
(1:1) mixture of diastereoisomers
•C₂H₂O₄ (1:1)

A mixture of the free base of compound 134 (0.00062 mol), N,N-dimethylamine (0.00003 mol), 1-hydroxy-1H-benzotriazole (0.0010 mol) and N,N'-methanetetrayl-biscyclohexanamine (0.0010 mol) in DMF (5 ml) was stirred at room temperature for 16 hours, then the reaction mixture was partitioned between water/DCM and the aqueous layer was extracted several times with DCM. The organic layers were combined, extracted with NaHCO₃ and with brine, dried (Na₂SO₄), filtered off and the solvent was evaporated under reduced pressure. The residue was purified by short open column chromatography over silica gel (eluent: DCM/(MeOH/NH₃) 93/7). The product fractions were collected and the solvent was evaporated. The residue was converted into the ethanedioate salt; the resulting precipitate was collected, washed with cold Et₂O, and dried, yielding 0.055 g of compound 136.

c) Preparation of Compound 139

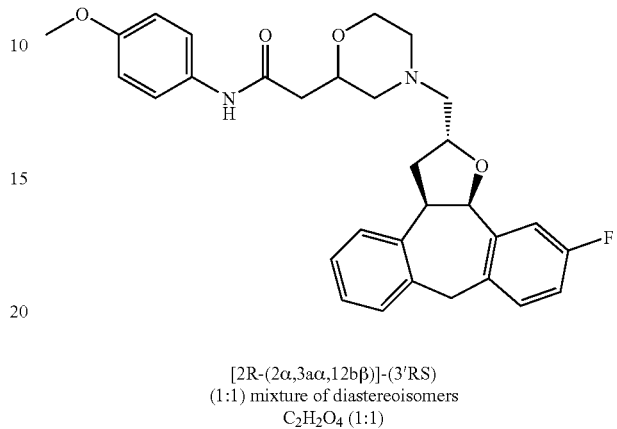

[2R-(2α,3aα,12bβ)]-(3'RS)
(1:1) mixture of diastereoisomers
C₂H₂O₄ (1:1)

A mixture of the free base of compound 134 (0.00085 mol), 4-methoxy-benzenamine (0.00127 mol), 1-hydroxy-1H-benzotriazole (0.00127 mol) and N,N'-methanetetrayl-biscyclohexanamine (0.00127 mol) in DMF (5 ml)) was stirred at room temperature for 16 hours, then the reaction mixture was partitioned between water/DCM and the aqueous layer was extracted several times with DCM. The organic layers were combined, extracted with aqueous NaHCO₃ and with brine, dried (Na₂SO₄), filtered off and the solvent was evaporated under reduced pressure. The residue was purified by short open column chromatography over silica gel (eluent: DCM/(MeOH/NH₃) 93/7). The product fractions were collected and the solvent was evaporated. The residue was converted into the ethanedioate salt; the resulting precipitate was collected and dried, yielding 0.025 g of compound 139.

d) Preparation of Compound 129

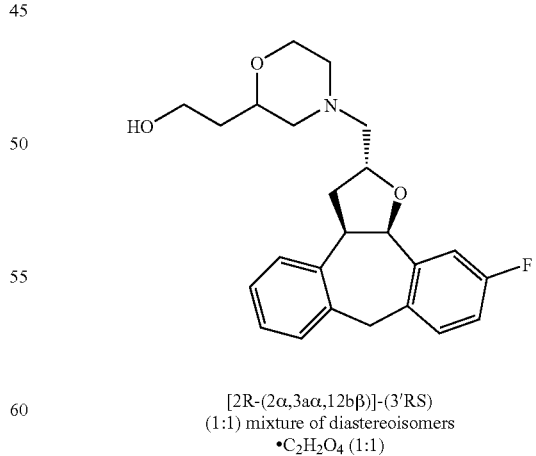

[2R-(2α,3aα,12bβ)]-(3'RS)
(1:1) mixture of diastereoisomers
•C₂H₂O₄ (1:1)

A mixture of compound 135 (0.00296 mol) and lithium aluminum hydride (0.003 mol) in THF (10 ml) was stirred at room temperature for 3 hours and then the reaction mixture was partitioned between DCM/water. The aqueous layer was extracted several times with DCM; the organic layers were combined, extracted with aqueous sodium hydroxide (1N), washed with brine, dried (Na₂SO₄), filtered off and the solvent was evaporated under reduced pressure, yielding 11 g (93%) of free base of compound 129. A small amount of this residue was converted into the ethanedioate salt by treatment with oxalic acid in Et₂O; the resulting precipitate was filtered off, washed with cold Et₂O and dried in vacio, yielding compound 129.

e) Preparation of Compound 138

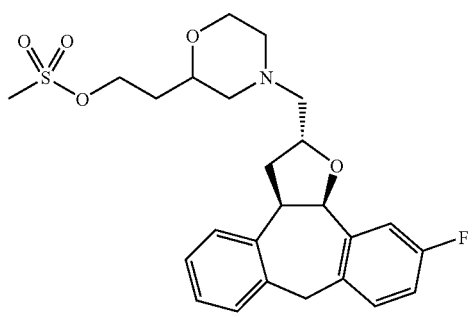

[2R-(2α,3aα,12bβ)]-(3'RS)
(1:1) mixture of diastereoisomers

A mixture of the free base of compound 129 (0.00277 mol), methanesulfonyl chloride (0.00305 mol), triethylamine (0.004155 mol) and N,N-dimethyl-4-pyridinamine (0.000277 mol) in DCM (15 ml) was stirred at room temperature for 16 hours and then the reaction mixture was partitioned between DCM/water. The aqueous layer was extracted several times with DCM; the organic layers were combined, washed with NaHCO₃ and with brine, dried (Na₂SO₄), filtered off and the solvent was evaporated under reduced pressure. The residue was purified by short open column chromatography over silica gel (eluent: DCM/MeOH 95/5). The product fractions were collected and the solvent was evaporated, yielding 0.8 g (61%) of compound 138.

f) Preparation of Compound 130

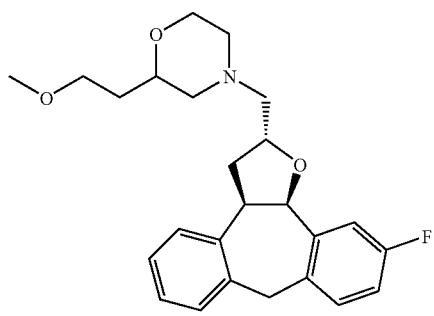

[2R-(2α,3aα,12bβ)]-(3'RS)
(1:1) mixture of diastereoisomers
C₂H₂O₄ (1:1)

A mixture of compound 138 (0.0002 mol) and NaOCH₃/MeOH (3 ml) in MeOH (10 ml) was stirred under microwave conditions at 130° C. for 50 min. and the resulting solution was concentrated under reduced pressure. The residue was dissolved in DCM; the organic layer was separated, washed with water and with brine, dried (Na₂SO₄), filtered off and the solvent was evaporated. The residue was purified by short open column chromatography over silica gel (eluent: DCM/(MeOH/NH₃) 98/2). The product fractions were collected and the solvent was evaporated. The residual oil was converted into the ethanedioate salt by treatment with oxalic acid in Et₂O; the resulting precipitate was filtered off, washed with cold Et₂O and dried, yielding 0.020 g of compound 130.

g) Preparation of Compound 132

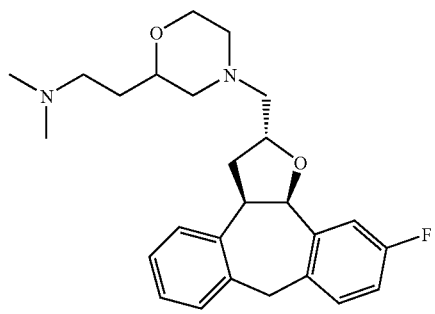

[2R-(2α,3aα,12bβ)]-(3'RS)
(1:1) mixture of diastereoisomers
•C₂H₂O₄ (1:1)

A mixture of compound 138 (0.00023 mol), N-,N-dimethylamine (0.0023 mol, 2.0 M in THF) and calcium oxide (0.0023 mol) in THF (10 ml) was stirred in a sealed tube at 120° C. (oil bath temperature) for 16 hours and then the reaction mixture was cooled to room temperature and filtered through a celite pad. The filtrate was evaporated under reduced pressure and the residue was purified by short open column chromatography over silica gel (eluent: DCM/(MeOH/NH₃) 99/1). The product fractions were collected and the solvent was evaporated. The residual oil was converted into the ethanedioate salt; the resulting precipitate was filtered off, washed with Et$_2$O and dried, yielding 0.060 g compound 132.

h) Preparation of Compound 131

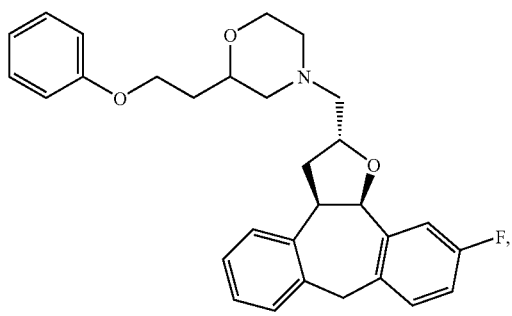

[2R-(2α,3aα,12bβ)]-(3′RS)
(1:1) mixture of diastereoisomers
C$_2$H$_2$O$_4$ (1:1)

A mixture of compound 138 (0.000147 mol) and phenol, sodium salt, trihydrate (0.000441 mol) in DMF (5 ml) was stirred at 180° C. for 50 min. under microwave conditions and then the solvent was evaporated under N$_2$ at 50° C. The residue was dissolved in DCM, washed with water and with brine, then dried (Na$_2$SO$_4$) and filtered off. The solvent was evaporated and the residue was purified by short open column chromatography over silica gel (eluent: DCM/(MeOH/NH$_3$) 97/3). The product fractions were collected and the solvent was evaporated. The residue was converted into the ethanedioate salt; the resulting precipitate was collected, washed with cold Et$_2$O and dried, yielding compound 131.

EXAMPLE B17

Preparation of Compound 4

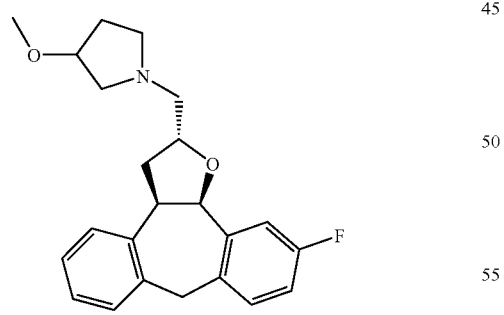

[2R-(2α,3aα,12bβ)]-(3′RS)
(1:1) mixture of diastereoisomers
C$_2$H$_2$O$_4$ (1:1)

The free base of compound 1 (0.00028 mol) was added portionwise at 0° C. to an ice-cold mixture of sodium hydride (60% in mineral oil, 0.00056 mol) in 1,2-dimethoxy-ethane (5 ml) and the reaction mixture was stirred for 20 min. at 0° C. Iodomethane (0.00056 mol) was added and the reaction mixture was stirred for 24 hours at room temperature. A saturated aqueous NaHCO$_3$ solution was added and the mixture was extracted with DCM. The organic layer was separated, dried (Na$_2$SO$_4$) and the solvent was evaporated. The residue was purified by short open column chromatography (eluent: DCM/EtOAc 1/1, 0/1). The product fractions were collected and the solvent was evaporated. The residue was converted into the ethanedioate salt with Et$_2$O. The resulting precipitate was filtered off, washed with cold Et$_2$O and dried, yielding 0.0298 g (29%) of compound 4.

EXAMPLE B18

Preparation of Compound 98

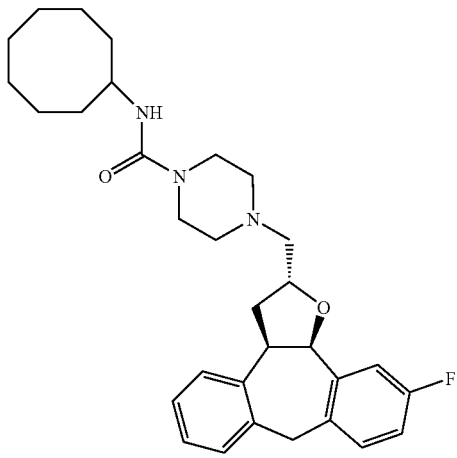

[2R-(2α,3aα,12bβ)]
•C$_2$H$_2$O$_4$ (1:1)

DCM (5 ml) was added to resin intermediate 6 (0.000215 mol), the mixture was stirred for 30 minutes and filtered off. DCM (10 ml) was added to the washed filter residue, then an excess of cyclooctanamine (0.00215 mol) was added and the reaction mixture was stirred overnight. The resin was washed automatically with DCM (5×5 ml), with THF (5×5 ml), with MeOH (5×5 ml), with DCM (1×5 ml) and with acetonitrile (1×5 ml). Dry acetonitrile (10 ml) and intermediate 3 (0.0002365 mol) were added, then triethylamine (0.00086 mol) was added and the reaction mixture was stirred for 20 hours at 60° C., then filtered off. The residue was dissolved in Et$_2$O/EtOH (7/2) and converted into the ethanedioate salt.

The precipitate was filtered off, then washed with cold Et$_2$O and dried in vacuo, yielding compound 98.

EXAMPLE B19 a) Preparation of Compound 11

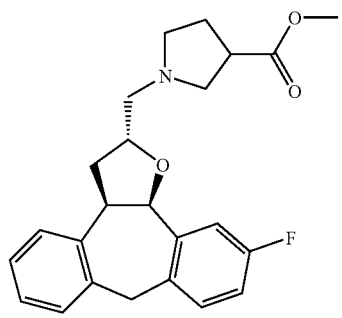

[2R-(2α,3aα,12bβ)]-(3'RS)
(1:1) mixture of diastereoisomers
•C$_2$H$_2$O$_4$ (1:1)

A mixture of intermediate 1 (0.001 mol), 3-pyrrolidinecarboxylic acid, methyl ester (0.003 mol) and calcium oxide (0.100 g) in acetonitrile (10 ml) was heated in a microwave oven for 30 minutes at 130° C., then at 160° C. for 30 minutes. The solids were filtered off and the solvent was evaporated. The residue was purified by short open column chromatography over silica gel (eluent 1: DCM/EtOAc 1/1, 0/1; eluent 2: DCM/MeOH 96/4). The product fractions were collected and the solvent was evaporated, yielding 0.215 g (54%) of free base of compound 11.

A part (0.100 g) of the residue was separated and converted into the ethanedioate salt in EtOH. The solvent was evaporated and the residue was washed with cold Et$_2$O, then dried, yielding: 0.1065 g of compound 11.

b) Preparation of Compound 10

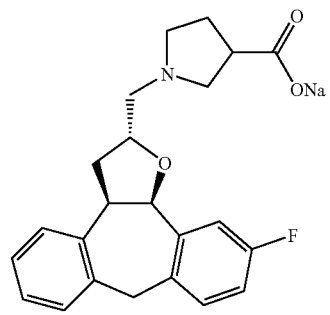

[2R-(2α,3aα,12bβ)]-(3'RS)
(1:1) mixture of diastereoisomers
•Na

A mixture of sodium hydroxide (0.00031 mol) in water (0.5 ml) was added to a solution of free base of compound 11 (0.00028 mol) in dioxane (5 ml) and the reaction mixture was stirred at room temperature for 24 hours. The solids were filtered off and the solvent was evaporated. The residue was washed with Et$_2$O and dried, yielding 0.0735 g (69%) of compound 10.

EXAMPLE B20 a) Preparation of Compound 5

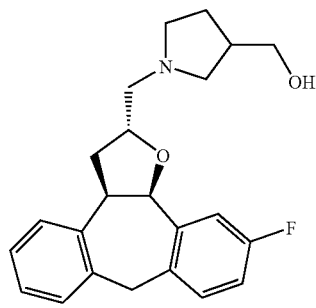

[2R-(2α,3aα,12bβ)]-(3'RS)
(1:1) mixture of diastereoisomers

Lithium aluminium hydride (0.00013 mol) was added to a solution of free base of compound 11 (0.00013 mol) in dry THF (1 ml) under a nitrogen atmosphere and the reaction mixture was stirred for 3 hours at room temperature. An aqueous saturated NH$_4$Cl solution (cat. quant., few drops) was added until the generation of gas stopped. DCM was added. Layers were separated and the organic one was dried (Na$_2$SO$_4$) and and the solvent was evaporated. The residue was purified by short open column chromatography (eluent 1: DCM/MeOH 95/5; eluent 2: DCM/(MeOH/NH$_3$) 95/5). The product fractions were collected and the solvent was evaporated. The residue was treated with DIPE to give a solid that was dried in vacuo, yielding 0.0196 g (41%) of compound 5.

b) Preparation of Compound 25

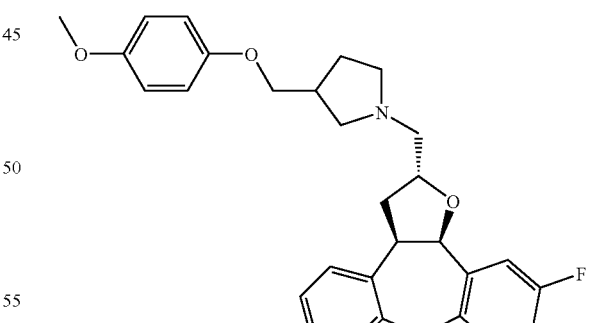

[2R-(2α,3aα,12bβ)]-(3'RS)
(1:1) mixture of diastereoisomers

A mixture of compound 5 (0.000136 mol), 4-methoxyphenol (0.00027 mol), diazenedicarboxylic acid, diethyl ester (0.00027 mol) and triphenylphosphine (0.00027 mol) in THF (q.s.) was stirred for 30 minutes in a microwave oven at 90° C. The solvent was evaporated and the residue was dissolved in MeOH (5 ml). Amberlyst 15 (0.00054 mol) was added to the solution, the resulting mixture was shaken 48 hours at room temperature and filtered off. The resin was washed 3 times with MeOH (the MeOH extracts were discarded), then MeOH/NH₃ (3 ml) was added to the resin. The mixture was shaken for 4.5 hours at room temperature and filtered off. The resin was washed 3 times with MeOH/NH₃ and the filtrates were combined and evaporated. The residue was purified by short open column chromatography (eluent 1: DCM/EtOAc 1/1; eluent 2: DCM/MeOH 96/4). The product fractions were collected and the solvent was evaporated, yielding 0.0097 g (15%) of compound 25.

EXAMPLE B21 a) Preparation of Compound 271

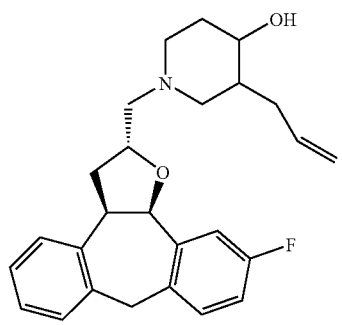

[2R-(2α,3aα,12bβ)]-(3'RS,4'RS)

A solution of intermediate 8 (0.015 mol) in dioxane (10 ml) and acetonitrile (10 ml) was diluted with THF (100 ml), then intermediate 1 (0.005 mol) and calcium oxide (0.15 mol) were added and the reaction mixture was heated for 16 hours at 140° C. The suspension was filtered over celite and the filtrate was evaporated under reduced pressure. The residue was purified by short open column chromatography over silica gel (eluent: DCM/(MeOH/NH₃)(saturated) 97/3). The product fractions were collected and the solvent was evaporated, yielding 0.153 g of compound 271.

b) Preparation of Compound 279

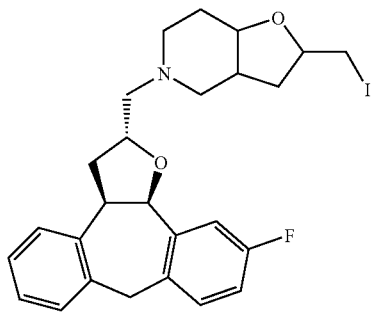

[2R-(2α,3aα,12bβ)]-(2'RS,3a'RS,7a'RS)
mixture of diastereoisomers

Bis(pyridine)iodonium tetrafluoroborate (0.001717 mol) was added to a mixture of compound 271 (0.001717 mol) in DCM (q.s.) at room temperature under N₂. The reaction mixture was stirred for 1 hour and then a Na₂S₂O₃ solution was added. The organic layer was separated, dried (MgSO₄), filtered off and the solvent was evaporated under reduced pressure. The residue was purified by short open column chromatography over silica gel (eluent: EtOAc/Heptane 2/4). The product fractions were collected and the solvent was evaporated, yielding 0.320 g of compound 279 (used as such in the next reaction step without further purification).

c) Preparation of Compound 274

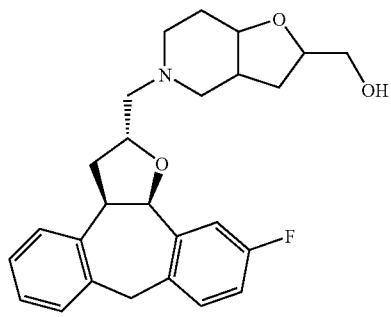

[2R-(2α,3aα,12bβ)]-(2'RS,3a'RS,7a'RS)
mixture of diastereoisomers
C₂H₂O₄ (1:1)

A mixture of compound 279 (0.0006 mol) and CH₃ONa/MeOH 30% (0.006 mol) in MeOH (5 ml) was irradiated under microwave conditions at 100° C. for 20 min. The solvent was evaporated and the residue was converted into the ethanedioate salt. The resulting precipitate was collected and dried, yielding 0.100 g of compound 274.

EXAMPLE B22 a) Preparation of Compound 258

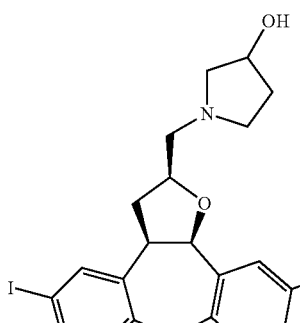

[2RS-(2β,3aα,12bβ)]-(3'RS)

A mixture of intermediate 9 (0.00186 mol), 3-pyrrolidinol (0.0186 mol) and calcium oxide (0.186 mol) in THF (25 ml) was stirred for 16 hours at 120° C. and then the resulting suspension was filtered over celite. The filtrate was evaporated under reduced pressure and the residue was dissolved in DCM. The solution was washed with an aqueous saturated solution of NaHCO$_3$, with water and with brine. The organic layer was dried (Na$_2$SO$_4$), filtered off and the solvent was evaporated. The residue was pre-purified by short open column chromatography over silica gel and the product fractions were collected. The solvent was evaporated and the residue was purified by radial chromatography on silica gel (eluent: DCM). The pure fractions were collected and the solvent was evaporated, yielding 0.480 g of compound 258.

b) Preparation of Compound 260

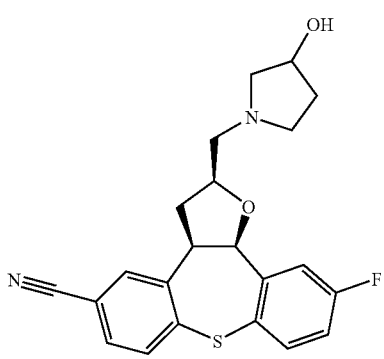

C$_2$H$_2$O$_4$ (1:1),[2S*-(2β,3aα,12bβ)]-(3'RS)

Compound 258 (0.00014 mol), zinc cyanide (0.00009 mol) and tetrakis(triphenylphosphine)-palladium (0.000014 mol) were added at room temperature to DMF (10 ml, previously deoxygenated) and the reaction mixture was heated at 120° C. (from room temperature to 120° C. in 5 min.) for 15 minutes under microwave conditions. The mixture was filtered and the organic solvent (DMF) was evaporated. The residue was purified by short open column chromatography over silica gel (eluent: DCM/(MeOH/NH$_3$) 95/5). The product fractions were collected and the solvent was evaporated. The residue was converted into the ethanedioate salt and the resulting solids were collected, washed with cold Et$_2$O, and dried in vacuo yielding compound 260.

EXAMPLE B23

Preparation of Compound 218

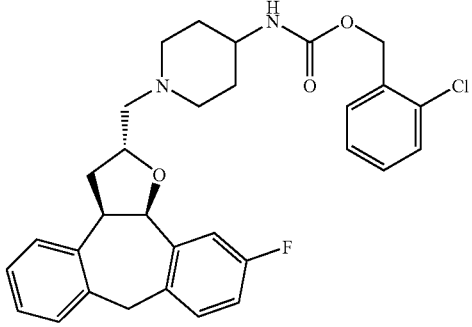

[2R-(2α,3aα,12bβ)]
C$_2$HF$_3$O$_2$ (1:1)

Intermediate 10 was dissolved in DCM and 2-chlorobenzyl chloroformate (1.1 eq) was added. Polymer supported DIPEA (Aldrich, ref 53,873-6; 100-200 mesh; loading 2.0-3.5 mmol/g, 2.5 eq) was added and the vial was shaken overnight. Polymer supported Trisamine (Aldrich, ref 47,210-7; 200-400 mesh; loading 4.2 mmol/g, 3 eq) was added and the mixture was shaken for 3 hours. The solids were filtered off and the filtrate was concentrated, affording either a pure compound or a mixture that was purified by short open column chromatography. The pure compound was converted into the corresponding trifluoroacetate salt by treatment with trifluoroacetic acid in DCM, volatiles were evaporated in vacuo yielding compound 218.

EXAMPLE B24

Preparation of Compound 244

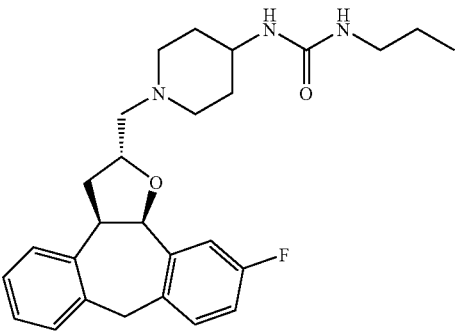

[2R-(2α,3aα,12bβ)]
C$_2$HF$_3$O$_2$ (1:1)

Intermediate 10 was dissolved in DCM and propylisocyanatee (1.1 eq) was added. The vial was shaken overnight. Polymer supported Trisamine (Aldrich, ref 47,210-7; 200-

400 mesh; loading 4.2 mmol/g, 3 eq) was added and the mixture was shaken for 3 hours. Solids were filtered off and the filtrate was concentrated affording either pure compound or a mixture that was purified by short open column chromatography. The pure compound were converted into the corresponding trifluoroacetate salts by treatment with trifluoroacetic acid in DCM, volatiles were evaporated in vacuo yielding compound 244.

EXAMPLE B25

Preparation of Compound 108

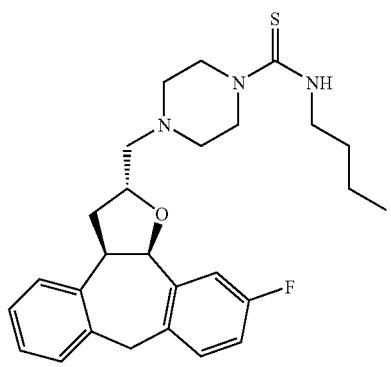

[2R-(2α,3aα,12bβ)]
$C_2H_2O_4$ (1:1)

To a mixture of intermediate 3 (0.000113 mol) in DCM (6 ml) at room temperature, 1-isothiocyanato-butane (0.9 equiv., 0.0001 mol) was added. The mixture was stirred for 1 hour at room temperature. A polymer linked —N═C═O (Aldrich, ref 47,368-5; 200-400 mesh, loading 1.85 mmol/g, 3 equiv.) was added and the mixture was stirred overnight. The mixture was filtered and the solvent was evaporated. The residue was purified by short open column chromatography (eluent: DCM, then DCM/MeOH—$NH_3$ 98/2). The product fractions were collected and the solvent was evaporated affording the corresponding free base, which was transformed into the corresponding oxalate salt by treatment with oxalic acid in $Et_2O$. The formed precipitate was filtered off, washed with cold $Et_2O$ and dried in vacuo yielding compound 108.

EXAMPLE B26

Preparation of Compound 53

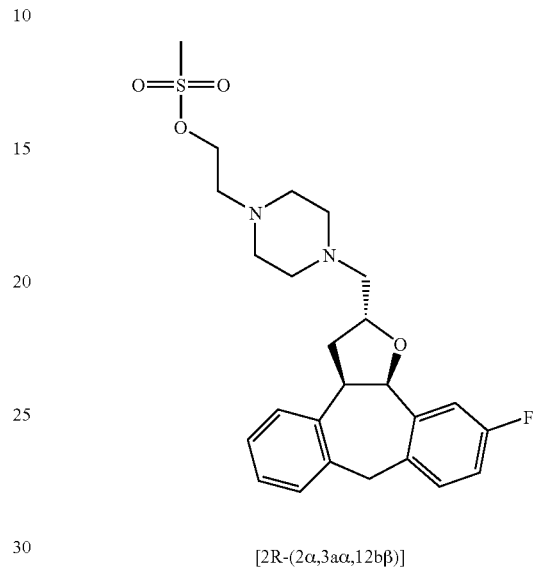

[2R-(2α,3aα,12bβ)]

Methanesulfonyl chloride (0.00225 mol) was added to a solution of intermediate 11 (0.0015 mol) in triethylamine (0.42 ml) and DCM, dry (10 ml), stirred at 0° C. The reaction mixture was stirred for 16 hours at room temperature. Water was added and the mixture was stirred. The organic layer was separated, dried ($Na_2SO_4$), filtered and the solvent evaporated. The residue was purified by short open column chromatography over silica gel (eluent: DCM/MeOH 98/8). The product fractions were collected and the solvent was evaporated, yielding 0.390 g of compound 53.

The final compounds prepared hereinunder all are mixtures of isomeric forms, unless otherwise specified.

TABLE 1

| Co. No | Ex. No | X | $R^3$ | Physical data |
|---|---|---|---|---|
| 1 | B1 | —$CH_2$— | 3′----OH | $C_2H_2O_4$ (1:1), [2R-(2α,3aα,12bβ)]-(3′RS), (1:1) mixture of diastereoisomers |

TABLE 1-continued

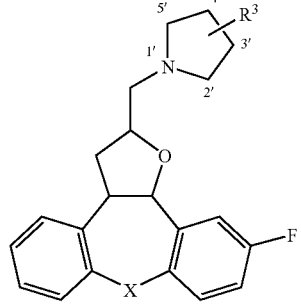

| Co. No | Ex. No. | X | R³ | Physical data |
|---|---|---|---|---|
| 2 | B1 | —CH$_2$— | 3'----OH | C$_2$H$_2$O$_4$ (1:1), [2R-(2α,3aα,12bβ)]-(3'R)] |
| 3 | B1 | —CH$_2$— | 3'----OH | C$_2$H$_2$O$_4$ (1:1), [2R-(2α,3aα,12bβ)]-(3'S) |
| 4 | B17 | —CH$_2$— | 3'----O-CH$_3$ | C$_2$H$_2$O$_4$ (1:1), [2R-(2α,3aα,12bβ)]-(3'RS), (1:1) mixture of diastereoisomers |
| 5 | B20 | —CH$_2$— | 3'----CH$_2$OH | [2R-(2α,3aα,12bβ)]-(3'RS), (1:1) mixture of diastereoisomers |
| 6 | B1 | —CH$_2$— | 3'----CH$_2$CH$_2$OH | C$_2$H$_2$O$_4$ (1:1), [2R-(2α,3aα,12bβ)]-(3'RS), (1:1) mixture of diastereoisomers |
| 7 | B12 | —CH$_2$— | 3'=O | [2R-(2α,3aα,12bβ)] |
| 8 | B1 | —CH$_2$— | 3'----N(CH$_3$)$_2$ | [2R-(2α,3aα,12bβ)]-(3'RS), (1:1) mixture of diastereoisomers |
| 9 | B1 | —CH$_2$— | 3'----CH$_2$N(CH$_3$)$_2$ | C$_2$H$_2$O$_4$ (1:1), [2R-(2α,3aα,12bβ)]-(3'RS), (1:1) mixture of diastereoisomers |
| 10 | B19 | —CH$_2$— | 3'----C(=O)ONa | •Na [2R-(2α,3aα,12bβ)]-(3'RS), (1:1) mixture of diastereoisomers |
| 11 | B19 | —CH$_2$— | 3'----C(=O)OCH$_3$ | C$_2$H$_2$O$_4$ (1:1), [2R-(2α,3aα,12bβ)]-(3'RS), (1:1) mixture of diastereoisomers |
| 12 | B8 | —CH$_2$— | 3'----OC(=O)CH$_3$ | C$_2$H$_2$O$_4$ (1:1), [2R-(2α,3aα,12bβ)]-(3'RS), (1:1) mixture of diastereoisomers |
| 13 | B8 | —CH$_2$— | 3'----OC(=O)-cyclopropyl | C$_2$H$_2$O$_4$ (1:1), [2R-(2α,3aα,12bβ)]-(3'RS), (1:1) mixture of diastereoisomers |
| 14 | B8 | —CH$_2$— | 3'----OC(=O)-cyclopentyl | C$_2$H$_2$O$_4$ (1:1), [2R-(2α,3aα,12bβ)]-(3'RS), (1:1) mixture of diastereoisomers |

TABLE 1-continued

| Co. No | Ex. No | X | R³ | Physical data |
|---|---|---|---|---|
| 15 | B8 | —CH₂— | 4-methylbenzoate (3'-O-C(=O)-C₆H₄-CH₃) | C₂H₂O₄ (1:1), [2R-(2α,3aα,12bβ)]-(3'RS), (1:1) mixture of diastereoisomers |
| 16 | B8 | —CH₂— | 4-fluorobenzoate (3'-O-C(=O)-C₆H₄-F) | C₂H₂O₄ (1:1), [2R-(2α,3aα,12bβ)]-(3'RS), (1:1) mixture of diastereoisomers |
| 17 | B8 | —CH₂— | 2,4-difluorobenzoate | C₂H₂O₄ (1:1), [2R-(2α,3aα,12bβ)]-(3'RS), (1:1) mixture of diastereoisomers |
| 18 | B8 | —CH₂— | phenylacetate (3'-O-C(=O)-CH₂-C₆H₅) | C₂H₂O₄ (1:1), [2R-(2α,3aα,12bβ)]-(3'RS), (1:1) mixture of diastereoisomers |
| 19 | B8 | —CH₂— | ethyl carbonate (3'-CH₂-O-C(=O)-O-CH₂CH₃) | C₂H₂O₄ (1:1), [2R-(2α,3aα,12bβ)]-(3'RS), (1:1) mixture of diastereoisomers |
| 20 | B9 | —CH₂— | ethylcarbamate (3'-CH₂-O-C(=O)-NH-CH₂CH₃) | [2R-(2α,3aα,12bβ)]-(3'RS), (1:1) mixture of diastereoisomers |
| 21 | B9 | —CH₂— | cyclohexylcarbamate | [2R-(2α,3aα,12bβ)]-(3'RS), (1:1) mixture of diastereoisomers |
| 22 | B9 | —CH₂— | phenylcarbamate | [2R-(2α,3aα,12bβ)]-(3'RS), (1:1) mixture of diastereoisomers |
| 23 | B9 | —CH₂— | 4-fluorophenylcarbamate | [2R-(2α,3aα,12bβ)]-(3'RS), (1:1) mixture of diastereoisomers |

TABLE 1-continued

| Co. No | Ex. No | X | R³ | Physical data |
|---|---|---|---|---|
| 24 | B9 | —CH₂— | 3'-O-C(=O)-NH-CH₂-phenyl (benzyl carbamate) | [2R-(2α,3aα,12bβ)]-(3'RS), (1:1) mixture of diastereoisomers |
| 25 | B20 | —CH₂— | 3'-O-CH₂-(4-methoxyphenyl) | [2R-(2α,3aα,12bβ)]-(3'RS), (1:1) mixture of diastereoisomers |
| 26 | B20 | —CH₂— | 3'-O-CH₂-(4-fluorophenyl) | [2R-(2α,3aα,12bβ)]-(3'RS), (1:1) mixture of diastereoisomers |
| 27 | B20 | —CH₂— | 3'-O-CH₂-(3-fluorophenyl) | [2R-(2α,3aα,12bβ)]-(3'RS), (1:1) mixture of diastereoisomers |
| 28 | B20 | —CH₂— | 3'-O-(4-methylphenyl) | C₂H₂O₄ (1:1), [2R-(2α,3aα,12bβ)]-(3'RS), (1:1) mixture of diastereoisomers |
| 29 | B20 | —CH₂— | 3'-O-(3-cyanophenyl) | C₂H₂O₄ (1:1), [2R-(2α,3aα,12bβ)]-(3'RS), (1:1) mixture of diastereoisomers |
| 30 | B20 | —CH₂— | 3'-O-(4-(methoxycarbonyl)phenyl) | C₂H₂O₄ (1:1), [2R-(2α,3aα,12bβ)]-(3'RS), (1:1) mixture of diastereoisomers |
| 31 | B20 | —CH₂— | 3'-O-(3-methoxyphenyl) | C₂H₂O₄ (1:1), [2R-(2α,3aα,12bβ)]-(3'RS), (1:1) mixture of diastereoisomers |
| 32 | B20 | —CH₂— | 3'-O-(2-methoxyphenyl) | C₂H₂O₄ (1:1), [2R-(2α,3aα,12bβ)]-(3'RS), (1:1) mixture of diastereoisomers |

TABLE 1-continued

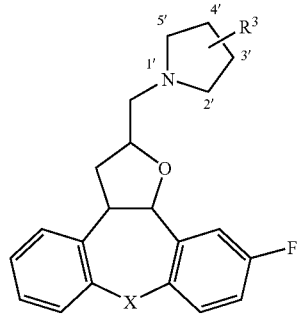

| Co. No | Ex. No | X | R³ | Physical data |
|---|---|---|---|---|
| 33 | B20 | —CH₂— | 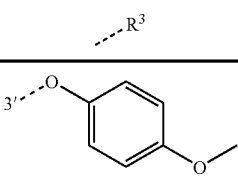 3'—O—C₆H₄—OMe (para) | C₂H₂O₄ (1:1), [2R-(2α,3aα,12bβ)]-(3'RS), (1:1) mixture of diastereoisomers |
| 34 | B20 | —CH₂— | 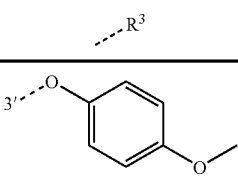 3'—O—C₆H₄—F (ortho) | C₂H₂O₄ (1:1), [2R-(2α,3aα,12bβ)]-(3'RS), (1:1) mixture of diastereoisomers |
| 35 | B20 | —CH₂— | 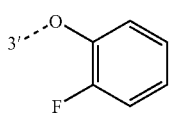 3'—O—C₆H₄—F (meta) | C₂H₂O₄ (1:1), [2R-(2α,3aα,12bβ)]-(3'RS), (1:1) mixture of diastereoisomers |
| 36 | B20 | —CH₂— | 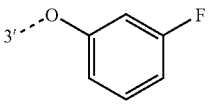 3'—O—C₆H₄—F (para) | C₂H₂O₄ (1:1), [2R-(2α,3aα,12bβ)]-(3'RS), (1:1) mixture of diastereoisomers |
| 37 | B20 | —CH₂— | 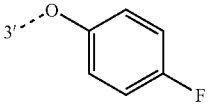 3'—O—C₆H₄—CF₃ (meta) | C₂H₂O₄ (1:1), [2R-(2α,3aα,12bβ)]-(3'RS), (1:1) mixture of diastereoisomers |
| 38 | B1 | —CH₂— | 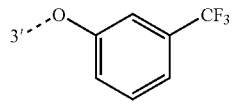 2'—OMe | C₂H₂O₄ (1:1), [2R-(2α,3aα,12bβ)]-(2'RS), (1:1) mixture of diastereoisomers |
| 39 | B12 | —CH₂— | 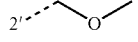 3'-C(OH)(CH₃) | C₂H₂O₄ (1:1), [2R-(2α,3aα,12bβ)]-(3'RS), (1:1) mixture of diastereoisomers |
| 40 | B12 | —CH₂— |  3'-C(OH)(CH=CH₂) | C₂H₂O₄ (1:1); [2R-(2α,3aα,12bβ)]-(3'RS), (1:1) mixture of diastereoisomers |
| 41 | B12 | —CH₂— | 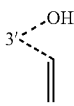 3'-C(OH)(C₆H₄-F) | C₂H₂O₄ (1:1), [2R-(2α,3aα,12bβ)]-(3'RS), (1:1) mixture of diastereoisomers |
| 42 | B1 | —S— | 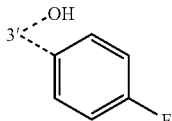 3'—OH | [2RS-(2β,3aα,12bβ)]-(3'RS) |
| 43 | B1 | —S— |  3'—OH | C₂H₂O₄ (1:1), [2RS-(2β,3aα,12bβ)]-(3'RS) |
| 44 | B1 | —S— |  3'—OH | C₂H₂O₄ (1:1), [2RS-(2β,3aα,12bβ)]-(3'RS) + [2RS-(2α,3aα,12bβ)]-(3'RS), 60:40 mixture of diastereoisomers |

TABLE 1-continued

[Structure: tricyclic system with X bridge, fused furan ring bearing CH2-pyrrolidine (positions 1'-5') with R3 substituent at 3', and fluorine on aromatic ring]

| Co. No | Ex. No | X | R3 | Physical data |
|---|---|---|---|---|
| 45 | B1 | —CH(CH3)— | 3'-····OH | C2H2O4 (1:1), [2R-(2α,3aα,8α,12bβ)]-(3'RS), (1:1) mixture of diastereoisomers |
| 46 | B1 | —CH(CH3)— | 3'-····OH | C2H2O4 (1:1), [2R-(2α,3aα,8β,12bβ)]-(3'RS), (1:1) mixture of diastereoisomers |

TABLE 2

[Structure: tricyclic system with CH2 bridge, fused furan ring bearing CH2-piperazine with R4 substituent on distal N, and fluorine on aromatic ring]

| Co. No | Ex. No | R4 | Physical data |
|---|---|---|---|
| 47 | B1 | —CH2CH2NH2 | C2H2O4 (1:1), [2R-(2α,3aα,12bβ)] |
| 48 | B13 | —CH2—CH=CH—C6H5 (E) | C2HF3O2 (1:1)-(E)-[2R-(2α,3aα,12bβ)] |
| 49 | B13 | —CH2—C(CH3)=CH—C6H5 (E) | C2HF3O2 (1:1)-(E)-[2R-(2α,3aα,12bβ)] |
| 50 | B13 | —CH2—C(=CH—C6H5)—CH2CH2CH2CH3 | C2HF3O2 (1:1), [2R-(2α,3aα,12bβ)] |

TABLE 2-continued
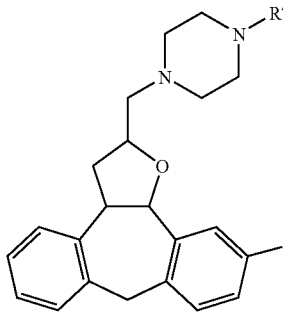
| Co. No | Ex. No. | ----R⁴ | Physical data |
|---|---|---|---|
| 51 | B10 | 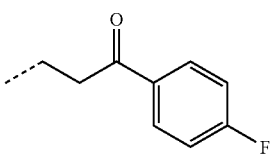 | [2R-(2α,3aα,12bβ)] |
| 52 | B10 | 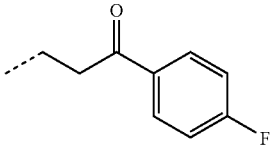 | $C_2H_2O_4$ (1:1), [2R-(2α,3aα,12bβ)] |
| 53 | B26 | 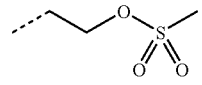 | [2R-(2α,3aα,12bβ)] |
| 54 | B1 | 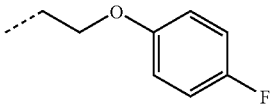 | $C_2H_2O_4$ (1:1), [2R-(2α,3aα,12bβ)] |
| 55 | B14 | 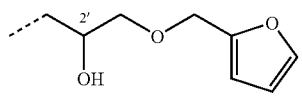 | $C_2H_2O_4$ (1:2), [2R-(2α,3aα,12bβ)]-(2'RS)-(1:1) mixture of diastereoisomers |
| 56 | B14 | 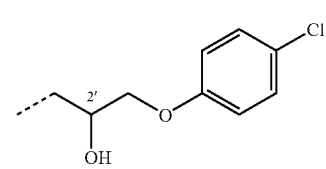 | $C_2H_2O_4$ (1:2), [2R-(2α,3aα,12bβ)]-(2'RS)-(1:1) mixture of diastereoisomers |
| 57 | B14 | 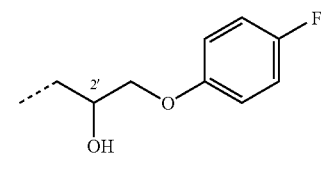 | $C_2H_2O_4$ (1:2), [2R-(2α,3aα,12bβ)]-(2'RS)-(1:1) mixture of diastereoisomers |
| 58 | B13 | 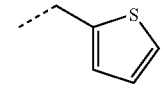 | $C_2HF_3O_2$ (1:1), [2R-(2α,3aα,12bβ)], |
| 59 | B13 | 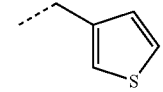 | $C_2HF_3O_2$ (1:1), [2R-(2α,3aα,12bβ)] |

TABLE 2-continued
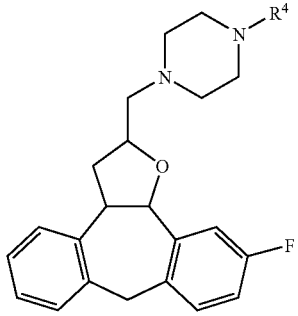
| Co. No | Ex. No | R⁴ | Physical data |
|---|---|---|---|
| 60 | B13 |  | C₂HF₃O₂ (1:1), [2R-(2α,3aα,12bβ)] |
| 61 | B13 | 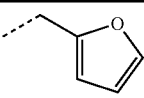 | C₂HF₃O₂ (1:1), [2R-(2α,3aα,12bβ)] |
| 62 | B13 | 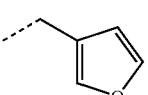 | C₂HF₃O₂ (1:1), [2R-(2α,3aα,12bβ)] |
| 63 | B13 | 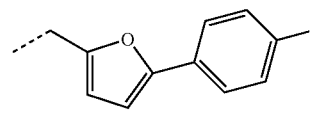 | C₂HF₃O₂ (1:1), [2R-(2α,3aα,12bβ)] |
| 64 | B13 | 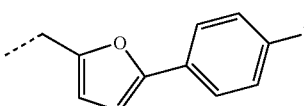 | C₂HF₃O₂ (1:1), [2R-(2α,3aα,12bβ)] |
| 65 | B13 | 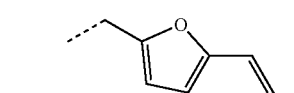 | C₂HF₃O₂ (1:1), [2R-(2α,3aα,12bβ)] |
| 66 | B13 | 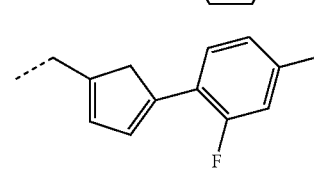 | C₂HF₃O₂ (1:1), [2R-(2α,3aα,12bβ)] |
| 67 | B13 | 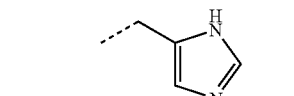 | C₂HF₃O₂ (1:1), [2R-(2α,3aα,12bβ)] |
| 68 | B13 | 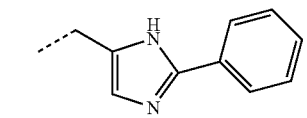 | C₂HF₃O₂ (1:1), [2R-(2α,3aα,12bβ)] |

TABLE 2-continued
| Co. No | Ex. No | ---R⁴ | Physical data |
|---|---|---|---|
| 69 | B13 | 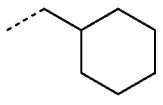 | C₂HF₃O₂ (1:1), [2R-(2α,3aα,12bβ)] |
| 70 | B13 | 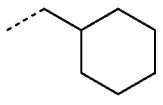 | C₂HF₃O₂ (1:1), [2R-(2α,3aα,12bβ)] |
| 71 | B13 | 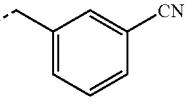 | C₂HF₃O₂ (1:1), [2R-(2α,3aα,12bβ)] |
| 72 | B13 | 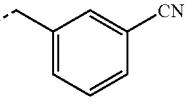 | C₂HF₃O₂ (1:1), [2R-(2α,3aα,12bβ)] |
| 73 | B13 | 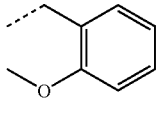 | C₂HF₃O₂ (1:1), [2R-(2α,3aα,12bβ)] |
| 74 | B13 | 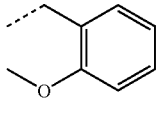 | C₂HF₃O₂ (1:1), [2R-(2α,3aα,12bβ)] |
| 75 | B13 | 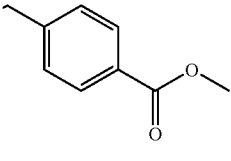 | C₂HF₃O₂ (1:1), [2R-(2α,3aα,12bβ)] |
| 76 | B13 | 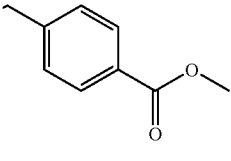 | C₂HF₃O₂ (1:1), [2R-(2α,3aα,12bβ)] |
| 77 | B11 | 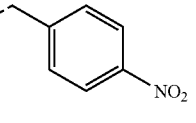 | C₂H₂O₄ (1:1), [2R-(2α,3aα,12bβ)] |
| 78 | B11 | 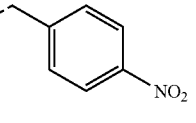 | C₂H₂O₄ (1:1), [2R-(2α,3aα,12bβ)] |

TABLE 2-continued

| Co. No | Ex. No | R⁴ | Physical data |
|---|---|---|---|
| 79 | B11 | cyclopentyl-C(=O)- | $C_2H_2O_4$ (1:1), [2R-(2α,3aα,12bβ)] |
| 80 | B11 | (tetrahydrofuran-2'-yl)-C(=O)- | $C_2H_2O_4$ (1:1), [2R-(2α,3aα,12bβ)]-(2'RS)-(1:1) mixture of diastereoisomers |
| 81 | B11 | (thiophen-2-yl)-C(=O)- | $C_2H_2O_4$ (1:1), [2R-(2α,3aα,12bβ)] |
| 82 | B11 | phenyl-C(=O)- | $C_2H_2O_4$ (1:1), [2R-(2α,3aα,12bβ)] |
| 83 | B11 | phenyl-O-C(=O)- | $C_2H_2O_4$ (1:1), [2R-(2α,3aα,12bβ)] |
| 84 | B11 | allyl-O-C(=O)- | $C_2H_2O_4$ (1:1), [2R-(2α,3aα,12bβ)] |
| 85 | B11 | benzyl-O-C(=O)- | $C_2H_2O_4$ (1:1), [2R-(2α,3aα,12bβ)] |
| 86 | B9 | ethyl-NH-C(=O)- | $C_2H_2O_4$ (1:1), [2R-(2α,3aα,12bβ)] |
| 87 | B18 | (2-methylthio-ethyl)-NH-C(=O)- | $C_2H_2O_4$ (1:1), [2R-(2α,3aα,12bβ)] |

TABLE 2-continued
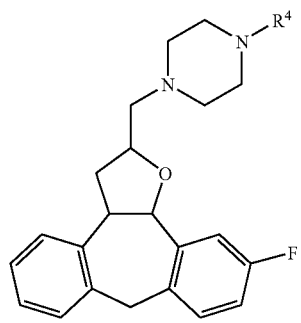
| Co. No | Ex. No | ---R⁴ | Physical data |
|---|---|---|---|
| 88 | B18 | —C(=O)NH—CH(CH₃)₂ | C₂H₂O₄ (1:1), [2R-(2α,3aα,12bβ)] |
| 89 | B9 | —C(=O)NH—(CH₂)₃CH₃ | C₂H₂O₄ (1:1), [2R-(2α,3aα,12bβ)] |
| 90 | B18 | —C(=O)NH—C(CH₃)₂CH₂CH₃ | C₂H₂O₄ (1:1), [2R-(2α,3aα,12bβ)] |
| 91 | B18 | —C(=O)NH—CH₂CH(OMe)₂ | C₂H₂O₄ (1:1), [2R-(2α,3aα,12bβ)] |
| 92 | B9 | —C(=O)NH—CH₂C(=O)OEt | C₂H₂O₄ (1:1), [2R-(2α,3aα,12bβ)] |
| 93 | B18 | —C(=O)NH—(CH₂)₃—Ph | C₂H₂O₄ (1:1), [2R-(2α,3aα,12bβ)] |
| 94 | B18 | —C(=O)NH—cyclopropyl | C₂H₂O₄ (1:1), [2R-(2α,3aα,12bβ)] |
| 95 | B9 | —C(=O)NH—cyclohexyl | C₂H₂O₄ (1:1), [2R-(2α,3aα,12bβ)] |
| 96 | B18 | —C(=O)NH—CH₂—(2,4-dimethoxyphenyl) | C₂H₂O₄ (1:1), [2R-(2α,3aα,12bβ)] |

TABLE 2-continued
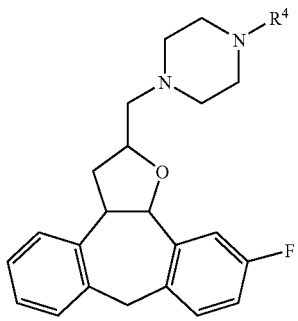
| Co. No | Ex. No | ---R⁴ | Physical data |
|---|---|---|---|
| 97 | B18 | 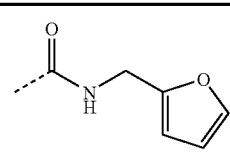 | C₂H₂O₄ (1:1), [2R-(2α,3aα,12bβ)] |
| 98 | B18 | 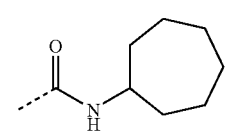 | C₂H₂O₄ (1:1), [2R-(2α,3aα,12bβ)] |
| 99 | B18 | 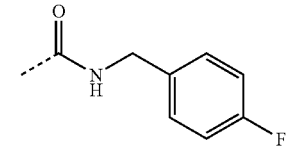 | C₂H₂O₄ (1:1), [2R-(2α,3aα,12bβ)] |
| 100 | B18 | 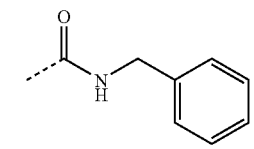 | C₂H₂O₄ (1:1), [2R-(2α,3aα,12bβ)] |
| 101 | B9 | 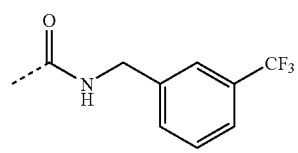 | C₂H₂O₄ (1:1), [2R-(2α,3aα,12bβ)] |
| 102 | B10 |  | C₂H₂O₄ (1:1), [2R-(2α,3aα,12bβ)] |
| 103 | B10 | 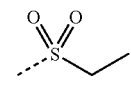 | C₂H₂O₄ (1:1), [2R-(2α,3aα,12bβ)] |
| 104 | B10 | 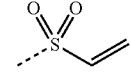 | C₂H₂O₄ (1:1), [2R-(2α,3aα,12bβ)] |
| 105 | B10 | 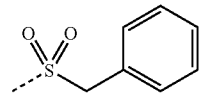 | C₂H₂O₄ (1:1), [2R-(2α,3aα,12bβ)] |

TABLE 2-continued
| Co. No | Ex. No. | R⁴ | Physical data |
|---|---|---|---|
| 106 | B10 | 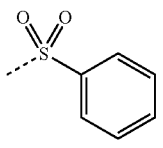 | $C_2H_2O_4$ (1:1), [2R-(2α,3aα,12bβ)] |
| 107 | B10 | 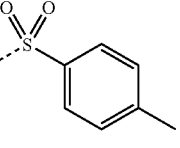 | $C_2H_2O_4$ (1:1), [2R-(2α,3aα,12bβ)] |
| 108 | B25 | 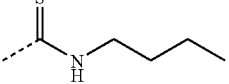 | $C_2H_2O_4$ (1:1), [2R-(2α,3aα,12bβ)] |
| 109 | B25 | 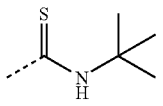 | $C_2H_2O_4$ (1:1), [2R-(2α,3aα,12bβ)] |
| 110 | B25 | 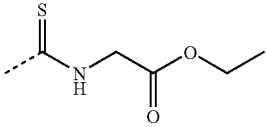 | $C_2H_2O_4$ (1:1), [2R-(2α,3aα,12bβ)] |
| 111 | B25 | 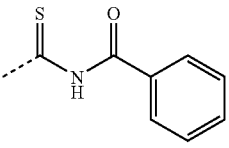 | $C_2H_2O_4$ (1:1), [2R-(2α,3aα,12bβ)] |
| 112 | B25 | 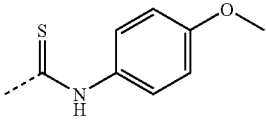 | $C_2H_2O_4$ (1:1), [2R-(2α,3aα,12bβ)] |
| 113 | B25 | 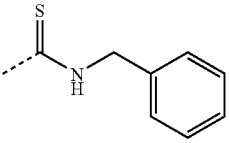 | $C_2H_2O_4$ (1:1), [2R-(2α,3aα,12bβ)] |
| 114 | B25 | 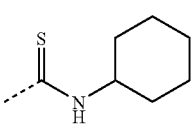 | $C_2H_2O_4$ (1:1), [2R-(2α,3aα,12bβ)] |

TABLE 2-continued
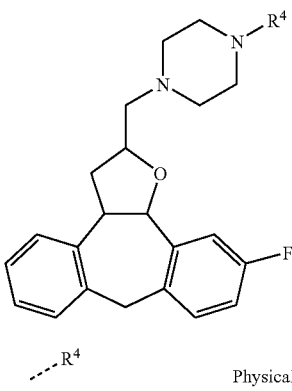
| Co. No | Ex. No | ---R⁴ | Physical data |
|---|---|---|---|
| 115 | B25 | 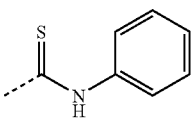 | C₂H₂O₄ (1:1), [2R-(2α,3aα,12bβ)] |
| 116 | B1 | 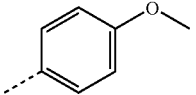 | C₂H₂O₄ (1:1), [2R-(2α,3aα,12bβ)] |
| 117 | B1 | 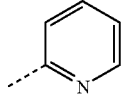 | C₂HF₃O₂ (1:1), [2R-(2α,3aα,12bβ)] |
| 118 | B10 | 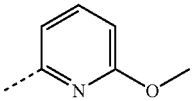 | C₂H₂O₄ (1:1), [2R-(2α,3aα,12bβ)] |
| 119 | B10 | 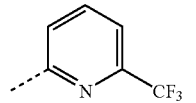 | C₂HF₃O₂ (1:1), [2R-(2α,3aα,12bβ)] |
| 120 | B10 | 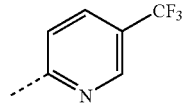 | C₂H₂O₄ (1:1), [2R-(2α,3aα,12bβ)] |
| 121 | B10 | 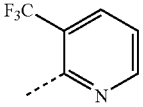 | C₂H₂O₄ (1:1), [2R-(2α,3aα,12bβ)] |
| 122 | B10 | 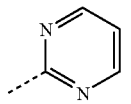 | C₂HF₃O₂ (1:1), [2R-(2α,3aα,12bβ)] |
| 123 | B10 | 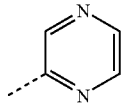 | C₂H₂O₄ (1:1), [2R-(2α,3aα,12bβ)] |
| 124 | B10 | 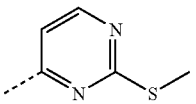 | C₂H₂O₄ (1:1), [2R-(2α,3aα,12bβ)] |

TABLE 2-continued
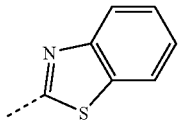
| Co. No | Ex. No | ----R⁴ | Physical data |
|---|---|---|---|
| 125 | B10 | 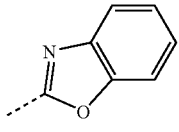 | $C_2HF_3O_2$ (1:1), [2R-(2α,3aα,12bβ)] |
| 126 | B10 | 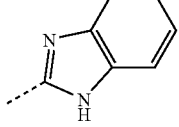 | $C_2H_2O_4$ (1:1), [2R-(2α,3aα,12bβ)] |
| 127 | B10 |  | [2R-(2α,3aα,12bβ)] |
TABLE 3
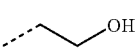
| Co. No | Ex. No | ----R⁶ | Physical data |
|---|---|---|---|
| 128 | B1 | ⋯⋯OH | $C_2H_2O_4$ (1:1), [2R-(2α,3aα,12bβ)]-(3'RS)-(1:1) mixture of diastereoisomers |
| 129 | B16 | ⋯⋯∕∖OH | $C_2H_2O_4$ (1:1), [2R-(2α,3aα,12bβ)]-(3'RS), (1:1) mixture of diastereoisomers |
| 130 | B16 | ⋯⋯∕∖O∕ | $C_2H_2O_4$ (1:1), [2R-(2α,3aα,12bβ)]-(3'RS), (1:1) mixture of diastereoisomers |
| 131 | B16 |  | $C_2H_2O_4$ (1:1), [2R-(2α,3aα,12bβ)]-(3'RS), (1:1) mixture of diastereoisomers |

TABLE 3-continued

| Co. No | Ex. No | R⁶ | Physical data |
|---|---|---|---|
| 132 | B16 | —CH₂CH₂N(CH₃)₂ | C₂H₂O₄ (1:1), [2R-(2α,3aα,12bβ)]-(3'RS), (1:1) mixture of diastereoisomers |
| 133 | B1 | —CH₂CH₂N(CH₃)CH₂CH₂OH | C₂H₂O₄ (1:1), [2R-(2α,3aα,12bβ)]-(3'RS), (1:1) mixture of diastereoisomers |
| 134 | B16 | —CH₂C(=O)OH | C₂H₂O₄ (1:1), [2R-(2α,3aα,12bβ)]-(3'RS), (1:1) mixture of diastereoisomers |
| 135 | B16 | —CH₂C(=O)OCH₂CH₃ | C₂H₂O₄ (1:1), [2R-(2α,3aα,12bβ)]-(3'RS), (1:1) mixture of diastereoisomers |
| 136 | B16 | —CH₂C(=O)N(CH₃)₂ | C₂H₂O₄ (1:1), [2R-(2α,3aα,12bβ)]-(3'RS), (1:1) mixture of diastereoisomers |
| 137 | B9 | —CH₂OC(=O)NHCH₂CH₃ | C₂H₂O₄ (1:1), [2R-(2α,3aα,12bβ)]-(3'RS), (1:1) mixture of diastereoisomers |
| 138 | B16 | —CH₂CH₂OS(=O)₂CH₃ | [2R-(2α,3aα,12bβ)]-(3'RS), (1:1) mixture of diastereoisomers |
| 139 | B16 | —CH₂C(=O)NH-C₆H₄-OCH₃ | C₂H₂O₄ (1:1), [2R-(2α,3aα,12bβ)]-(3'RS), (1:1) mixture of diastereoisomers |

TABLE 4

| Co. No | Ex. No | R³ | Physical data |
|---|---|---|---|
| 140 | B1 | 3'-OH | [2R-(2α,3aα,12bβ)]-(3'RS)-(1:1) mixture of diastereoisomers |
| 141 | B1 | 3'-OH | C₂H₂O₄ (1:1), [2R-(2α,3aα,12bβ)]-(3'RS)-(1:1) mixture of diastereoisomers |
| 142 | B1 | 3'-OH | C₂H₂O₄ (1:1), [2R-(2α,3aα,12bβ)]-(3'S*) |
| 143 | B1 | 3'-OH | C₂H₂O₄ (1:1), [2R-(2α,3aα,12bβ)]-(3'R*) |
| 144 | B2 | 4'-OH | C₂H₂O₄ (1:1), [2R-(2α,3aα,12bβ)] |
| 145 | B15 | 2'-CH₂OH | [2R-(2α,3aα,12bβ)]-(2'RS)-(1:1) mixture of diastereoisomers |
| 146 | B15 | 2'-CH₂OH | C₂H₂O₄ (1:1), [2R-(2α,3aα,12bβ)]-(2'RS)-(1:1) mixture of diastereoisomers |
| 147 | B15 | 3'-CH₂OH | C₂H₂O₄ (1:1), [2R-(2α,3aα,12bβ)]-(3'RS)-(1:1) mixture of diastereoisomers |
| 148 | B15 | 3'-CH₂OH | C₂H₂O₄ (1:1), [2R-(2α,3aα,12bβ)]-(3'R*) |
| 149 | B15 | 3'-CH₂OH | C₂H₂O₄ (1:1), [2R-(2α,3aα,12bβ)]-(3'S*) |
| 150 | B15 | 4'-CH₂OH | [2R-(2α,3aα,12bβ)] |
| 151 | B15 | 4'-CH₂OH | C₂H₂O₄ (1:1), [2R-(2α,3aα,12bβ)] |
| 152 | B1 | 3'-CH₂CH₂OH | C₂HF₃O₂ (1:1), [2R-(2α,3aα,12bβ)]-(3'RS)-(1:1) mixture of diastereoisomers |
| 153 | B3 | 4'-CH₂CH₂OH | [2R-(2α,3aα,12bβ)] |
| 154 | B3 | 4'-CH₂CH₂OH | C₂H₂O₄ (1:1), [2R-(2α,3aα,12bβ)] |
| 155 | B1 | 4'-CH₂CH₂CH₂OH | C₂H₂O₄ (1:1), [2R-(2α,3aα,12bβ)] |
| 156 | B7 | 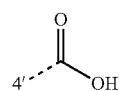 | [2R-(2α,3aα,12bβ)] |
| 157 | B19 | 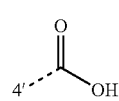 | C₂H₂O₄ (1:1), [2R-(2α,3aα,12bβ)] |

TABLE 4-continued

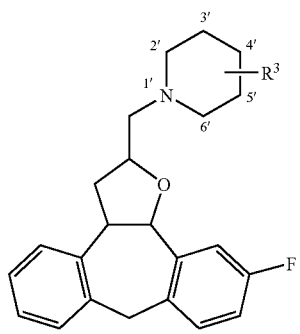

| Co. No | Ex. No | R³ | Physical data |
|---|---|---|---|
| 158 | B1 | 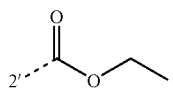 | C₂H₂O₄ (1:1), [2R-(2α,3aα,12bβ)]-(2'RS)-(1:1) mixture of diastereoisomers |
| 159 | B15 | 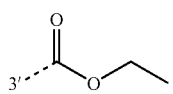 | [2R-(2α,3aα,12bβ)]-(3'RS)-(1:1) mixture of diastereoisomers |
| 160 | B15 | 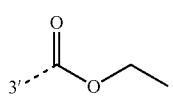 | C₂H₂O₄ (1:1), [2R-(2α,3aα,12bβ)]-(3'RS)-(1:1) mixture of diastereoisomers |
| 161 | B7 | 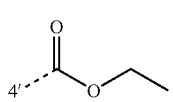 | [2R-(2α,3aα,12bβ)] |
| 162 | B7 | 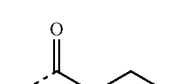 | C₂H₂O₄ (1:1), [2R-(2α,3aα,12bβ)] |
| 163 | B1 | 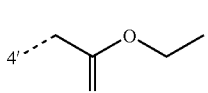 | [2R-(2α,3aα,12bβ)] |
| 164 | B1 | 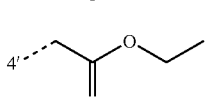 | C₂H₂O₄ (1:1), [2R-(2α,3aα,12bβ)] |
| 165 | B1 | 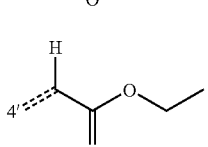 | C₂H₂O₄ (1:1), [2R-(2α,3aα,12bβ)] |
| 166 | B8 | 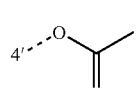 | C₂H₂O₄ (1:1), [2R-(2α,3aα,12bβ)] |
| 167 | B1 | 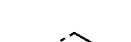 | C₂HF₃O₂ (1:1), [2R-(2α,3aα,12bβ)]-(3'RS)-(1:1) mixture of diastereoisomers |
| 168 | B1 |  | C₂H₂O₄ (1:1), [2R-(2α,3aα,12bβ)] |
| 169 | B1 |  | C₂HF₃O₂ (1:1), [2R-(2α,3aα,12bβ)]-(3'RS)-(1:1) mixture of diastereoisomers |
| 170 | B1 |  | C₂HF₃O₂ (1:1), [2R-(2α,3aα,12bβ)] |

TABLE 4-continued
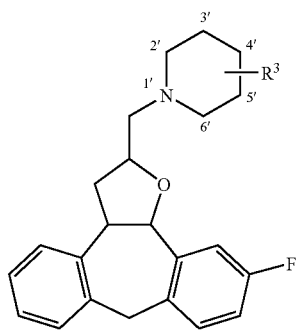
| Co. No | Ex. No | ----R³ | Physical data |
|---|---|---|---|
| 171 | B1 | 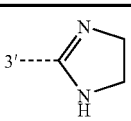 | C₂HF₃O₂ (1:1), [2R-(2α,3aα,12bβ)]-(3'RS)-(1:1) mixture of diastereoisomers |
| 172 | B1 | 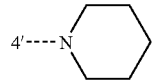 | C₂H₂O₄ (1:2), [2R-(2α,3aα,12bβ)] |
| 173 | B7 | 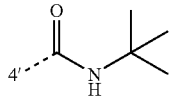 | [2R-(2α,3aα,12bβ)] |
| 174 | B7 | 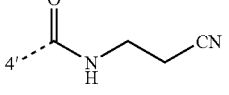 | [2R-(2α,3aα,12bβ)] |
| 175 | B7 | 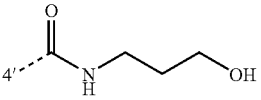 | [2R-(2α,3aα,12bβ)] |
| 176 | B7 | 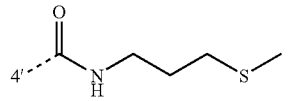 | [2R-(2α,3aα,12bβ)] |
| 177 | B7 | 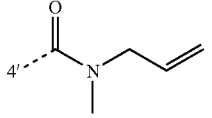 | C₂HF₃O₂ (1:1), [2R-(2α,3aα,12bβ)] |
| 178 | B7 | 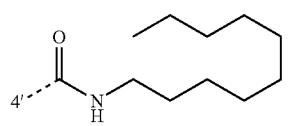 | C₂HF₃O₂ (1:1), [2R-(2α,3aα,12bβ)] |
| 179 | B7 | 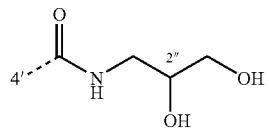 | C₂HF₃O₂ (1:1), [2R-(2α,3aα,12bβ)]-(2"RS)-(1:1) mixture of diastereoisomers |
| 180 | B7 | 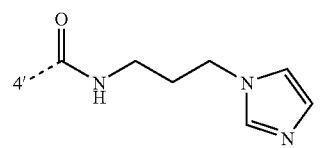 | C₂HF₃O₂ (1:1), [2R-(2α,3aα,12bβ)] |

TABLE 4-continued
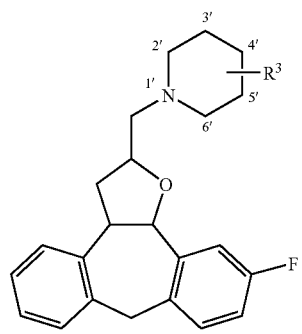
| Co. No | Ex. No. | ---R³ | Physical data |
|---|---|---|---|
| 181 | B7 | 4'---C(=O)NH-CH₂CH₂-N(morpholine) | $C_2HF_3O_2$ (1:1), [2R-(2α,3aα,12bβ)] |
| 182 | B7 | 4'---C(=O)NH-CH₂-(3-CF₃-phenyl) | [2R-(2α,3aα,12bβ)] |
| 183 | B7 | 4'---C(=O)NH-(4-SMe-phenyl) | $C_2HF_3O_2$ (1:1), [2R-(2α,3aα,12bβ)] |
| 184 | B7 | 4'---C(=O)NH-CH(CO₂Me)-CH₂-(4-Cl-phenyl) | [2R-(2α,3aα,12bβ)]-(2"RS)-(1:1) mixture of diastereoisomers |
| 185 | B7 | 4'---C(=O)NH-(2-iPr-phenyl) | [2R-(2α,3aα,12bβ)] |
| 186 | B7 | 4'---C(=O)NH-CH₂-(2,4,6-triOMe-phenyl) | [2R-(2α,3aα,12bβ)] |
| 187 | B7 | 4'---C(=O)NH-cyclopropyl | $C_2HF_3O_2$ (1:1), [2R-(2α,3aα,12bβ)] |
| 188 | B7 | 4'---C(=O)NH-cyclohexyl | $C_2HF_3O_2$ (1:1), [2R-(2α,3aα,12bβ)] |

TABLE 4-continued
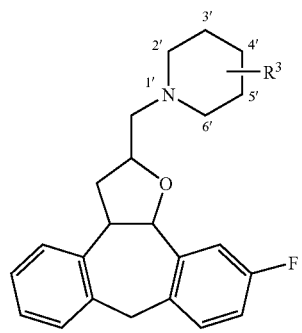
| Co. No | Ex. No | ----R³ | Physical data |
|---|---|---|---|
| 189 | B7 | 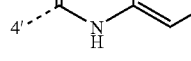 | C₂HF₃O₂ (1:1), [2R-(2α,3aα,12bβ)] |
| 190 | B7 | 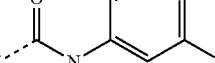 | C₂HF₃O₂ (1:1), [2R-(2α,3aα,12bβ)] |
| 191 | B7 | 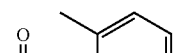 | C₂HF₃O₂ (1:1), [2R-(2α,3aα,12bβ)] |
| 192 | B7 |  | C₂HF₃O₂ (1:1), [2R-(2α,3aα,12bβ)] |
| 193 | B7 | 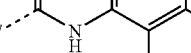 | C₂HF₃O₂ (1:1), [2R-(2α,3aα,12bβ)] |
| 194 | B7 |  | [2R-(2α,3aα,12bβ)] |
| 195 | B7 | 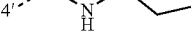 | [2R-(2α,3aα,12bβ)] |
| 196 | B7 | 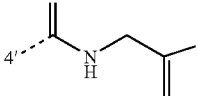 | [2R-(2α,3aα,12bβ)] |

TABLE 4-continued
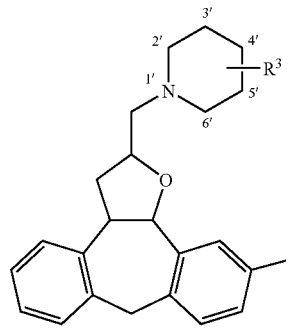
| Co. No | Ex. No | ---R³ | Physical data |
|---|---|---|---|
| 197 | B7 | 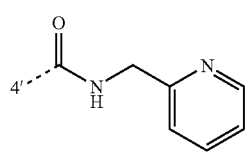 | [2R-(2α,3aα,12bβ)] |
| 198 | B7 | 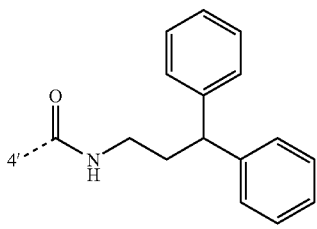 | [2R-(2α,3aα,12bβ)] |
| 199 | B7 | 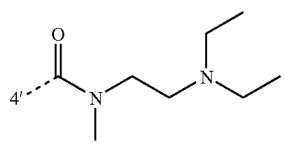 | C₂HF₃O₂ (1:1), [2R-(2α,3aα,12bβ)] |
| 200 | B7 | 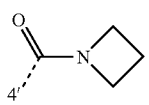 | C₂HF₃O₂ (1:1), [2R-(2α,3aα,12bβ)] |
| 201 | B7 | 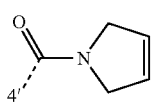 | C₂HF₃O₂ (1:1), [2R-(2α,3aα,12bβ)] |
| 202 | B7 | 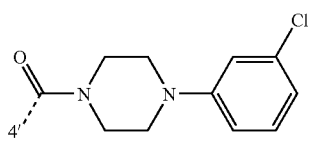 | C₂HF₃O₂ (1:1), [2R-(2α,3aα,12bβ)] |
| 203 | B7 | 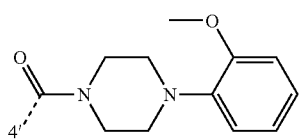 | C₂HF₃O₂ (1:1), [2R-(2α,3aα,12bβ)] |

TABLE 4-continued
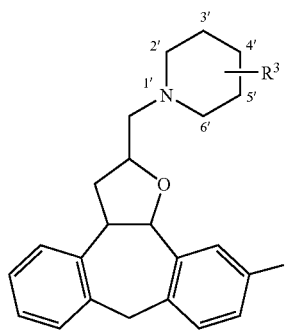
| Co. No | Ex. No | R³ | Physical data |
|---|---|---|---|
| 204 | B7 | 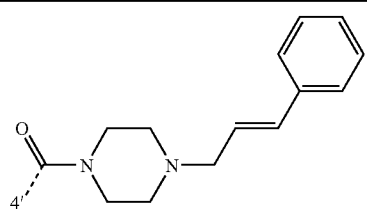 | C₂HF₃O₂ (1:1), [2R-(2α,3aα(E),12bβ)] |
| 205 | B7 | 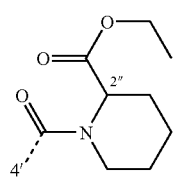 | C₂HF₃O₂ (1:1), [2R-(2α,3aα,12bβ)]-(2″RS)-(1:1) mixture of diastereoisomers |
| 206 | B7 | 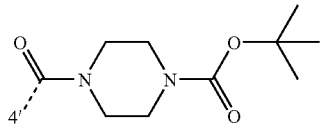 | C₂HF₃O₂ (1:1), [2R-(2α,3aα,12bβ)] |
| 207 | B7 | 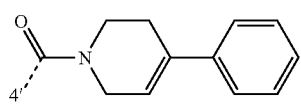 | [2R-(2α,3aα,12bβ)] |
| 208 | B7 | 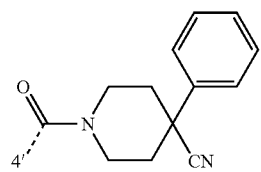 | [2R-(2α,3aα,12bβ)] |
| 209 | B7 | 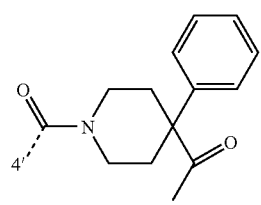 | [2R-(2α,3aα,12bβ)] |
| 210 | B23 | 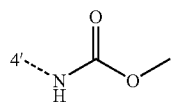 | C₂HF₃O₂ (1:1), [2R-(2α,3aα,12bβ)] |

TABLE 4-continued
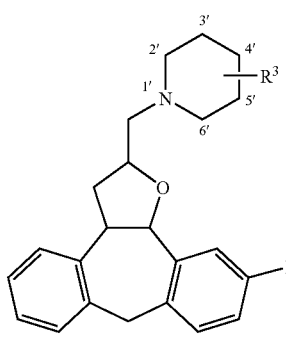
| Co. No | Ex. No | ---R³ 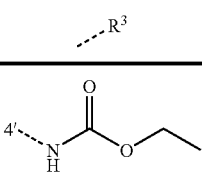 | Physical data |
|---|---|---|---|
| 211 | B23 | 4'---NH-C(=O)-O-ethyl | C₂HF₃O₂ (1:1), [2R-(2α,3aα,12bβ)] |
| 212 | B23 | 4'---NH-C(=O)-O-propyl | C₂HF₃O₂ (1:1), [2R-(2α,3aα,12bβ)] |
| 213 | B23 | 4'---NH-C(=O)-O-butyl | C₂HF₃O₂ (1:1), [2R-(2α,3aα,12bβ)] |
| 214 | B23 | 4'---NH-C(=O)-O-isobutyl | C₂HF₃O₂ (1:1), [2R-(2α,3aα,12bβ)] |
| 215 | B23 | 4'---NH-C(=O)-O-neopentyl | C₂HF₃O₂ (1:1), [2R-(2α,3aα,12bβ)] |
| 216 | B23 | 4'---NH-C(=O)-O-CH₂CH₂OCH₃ | C₂HF₃O₂ (1:1), [2R-(2α,3aα,12bβ)] |
| 217 | B23 | 4'---NH-C(=O)-O-CH₂C≡CH | C₂HF₃O₂ (1:1), [2R-(2α,3aα,12bβ)] |
| 218 | B23 | 4'---NH-C(=O)-O-CH₂-(2-Cl-phenyl) | C₂HF₃O₂ (1:1), [2R-(2α,3aα,12bβ)] |
| 219 | B23 | 4'---NH-C(=O)-O-(4-methoxyphenyl) | C₂HF₃O₂ (1:1), [2R-(2α,3aα,12bβ)] |

TABLE 4-continued
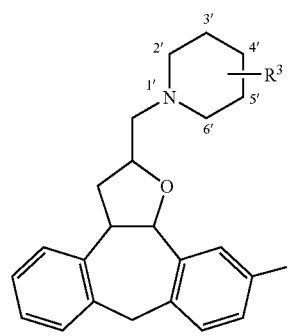
| Co. No | Ex. No | ---R³ | Physical data |
|---|---|---|---|
| 220 | B23 | 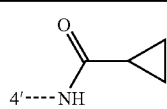 | C₂HF₃O₂ (1:1), [2R-(2α,3aα,12bβ)] |
| 221 | B23 | 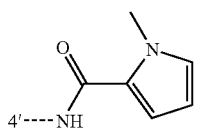 | C₂HF₃O₂ (1:1), [2R-(2α,3aα,12bβ)] |
| 222 | B23 | 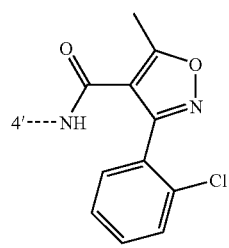 | C₂HF₃O₂ (1:1), [2R-(2α,3aα,12bβ)] |
| 223 | B23 | 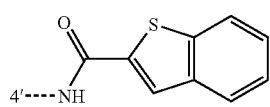 | C₂HF₃O₂ (1:1), [2R-(2α,3aα,12bβ)] |
| 224 | B23 | 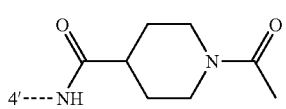 | C₂HF₃O₂ (1:1), [2R-(2α,3aα,12bβ)] |
| 225 | B23 | 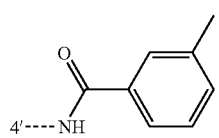 | C₂HF₃O₂ (1:1), [2R-(2α,3aα,12bβ)] |
| 226 | B23 | 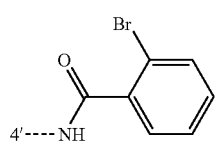 | C₂HF₃O₂ (1:1), [2R-(2α,3aα,12bβ)] |
| 227 | B23 | 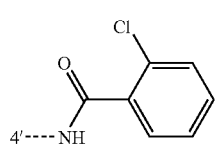 | C₂HF₃O₂ (1:1), [2R-(2α,3aα,12bβ)] |

TABLE 4-continued

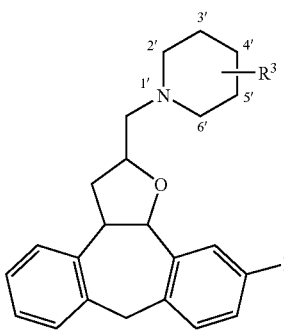

| Co. No | Ex. No | ----R³ | Physical data |
|---|---|---|---|
| 228 | B23 | 2,3-dichlorobenzamide (4'-NH) | $C_2HF_3O_2$ (1:1), [2R-(2α,3aα,12bβ)] |
| 229 | B23 | 3,4-dichlorobenzamide (4'-NH) | $C_2HF_3O_2$ (1:1), [2R-(2α,3aα,12bβ)] |
| 230 | B23 | 2,4-dichlorobenzamide (4'-NH) | $C_2HF_3O_2$ (1:1), [2R-(2α,3aα,12bβ)] |
| 231 | B23 | 3-fluorobenzamide (4'-NH) | $C_2HF_3O_2$ (1:1), [2R-(2α,3aα,12bβ)] |
| 232 | B23 | 2-fluorobenzamide (4'-NH) | $C_2HF_3O_2$ (1:1), [2R-(2α,3aα,12bβ)] |
| 233 | B23 | 3-trifluoromethylbenzamide (4'-NH) | $C_2HF_3O_2$ (1:1), [2R-(2α,3aα,12bβ)] |
| 234 | B23 | pentafluorobenzamide (4'-NH) | $C_2HF_3O_2$ (1:1), [2R-(2α,3aα,12bβ)] |
| 235 | B23 | 3,4,5-trimethoxybenzamide (4'-NH) | $C_2HF_3O_2$ (1:1), [2R-(2α,3aα,12bβ)] |

TABLE 4-continued

| Co. No | Ex. No | ---R³ | Physical data |
|---|---|---|---|
| 236 | B23 | 4'---NH-C(O)-C6H4-CN (para) | C₂HF₃O₂ (1:1), [2R-(2α,3aα,12bβ)] |
| 237 | B24 | 4'---NH-C(O)-C6H4-C6H5 (biphenyl) | C₂HF₃O₂ (1:1), [2R-(2α,3aα,12bβ)] |
| 238 | B23 | 4'---NH-C(O)-NH-(2,3-dihydro-1H-inden-5-yl) | C₂HF₃O₂ (1:1), [2R-(2α,3aα,12bβ)] |
| 239 | B23 | 4'---NH-C(O)-CH2-C6H4-Cl (para) | C₂HF₃O₂ (1:1), [2R-(2α,3aα,12bβ)] |
| 240 | B23 | 4'---NH-C(O)-CH2-(thiophen-2-yl) | C₂HF₃O₂ (1:1), [2R-(2α,3aα,12bβ)] |
| 241 | B23 | 4'---NH-C(O)-CH2-S-C6H5 | C₂HF₃O₂ (1:1), [2R-(2α,3aα,12bβ)] |
| 242 | B24 | 4'---NH-C(O)-NH-CH2-C(O)-O-CH2CH3 | C₂HF₃O₂ (1:1), [2R-(2α,3aα,12bβ)] |
| 243 | B23 | 4'---NH-C(O)-N(CH3)2 | C₂HF₃O₂ (1:1), [2R-(2α,3aα,12bβ)] |
| 244 | B24 | 4'---NH-C(O)-NH-CH2CH2CH3 | C₂HF₃O₂ (1:1), [2R-(2α,3aα,12bβ)] |

TABLE 4-continued
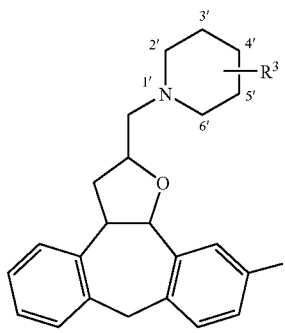
| Co. No | Ex. No | ----R³ | Physical data |
|---|---|---|---|
| 245 | B24 | 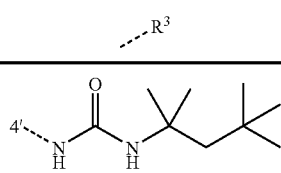 | C₂HF₃O₂ (1:1), [2R-(2α,3aα,12bβ)] |
| 246 | B24 | 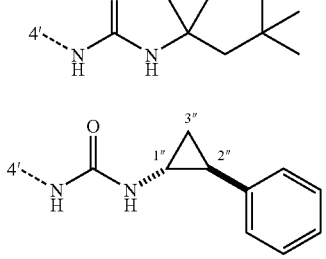 | C₂HF₃O₂ (1:1), [2R-(2α,3aα,12bβ)]-tRanS-(1"RS,2"RS)-(1:1) mixture of diastereoisomers |
| 247 | B24 | 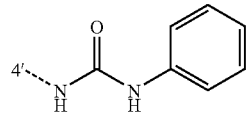 | C₂HF₃O₂ (1:1), [2R-(2α,3aα,12bβ)] |
| 248 | B24 | 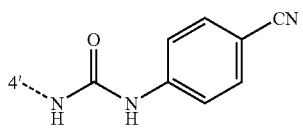 | C₂HF₃O₂ (1:1), [2R-(2α,3aα,12bβ)] |
| 249 | B24 | 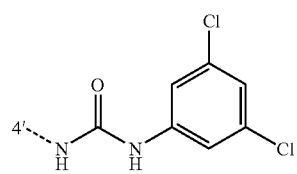 | C₂HF₃O₂ (1:1), [2R-(2α,3aα,12bβ)] |
| 250 | B24 | 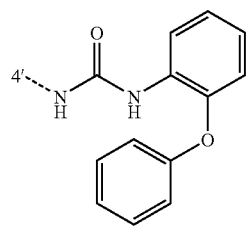 | C₂HF₃O₂ (1:1), [2R-(2α,3aα,12bβ)] |
| 251 | B24 | 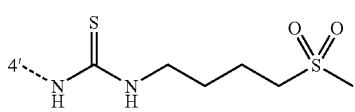 | C₂HF₃O₂ (1:1), [2R-(2α,3aα,12bβ)] |
| 252 | B24 | 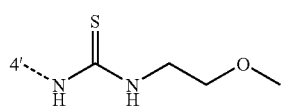 | C₂HF₃O₂ (1:1), [2R-(2α,3aα,12bβ)] |

TABLE 4-continued

| Co. No | Ex. No | ----R³ | Physical data |
|---|---|---|---|
| 253 | B24 | (thiourea-CH2CH2-morpholine) | C₂HF₃O₂ (1:1), [2R-(2α,3aα,12bβ)] |
| 254 | B24 | (thiourea-3-pyridyl) | C₂HF₃O₂ (1:1), [2R-(2α,3aα,12bβ)] |
| 255 | B24 | (thiourea-3,4,5-trimethoxyphenyl) | C₂HF₃O₂ (1:1), [2R-(2α,3aα,12bβ)] |
| 256 | B24 | (thiourea-CH2CH2-NH2) | C₂HF₃O₂ (1:1), [2R-(2α,3aα,12bβ)] |

TABLE 5

| Co. No | Ex. No | X | R¹ | R² | R³ | Physical data |
|---|---|---|---|---|---|---|
| 257 | B22 | —S— | —H | —I | —F | [2R*-(2α,3aα,12bβ)]-(3'RS) + [2R*-(2β,3aα,12bβ)]-(3'RS) |
| 258 | B22 | —S— | —H | —I | —F | [2RS-(2β,3aα,12bβ)]-(3'RS) |
| 259 | B22 | —S— | —H | —CN | —F | C₂H₂O₄ (1:1), C₂H₂O₄ (1:1), [2R*-(2α,3aα,12bβ)]-(3'RS) |
| 260 | B22 | —S— | —H | —CN | —F | C₂H₂O₄ (1:1), [2S*-(2β,3aα,12bβ)]- |

TABLE 5-continued
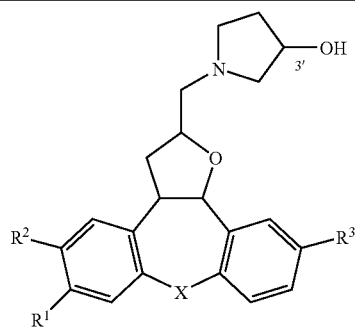
| Co. No | Ex. No | X | R[1] | R[2] | R[3] | Physical data |
|---|---|---|---|---|---|---|
| 261 | B22 | —CH$_2$— | —H | —CN | —F | (3'RS) [2R-(2α,3aα,12bβ)]-(3'RS) |
| 262 | B22 | —CH$_2$— | —CN | —H | —F | [2R-(2α,3aα,12bβ)]-(3'RS) |
| 263 | B1 | ⟨N-⟩ | —H | —H | —H | C$_2$H$_2$O$_4$ (1:1), [2RS-(2β,3aα,12bβ)]-(3'RS) + [2RS-(2α,3aα,12bβ)]-(3'RS) |
| 264 | B1 | ⟨N-⟩ | —H | —H | —H | C$_2$H$_2$O$_4$ (1:1), [2RS-(2β,3aα,12bβ)]-(3'RS) |
TABLE 6
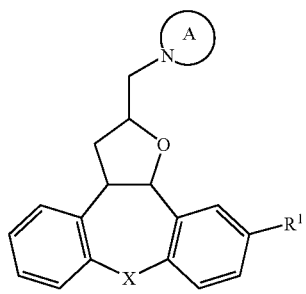
| Co. No | Ex. No | X | R[1] | —N⟨A⟩ | Physical data |
|---|---|---|---|---|---|
| 265 | B1 | —CH$_2$— | —F | pyrroline | [2R-(2α,3aα,12bβ)] |
| 266 | B1 | —CH$_2$— | —F | pyrroline | C$_2$H$_2$O$_4$ (1:1), [2R-(2α,3aα,12bβ)] |
| 267 | B1 | —CH$_2$— | —F | homopiperazine-NH | C$_2$H$_2$O$_4$ (1:2), [2R-(2α,3aα,12bβ)] |

TABLE 6-continued
| Co. No | Ex. No | X | R¹ |  | Physical data |
|---|---|---|---|---|---|
| 268 | B1 | —CH₂— | —F | 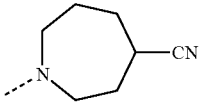 | C₂H₂O₄ (1:2), [2R-(2α,3aα,12bβ)] |
| 269 | B10 | —CH₂— | —F |  | C₂H₂O₄ (1:1), [2R-(2α,3aα,12bβ)] |
| 270 | B1 | —CH₂— | —F | 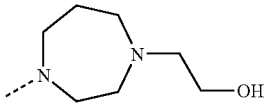 | C₂HF₃O₂ (1:1), [2R-(2α,3aα,12bβ)] |
| 271 | B21 | —CH₂— | —F |  | [2R-(2α,3aα,12bβ)]-(3'RS,4'RS) |
| 272 | B4 | —CH₂— | —F | 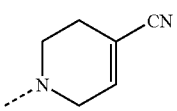 | C₂HF₃O₂ (1:1), [2R-(2α,3aα,12bβ)] |
| 273 | B1 | —CH₂— | —F |  | C₂H₂O₄ (1:1), [2R-(2α,3aα,12bβ)] |
| 274 | B21 | —CH₂— | —F | 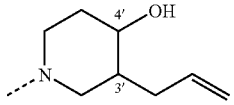 | C₂H₂O₄ (1:1), [2R-(2α,3aα,12bβ)]-(2'RS,3a'RS,7a'RS) mixture of diastereoisomers |
| 275 | B1 | —CH₂— | —F |  | C₂HF₃O₂ (1:1), [2R-(2α,3aα,12bβ)] |
| 276 | B5 | —CH₂— | —F | 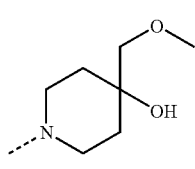 | C₂HF₃O₂ (1:1), [2R-(2α,3aα,12bβ)] |

TABLE 6-continued
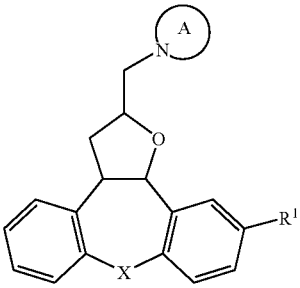
| Co. No | Ex. No | X | R¹ | 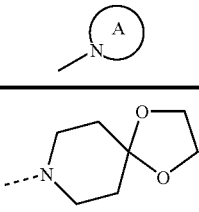 | Physical data |
|---|---|---|---|---|---|
| 277 | B6 | —CH₂— | —F | 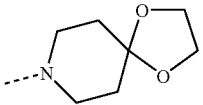 | [2R-(2α,3aα,12bβ)] |
| 278 | B6 | —CH₂— | —F | 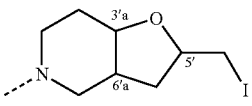 | C₂H₂O₄ (1:1), [2R-(2α,3aα,12bβ)] |
| 279 | B21 | —CH₂— | —F | 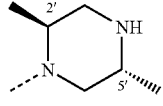 | [2R-(2α,3aα,12bβ)]-(2'RS,3a'RS,7a'RS)) mixture of diastereoisomers |
| 280 | B1 | —CH₂— | —F | 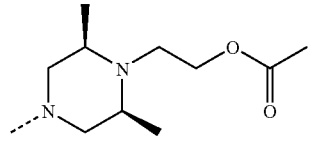 | C₂H₂O₄ (1:1), [2R-(2α,3aα,12bβ)]-[2'RS,5'RS-(2'β,5'α)] |
| 281 | B10 | —CH₂— | —F | 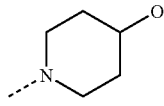 | C₂H₂O₄ (1:1), [2R-(2α,3aα,12bβ)]-(3'β,5'β) |
| 282 | B1 | —O— | —F | 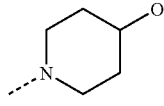 | C₂H₂O₄ (1:1), [2RS-(2β,3aα,12bα)] |
| 283 | B1 | —O— | —F | 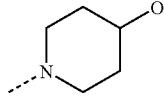 | C₂H₂O₄ (1:1), [2RS-(2α,3α,12bα)] |
| 284 | B1 | —O— | —Cl | 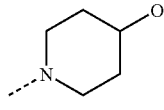 | C₂H₂O₄ (1:1), [2RS-(2β,3aα,12bα)] |
| 285 | B1 | —O— | —Cl | 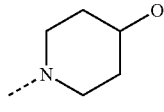 | C₂H₂O₄ (1:1), [2RS-(2α,3α,12bα)] |
| 286 | B1 | —O— | —Br |  | C₂H₂O₄ (1:1), [2RS-(2α,3α,12bα)] |

TABLE 6-continued

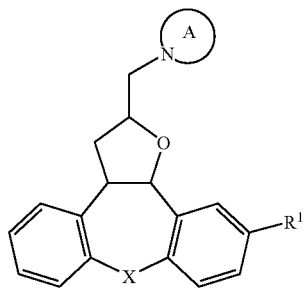

| Co. No | Ex. No | X | R¹ | [N-A structure] | Physical data |
|---|---|---|---|---|---|
| 287 | B1 | —O— | ~O~ | piperidine-4-ol | $C_2H_2O_4$ (1:1), [2RS-(2α,3α,12bα)] |
| 288 | B1 | —O— | ~O~ | piperidine-4-ol | $C_2H_2O_4$ (1:1), [2RS-(2α,3aβ,12bβ)] |

C. Physico-Chemical Data

The LCMS data shown in Table 7 have been obtained by the following method:

The HPLC gradient was supplied by a HP 1100 from Agilent with a column heater set at 40° C. Flow from the column was passed through photodiode array (PDA) detector and then split to a Light Scattering detector (ELSD) and to a Waters-Micromass Time of Flight (ToF) mass spectrometer with an electrospray ionization source operated simultaneously in positive and negative ionization mode.

Reversed phase HPLC was carried out on a XDB-C18 cartridge (3.5 μm, 4.6×30 mm) from Agilent, with a flow rate of 1 ml/min. Three mobile phases (mobile phase A: 0.5 g/l ammoniumacetate solution, mobile phase B: acetonitrile; mobile phase C: methanol) were employed to run a gradient condition from 80% A, 10% B, 10% C to 50% B and 50% C in 6.0 min., to 100% B at 6.5 min., kept till 7.0 min and reequilibrated with 80% A, 10% B and 10% C at 7.6 min. that was kept till 9.0 min. An injection volume of 5 μL was used.

High Resolution Mass spectra were acquired by scanning from 100 to 750 in 1 s using a dwell time of 1 s. The capillary needle voltage was 3 kV and the source temperature was maintained at 140° C. Nitrogen was used a the nebulizer gas. Cone voltage was 30 V for both positive and negative ionization mode. Leucine-enkephaline was the reference used for the lock spray. Data acquisition was performed with a Waters-Micromass MassLynx-Openlynx data system.

TABLE 7

| Co. No. | Retention time (min.) | Parent peak mass (ES⁺) | Main Fragment/Aduct (ES⁺) |
|---|---|---|---|
| 1 | 4.13/4.17 | 354 [M + H⁺] | — |
| 2 | 4.08 | 354 [M + H⁺] | — |
| 3 | 4.12 | 354 [M + H⁺] | — |
| 4 | 5.29/5.24 | 368 [M + H⁺] | 390 [M + Na⁺] |
| 5 | 4.04 | 368 [M + H⁺] | 390 [M + Na⁺] |
| 6 | 4.20 | 382 [M + H⁺] | — |
| 7 | 5.35 | 352 [M + H⁺] | — |
| 9 | 4.88 | 381 [M + H⁺] | 403 [M + Na⁺] |
| 10 | 3.60 | 382 [M + H⁺] | 380 [M − H⁺] |
| 11 | 5.71 | 396 [M + H⁺] | 418 [M + Na⁺] |
| 12 | 5.65 | 396 [M + H⁺] | — |
| 13 | 6.03 | 422 [M + H⁺] | — |
| 14 | 6.47 | 450 [M + H⁺] | — |
| 15 | 6.51 | 472 [M + H⁺] | — |
| 16 | 6.41 | 476 [M + H⁺] | — |
| 17 | 6.37 | 494 [M + H⁺] | — |
| 18 | 6.29 | 472 [M + H⁺] | — |
| 19 | 5.87 | 642 [M + H⁺] | — |
| 20 | 5.22 | 439 [M + H⁺] | — |
| 21 | 6.13 | 493 [M + H⁺] | 515 [M + Na⁺] |
| 22 | 5.90 | 487 [M + H⁺] | — |
| 23 | 5.94 | 505 [M + H⁺] | 527 [M + Na⁺] |
| 24 | 5.78 | 501 [M + H⁺] | — |
| 25 | 6.21 | 474 [M + H⁺] | — |
| 26 | 6.30 | 462 [M + H⁺] | — |
| 27 | 6.39 | 462 [M + H⁺] | — |
| 28 | 6.69 | 444 [M + H⁺] | — |
| 29 | 6.25 | 455 [M + H⁺] | — |
| 30 | 6.44 | 488 [M + H⁺] | — |
| 31 | 6.44 | 460 [M + H⁺] | — |
| 32 | 6.18 | 460 [M + H⁺] | 482 [M + Na⁺] |
| 33 | 6.36 | 460 [M + H⁺] | — |
| 34 | 6.43 | 448 [M + H⁺] | — |
| 35 | 6.54 | 448 [M + H⁺] | — |
| 36 | 6.50 | 448 [M + H⁺] | — |
| 37 | 6.76 | 498 [M + H⁺] | — |
| 38 | 5.13 | 382 [M + H⁺] | — |
| 39 | 4.55/4.59 | 368 [M + H⁺] | — |
| 40 | 5.06 | 380 [M + H⁺] | — |
| 41 | 5.85 | 448 [M + H⁺] | 470 [M + Na⁺] |
| 43 | 4.60 | 372 [M + H⁺] | 394 [M + Na⁺] |
| 44 | 4.59/4.70 | 372 [M + H⁺] | 394 [M + Na⁺] |
| 45 | 4.43/4.48 | 368 [M + H⁺] | — |
| 46 | 4.49 | 368 [M + H⁺] | — |
| 47 | 4.32 | 396 [M + H⁺] | — |
| 48 | 6.44 | 469 [M + H⁺] | — |
| 49 | 6.77 | 483 [M + H⁺] | — |

TABLE 7-continued

| Co. No. | Retention time (min.) | Parent peak mass (ES$^+$) | Main Fragment/Aduct (ES$^+$) |
|---|---|---|---|
| 50 | 7.25 | 539 [M + H$^+$] | — |
| 52 | 5.96 | 503 [M + H$^+$] | — |
| 54 | 6.29 | 491 [M + H$^+$] | — |
| 55 | 5.64 | 507 [M + H$^+$] | — |
| 56 | 6.32 | 538 [M + H$^+$] | — |
| 58 | 6.36 | 449 [M + H$^+$] | — |
| 59 | 6.23 | 449 [M + H$^+$] | — |
| 60 | 5.97 | 433 [M + H$^+$] | — |
| 61 | 5.90 | 433 [M + H$^+$] | — |
| 62 | 6.74 | 543 [M + H$^+$] | — |
| 63 | 6.49 | 554 [M + H$^+$] | — |
| 64 | 6.47 | 483 [M + H$^+$] | — |
| 65 | 6.69 | 545 [M + H$^+$] | — |
| 66 | 4.67 | 433 [M + H$^+$] | — |
| 67 | 5.58 | 509 [M + H$^+$] | 507 [M − H$^+$] |
| 68 | 6.69 | 572 [M + H$^+$] | — |
| 69 | 7.13 | 449 [M + H$^+$] | — |
| 70 | 6.22 | 468 [M + H$^+$] | — |
| 72 | 6.41 | 501 [M + H$^+$] | — |
| 73 | 6.41 | 488 [M + H$^+$] | — |
| 74 | 6.96 | 493 [M + H$^+$] | — |
| 75 | 6.77 | 493 [M + H$^+$] | — |
| 76 | 6.76 | 535 [M + H$^+$] | — |
| 77 | 5.26 | 425 [M + H$^+$] | — |
| 78 | 5.64 | 421 [M + H$^+$] | — |
| 79 | 6.16 | 449 [M + H$^+$] | — |
| 80 | 5.41 | 451 [M + H$^+$] | 473 [M + Na$^+$] |
| 81 | 5.89 | 463 [M + H$^+$] | — |
| 82 | 5.94 | 457 [M + H$^+$] | — |
| 83 | 6.30 | 473 [M + H$^+$] | — |
| 84 | 6.16 | 437 [M + H$^+$] | — |
| 85 | 6.33 | 487 [M + H$^+$] | — |
| 86 | 5.29 | 424 [M + H$^+$] | 446 [M + Na$^+$] |
| 87 | 4.59 | 470 [M + H$^+$] | — |
| 88 | 4.62 | 438 [M + H$^+$] | — |
| 89 | 5.81 | 452 [M + H$^+$] | 474 [M + Na$^+$] |
| 90 | 5.35 | 466 [M + H$^+$] | — |
| 91 | 4.29 | 484 [M + H$^+$] | — |
| 92 | 5.33 | 482 [M + H$^+$] | 504 [M + Na$^+$] |
| 93 | 5.42 | 514 [M + H$^+$] | — |
| 94 | 4.34 | 436 [M + H$^+$] | — |
| 95 | 6.04 | 478 [M + H$^+$] | 500 [M + Na$^+$] |
| 96 | 5.05 | 546 [M + H$^+$] | — |
| 97 | 4.60 | 476 [M + H$^+$] | — |
| 98 | 5.84 | 506 [M + H$^+$] | — |
| 99 | 5.00 | 504 [M + H$^+$] | — |
| 100 | 5.81 | 472 [M + H$^+$] | 494 [M + Na$^+$] |
| 101 | 5.40 | 554 [M + H$^+$] | — |
| 102 | 5.43 | 431 [M + H$^+$] | — |
| 103 | 5.62 | 445 [M + H$^+$] | — |
| 104 | 5.68 | 443 [M + H$^+$] | — |
| 105 | 6.07 | 507 [M + H$^+$] | — |
| 106 | 6.15 | 493 [M + H$^+$] | — |
| 107 | 6.30 | 507 [M + H$^+$] | — |
| 108 | 6.11 | 468 [M + H$^+$] | — |
| 109 | 6.18 | 468 [M + H$^+$] | — |
| 110 | 5.73 | 498 [M + H$^+$] | — |
| 111 | 6.00 | 516 [M + H$^+$] | — |
| 112 | 5.89 | 518 [M + H$^+$] | — |
| 113 | 6.10 | 502 [M + H$^+$] | — |
| 114 | 6.28 | 494 [M + H$^+$] | — |
| 115 | 5.97 | 488 [M + H$^+$] | — |
| 116 | 6.45 | 459 [M + H$^+$] | — |
| 117 | 6.13 | 430 [M + H$^+$] | — |
| 118 | 6.55 | 460 [M + H$^+$] | — |
| 119 | 6.53 | 498 [M + H$^+$] | — |
| 120 | 6.59 | 498 [M + H$^+$] | — |
| 121 | 6.59 | 498 [M + H$^+$] | — |
| 122 | 6.11 | 431 [M + H$^+$] | — |
| 123 | 5.93 | 431 [M + H$^+$] | — |
| 124 | 6.26 | 477 [M + H$^+$] | — |
| 125 | 6.51 | 486 [M + H$^+$] | — |
| 126 | 6.43 | 470 [M + H$^+$] | — |
| 127 | 5.64 | 469 [M + H$^+$] | — |
| 128 | 5.02 | 384 [M + H$^+$] | — |
| 129 | 5.28 | 398 [M + H$^+$] | 420 [M + Na$^+$] |
| 130 | 5.98 | 412 [M + H$^+$] | — |
| 131 | 6.65 | 474 [M + H$^+$] | 496 [M + Na$^+$] |
| 132 | 4.85 | 425 [M + H$^+$] | — |
| 133 | 4.75 | 455 [M + H$^+$] | 477 [M + Na$^+$] |
| 134 | 3.96 | 412 [M + H$^+$] | 410 [M − H$^+$] |
| 135 | 6.09 | 440 [M + H$^+$] | 462 [M + Na$^+$] |
| 136 | 5.23 | 439 [M + H$^+$] | — |
| 137 | 5.45 | 435 [M + H$^+$] | — |
| 139 | 5.73 | 517 [M + H$^+$] | 539 [M + Na$^+$] |
| 140 | 4.77/4.83 | 368 [M + H$^+$] | — |
| 142 | 4.91 | 368 [M + H$^+$] | — |
| 143 | 4.96 | 368 [M + H$^+$] | — |
| 144 | 4.49 | 368 [M + H$^+$] | — |
| 146 | 4.59 | 382 [M + H$^+$] | — |
| 147 | 3.71 | 382 [M + H$^+$] | — |
| 148 | 4.66 | 382 [M + H$^+$] | — |
| 149 | 4.68 | 382 [M + H$^+$] | — |
| 151 | 4.21 | 382 [M + H$^+$] | — |
| 152 | 4.93 | 396 [M + H$^+$] | — |
| 154 | 4.29 | 396 [M + H$^+$] | — |
| 155 | 4.83 | 410 [M + H$^+$] | — |
| 157 | 3.56 | 396 [M + H$^+$] | — |
| 160 | 6.36 | 424 [M + H$^+$] | — |
| 162 | 6.03 | 424 [M + H$^+$] | — |
| 164 | 5.16 | 438 [M + H$^+$] | — |
| 165 | 6.43 | — | — |
| 166 | 5.79 | 410 [M + H$^+$] | — |
| 167 | 5.91 | 377 [M + H$^+$] | — |
| 168 | 5.49 | 391 [M + H$^+$] | — |
| 169 | 5.71 | 405 [M + H$^+$] | — |
| 170 | 5.42 | 405 [M + H$^+$] | — |
| 171 | 4.86/4.96 | 420 [M + H$^+$] | — |
| 172 | 4.70 | 435 [M + H$^+$] | — |
| 173 | 5.59 | 451 [M + H$^+$] | 473 [M + Na$^+$] |
| 174 | 4.76 | 448 [M + H$^+$] | — |
| 175 | 4.59 | 453 [M + H$^+$] | — |
| 176 | 5.43 | 483 [M + H$^+$] | — |
| 177 | 5.49 | 449 [M + H$^+$] | — |
| 178 | 7.05 | 535 [M + H$^+$] | — |
| 179 | 4.20 | 469 [M + H$^+$] | — |
| 180 | 4.69 | 503 [M + H$^+$] | — |
| 181 | 4.79 | 508 [M + H$^+$] | 506 [M − H$^+$] |
| 182 | 6.00 | 553 [M + H$^+$] | 551 [M − H$^+$] |
| 183 | 5.81 | 517 [M + H$^+$] | — |
| 184 | 6.09 | 591 [M + H$^+$] | — |
| 185 | 6.11 | 513 [M + H$^+$] | 511 [M − H$^+$] |
| 186 | 5.74 | 575 [M + H$^+$] | — |
| 187 | 5.03 | 435 [M + H$^+$] | 433 [M − H$^+$] |
| 188 | 5.70 | 477 [M + H$^+$] | — |
| 189 | 5.61 | 489 [M + H$^+$] | — |
| 190 | 5.99 | 523 [M + H$^+$] | 521 [M − H$^+$] |
| 191 | 5.63 | 515 [M + H$^+$] | 513 [M − H$^+$] |
| 192 | 5.18 | 522 [M + H$^+$] | — |
| 193 | 6.08 | 491 [M + H$^+$] | — |
| 194 | 5.30 | 475 [M + H$^+$] | — |
| 195 | 5.52 | 491 [M + H$^+$] | — |
| 196 | 6.06 | 611 [M + H$^+$] | — |
| 197 | 5.02 | 486 [M + H$^+$] | — |
| 198 | 6.36 | 589 [M + H$^+$] | — |
| 199 | 5.12 | 508 [M + H$^+$] | — |
| 200 | 5.09 | 435 [M + H$^+$] | — |
| 201 | 5.39 | 447 [M + H$^+$] | — |
| 202 | 6.24 | 574 [M + H$^+$] | — |
| 203 | 6.10 | 570 [M + H$^+$] | — |
| 204 | 6.05 | 580 [M + H$^+$] | — |
| 205 | 5.94 | 535 [M + H$^+$] | — |
| 206 | 6.01 | 564 [M + H$^+$] | — |
| 207 | 6.36 | 537 [M + H$^+$] | — |
| 208 | 6.01 | 564 [M + H$^+$] | — |
| 209 | 6.16 | 581 [M + H$^+$] | — |
| 210 | 5.23 | 425 [M + H$^+$] | — |
| 211 | 5.51 | 439 [M + H$^+$] | — |
| 212 | 5.82 | 453 [M + H$^+$] | — |
| 213 | 6.09 | 467 [M + H$^+$] | — |
| 214 | 5.76 | 453 [M + H$^+$] | — |
| 215 | 6.27 | 481 [M + H$^+$] | — |

TABLE 7-continued

| Co. No. | Retention time (min.) | Parent peak mass (ES+) | Main Fragment/Aduct (ES+) |
|---|---|---|---|
| 216 | 5.26 | 469 [M + H+] | — |
| 217 | 5.40 | 449 [M + H+] | — |
| 218 | 6.23 | 535 [M + H+] | — |
| 219 | 5.84 | 517 [M + H+] | — |
| 220 | 5.11 | 435 [M + H+] | — |
| 221 | 5.56 | 474 [M + H+] | — |
| 222 | 6.01 | 486 [M + H+] | 584 [M − H+] |
| 223 | 6.05 | 527 [M + H+] | — |
| 224 | 4.77 | 520 [M + H+] | — |
| 225 | 5.80 | 485 [M + H+] | — |
| 226 | 5.72 | 549 [M + H+] | — |
| 227 | 5.68 | 505 [M + H+] | — |
| 228 | 5.93 | 539 [M + H+] | 537 [M − H+] |
| 229 | 6.34 | 539 [M + H+] | — |
| 230 | 6.04 | 539 [M + H+] | 537 [M − H+] |
| 231 | 5.71 | 489 [M + H+] | — |
| 232 | 5.67 | 489 [M + H+] | — |
| 233 | 6.10 | 539 [M + H+] | 537 [M − H+] |
| 234 | 6.04 | 561 [M + H+] | — |
| 235 | 5.64 | 561 [M + H+] | — |
| 236 | 5.55 | 496 [M + H+] | — |
| 237 | 6.28 | 547 [M + H+] | — |
| 238 | 6.06 | 526 [M + H+] | — |
| 239 | 5.90 | 519 [M + H+] | — |
| 240 | 5.53 | 491 [M + H+] | — |
| 241 | 5.85 | 517 [M + H+] | — |
| 242 | 5.00 | 496 [M + H+] | — |
| 243 | 4.83 | 438 [M + H+] | — |
| 244 | 5.08 | 452 [M + H+] | — |
| 245 | 6.25 | 522 [M + H+] | — |
| 246 | 5.80 | 526 [M + H+] | — |
| 247 | 5.57 | 486 [M + H+] | — |
| 248 | 5.56 | 511 [M + H+] | 509 [M − H+] |
| 249 | 6.64 | 554 [M + H+] | 552 [M − H+] |
| 250 | 6.25 | 578 [M + H+] | 576 [M − H+] |
| 251 | 5.09 | 560 [M + H+] | 558 [M − H+] |
| 252 | 5.38 | 484 [M + H+] | 482 [M − H+] |
| 253 | 5.34 | 539 [M + H+] | 537 [M − H+] |
| 254 | 5.43 | 503 [M + H+] | 501 [M − H+] |
| 255 | 5.73 | 592 [M + H+] | 590 [M − H+] |
| 256 | 4.63 | — | 467 [M − H+] |
| 259 | 4.35/4.50 | 397 [M + H+] | — |
| 260 | 4.39/4.49 | 397 [M + H+] | — |
| 263 | 4.04/4.17 | 351 [M + H+] | 373 [M + Na+] |
| 264 | 4.20 | 351 [M + H+] | 373 [M + Na+] |
| 265 | 5.22 | 336 [M + H+] | — |
| 267 | 4.50 | 367 [M + H+] | — |
| 268 | 5.89 | 391 [M + H+] | — |
| 269 | 4.54 | 411 [M + H+] | — |
| 270 | 5.78 | 375 [M + H+] | — |
| 272 | 4.72 | 412 [M + H+] | — |
| 273 | 6.42 | 470 [M + H+] | — |
| 274 | 4.77/5.07 | 424 [M + H+] | — |
| 275 | 6.47 | 400 [M + H+] | — |
| 276 | 6.15 | 460 [M + H+] | — |
| 278 | 5.54 | 410 [M + H+] | — |
| 280 | 4.61 | 381 [M + H+] | — |
| 281 | 6.01 | 467 [M + H+] | — |
| 282 | 4.00 | 370 [M + H+] | — |
| 284 | 4.33 | 386 [M + H+] | — |
| 285 | 4.19 | 386 [M + H+] | — |
| 286 | 4.53 | 429 [M + H+] | — |
| 287 | 3.98 | 382 [M + H+] | — |
| 288 | 3.88 | 382 [M + H+] | — |

D. Pharmacological Data

EXAMPLE D.1

In Vitro Binding Affinity for $5\text{-}HT_{2A}$ and $5\text{-}HT_{2C}$ Receptors The interaction of the compounds of Formula (I) with $5\text{-}HT_{2A}$ and $5\text{-}HT_{2C}$ receptors was assessed in in vitro radioligand binding experiments. In general, a low concentration of a radioligand with a high binding affinity for the receptor is incubated with a sample of a tissue preparation enriched in a particular receptor (1 to 5 mg tissue) in a buffered medium (0.2 to 5 ml). During the incubation, the radioligands bind to the receptor. When equilibrium of binding is reached, the receptor bound radioactivity is separated from the non-bound radioactivity, and the receptor bound activity is counted. The interaction of the test compounds with the receptors is assessed in competition binding experiments. Various concentrations of the test compound are added to the incubation mixture containing the tissue preparation and the radioligand. Binding of the radioligand will be inhibited by the test compound in proportion to its binding affinity and its concentration. The affinities of the compounds for the $5\text{-}HT_2$ receptors were measured by means of radioligand binding studies conducted with: (a) human cloned $5\text{-}HT_{2A}$ receptor, expressed in L929 cells using $[^{125}I]R91150$ as radioligand and (b) human cloned $5\text{-}HT_{2C}$ receptor, expressed in CHO cells using $[^3H]$ mesulergine as radioligand.

EXAMPLE D.2

In Vitro Binding Affinity for Human $D2_L$ Receptor

Frozen membranes of human Dopamine $D2_L$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand $[^3H]$Spiperone (NEN, specific activity ~70 Ci/mmol) was diluted in assay buffer at a concentration of 2 nmol/L. Prepared radioligand (50 µl), along with 50 µl of either the 10% DMSO control, Butaclamol ($10^{-6}$ mol/l final concentration), or compound of interest, was then incubated (30 min, 37° C.) with 400 µl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful).

EXAMPLE D.3

In Vitro Determination of NET Reuptake Inhibition

Cortex from rat brain was collected and homogenised using an Ultra-Turrax T25 and a Dual homogeniser in ice-cold homogenising buffer containing Tris, NaCl and KCl (50 mM, 120 mM and 5 mM, respectively, pH 7.4) prior to dilution to an appropriate protein concentration optimised for specific and non-specific binding. Binding was performed with radioligand $[^3H]$Nixosetine (NEN, NET-1084, specific activity ~70 Ci/mmol) diluted in ice cold assay buffer containing Tris, NaCl and KCl (50 mM, 300 mM and 5 mM, respectively, pH 7.4). at a concentration of 20 nmol/L. Prepared radioligand (50 µl) was then incubated (60 min, 25° C.) with membrane preparations pre-diluted to an appropriate protein concentration (400 µl), and with 50 µl of either the 10% DMSO control, Mazindol ($10^{-6}$ mol/L final concentration), or compound of interest. Membrane-bound activity was detected by filtration through a Packard Filtermate harvester onto GF/B Unifilterplates, washed with ice-cold Tris-HCl buffer, containing NaCl and KCl (50 mM, 120 mM and 4 mM; pH 7.4; 6×0.5 ml). Filters were allowed to dry for 24 h before adding scintillation fluid. Scintillation fluid was allowed to saturate filters for 24 h before counting in a Topcount scintillation counter. Percentage specific bound and competition binding curves were calculated using S-Plus software (Insightful).

The results are given in Table 8 below in terms of $pIC_{50}$ values for the respective compounds.

TABLE 8

| Co. No | $D_{2L}$ | $5\text{-}HT_{2C}$ | $5\text{-}HT_{2A}$ | NET |
|---|---|---|---|---|
| 52 | 8.92 | 8.54 | 8.47 | 6.31 |
| 151 | 8.87 | 8.91 | 9.04 | <5 |
| 154 | 8.87 | 8.79 | 9.04 | <5 |
| 155 | 8.83 | 8.54 | 8.82 | 5.73 |
| 170 | 8.82 | 8.58 | 8.74 | 5.37 |
| 231 | 8.73 | 7.97 | n.d. | 5.07 |
| 19 | 8.69 | 8.80 | 9.46 | 5.16 |
| 248 | 8.68 | 8.21 | n.d. | 5.42 |
| 166 | 8.68 | >9 | 9.06 | 5.14 |
| 272 | 8.67 | 9.13 | 8.91 | 6.14 |
| 278 | 8.64 | 8.01 | 8.79 | <5 |
| 149 | 8.61 | 9.10 | 9.08 | <5.52 |
| 54 | 8.61 | 8.09 | 8.12 | 5.66 |
| 168 | 8.55 | 8.03 | 8.41 | <5 |
| 164 | 8.54 | 8.12 | 8.63 | 5.26 |
| 39 | 8.51 | 9.29 | 9.20 | 5.71 |
| 247 | 8.48 | 8.57 | 9.06 | 5.45 |
| 219 | 8.47 | 8.40 | n.d. | <5 |
| 224 | 8.47 | 7.89 | n.d. | <5 |
| 13 | 8.46 | 8.95 | 9.04 | 5.30 |
| 20 | 8.44 | 8.85 | 9.08 | 5.98 |
| 162 | 8.44 | 8.99 | 8.95 | <5 |
| 26 | 8.44 | 8.25 | 8.29 | <5 |
| 14 | 8.41 | 8.48 | 8.38 | 5.91 |
| 27 | 8.41 | 8.37 | 8.06 | 5.30 |
| 242 | 8.40 | 8.39 | 8.92 | 5.54 |
| 6 | 8.39 | 8.77 | 8.84 | 6.30 |
| 105 | 8.39 | 7.51 | 8.33 | <5 |
| 220 | 8.37 | 8.67 | n.d. | 5.27 |
| 24 | 8.37 | 8.84 | 8.74 | 5.57 |
| 41 | 8.37 | 8.64 | 8.74 | 5.15 |
| 40 | 8.35 | 9.56 | 8.91 | <5 |
| 148 | 8.35 | 8.71 | 8.87 | <5 |
| 244 | 8.34 | 8.37 | n.d. | 5.05 |
| 197 | 8.34 | 9.00 | 9.38 | 5.07 |
| 240 | 8.34 | 8.24 | 8.50 | <5 |
| 144 | 8.32 | 9.16 | 9.17 | <5 |
| 147 | 8.32 | 8.90 | 8.96 | <5 |
| 232 | 8.32 | 8.01 | 8.60 | 5.39 |
| 217 | 8.31 | 8.39 | n.d. | 5.05 |
| 194 | 8.30 | 8.84 | 9.33 | 5.04 |
| 22 | 8.30 | 8.43 | 8.51 | 5.60 |
| 16 | 8.29 | 8.55 | 8.25 | 5.70 |
| 227 | 8.28 | 7.95 | 8.63 | 5.04 |
| 226 | 8.27 | 8.18 | 8.70 | 4.98 |
| 195 | 8.26 | 8.79 | 9.09 | 5.11 |
| 241 | 8.26 | 8.19 | 8.29 | 5.11 |
| 23 | 8.25 | 8.42 | 8.53 | 5.42 |
| 211 | 8.23 | 8.24 | n.d. | <5 |
| 212 | 8.22 | 8.13 | n.d. | 5.15 |
| 25 | 8.22 | 8.33 | 8.80 | 5.66 |
| 230 | 8.22 | 7.90 | 8.53 | 5.24 |
| 225 | 8.22 | 7.95 | 8.51 | 5.28 |
| 17 | 8.22 | 8.33 | 8.24 | 5.76 |
| 12 | 8.20 | 8.69 | 8.93 | 6.12 |
| 60 | 8.20 | 7.60 | 8.11 | 5.81 |
| 243 | 8.17 | 8.49 | n.d. | <5 |
| 236 | 8.17 | 8.02 | 8.82 | <5 |
| 59 | 8.16 | 7.31 | 7.83 | 5.90 |
| 214 | 8.15 | 8.20 | n.d. | 5.61 |
| 186 | 8.15 | 8.63 | 8.62 | 5.45 |
| 21 | 8.14 | 8.54 | 8.72 | 5.84 |
| 69 | 8.14 | 7.10 | 7.38 | <5 |
| 1 | 8.13 | 9.43 | 9.16 | 6.32 |
| 32 | 8.13 | 9.04 | 8.66 | 5.13 |

TABLE 8-continued

| Co. No | $D_{2L}$ | $5\text{-}HT_{2C}$ | $5\text{-}HT_{2A}$ | NET |
|---|---|---|---|---|
| 15 | 8.13 | 8.20 | 8.10 | 5.68 |
| 58 | 8.13 | 7.59 | 7.96 | 6.01 |
| 28 | 8.12 | 8.75 | 7.73 | <5 |
| 221 | 8.11 | 7.96 | 8.77 | 5.14 |
| 189 | 8.11 | 8.93 | >8 | <5 |
| 210 | 8.10 | 8.38 | n.d. | 5.13 |
| 33 | 8.10 | 8.70 | 8.21 | 5.31 |
| 55 | 8.09 | 8.50 | 8.57 | 5.74 |
| 61 | 8.09 | 7.66 | 8.03 | 5.88 |
| 67 | 8.07 | 8.37 | 8.50 | 5.31 |
| 5 | 8.07 | 9.69 | >8 | 5.39 |
| 213 | 8.06 | 7.81 | n.d. | 5.36 |
| 234 | 8.06 | 7.66 | n.d. | 5.14 |
| 167 | 8.05 | 7.83 | 8.20 | 6.07 |
| 96 | 8.05 | 8.17 | 7.79 | <5 |
| 228 | 8.04 | 7.68 | n.d. | 5.10 |
| 9 | 8.04 | 8.02 | 8.04 | 5.34 |
| 275 | 8.03 | 8.66 | 8.52 | 5.49 |
| 48 | 8.02 | 7.49 | 7.51 | 5.68 |
| 3 | 8.01 | 9.57 | n.d. | 5.45 |
| 11 | 8.01 | 9.15 | 8.69 | 5.08 |
| 188 | 8.01 | 8.56 | >8 | <5 |
| 47 | 8.00 | 7.46 | 8.19 | <5 |
| 34 | 8.00 | 9.37 | 8.14 | 5.21 |
| 44 | 8.00 | 8.03 | >8 | 6.55 |
| 218 | 7.99 | 8.24 | n.d. | 5.25 |
| 216 | 7.99 | 8.21 | n.d. | <5 |
| 18 | 7.99 | 8.44 | 8.22 | 5.75 |
| 251 | 7.97 | 8.07 | n.d. | 5.44 |
| 102 | 7.97 | 7.90 | 8.33 | <5 |
| 192 | 7.95 | 8.42 | >8 | 5.13 |
| 252 | 7.94 | 8.18 | n.d. | 5.49 |
| 99 | 7.94 | 8.09 | 8.50 | <5 |
| 246 | 7.93 | 8.24 | 8.89 | 5.87 |
| 93 | 7.93 | 8.30 | 8.59 | 5.38 |
| 191 | 7.93 | 8.46 | >8 | 5.04 |
| 177 | 7.93 | 8.35 | >8 | 5.01 |
| 268 | 7.92 | 8.24 | 8.52 | <5 |
| 254 | 7.91 | 7.70 | n.d. | 5.46 |
| 137 | 7.91 | 8.22 | 8.80 | 5.19 |
| 143 | 7.90 | 8.74 | 8.87 | <5 |
| 205 | 7.90 | 8.35 | >8 | 5.07 |
| 173 | 7.88 | 8.24 | 9.14 | 5.19 |
| 85 | 7.88 | 7.20 | 7.18 | <5 |
| 31 | 7.87 | 8.49 | 8.01 | 5.39 |
| 2 | 7.86 | 9.58 | n.d. | 6.34 |
| 169 | 7.86 | 8.54 | 8.50 | 5.79 |
| 66 | 7.86 | 7.43 | 8.13 | 5.36 |
| 196 | 7.85 | 8.30 | 8.44 | 5.56 |
| 142 | 7.84 | 8.50 | 9.24 | 5.62 |
| 160 | 7.84 | 8.54 | 8.30 | <5 |
| 29 | 7.84 | 8.47 | 8.14 | 5.07 |
| 229 | 7.83 | 7.62 | n.d. | <5 |
| 233 | 7.83 | 7.51 | n.d. | 5.28 |
| 269 | 7.83 | 8.14 | 8.25 | 5.15 |
| 222 | 7.82 | 7.71 | n.d. | <5 |
| 174 | 7.82 | 8.66 | 8.79 | <5 |
| 193 | 7.81 | 8.58 | 8.85 | 5.28 |
| 117 | 7.81 | 8.60 | 8.83 | 5.34 |
| 185 | 7.81 | 7.97 | 8.44 | <5 |
| 64 | 7.81 | 7.54 | 7.58 | 5.57 |
| 200 | 7.81 | 8.09 | >8 | <5 |
| 215 | 7.80 | 770 | n.d. | 5.13 |
| 274 | 7.79 | 9.04 | n.d. | <5 |
| 30 | 7.79 | 8.24 | 7.98 | <5 |
| 4 | 7.79 | 8.68 | >8 | 5.23 |
| 141 | 7.78 | 8.94 | 8.99 | 5.32 |
| 203 | 7.78 | 8.51 | 8.44 | 5.35 |
| 276 | 7.77 | 8.94 | 8.99 | <5 |
| 152 | 7.77 | 8.38 | 8.73 | 5.42 |
| 46 | 7.76 | 8.96 | n.d. | 5.62 |
| 101 | 7.76 | 7.92 | 8.24 | 5.05 |
| 223 | 7.75 | 7.63 | n.d. | 5.07 |
| 187 | 7.74 | 8.94 | 9.37 | <5 |
| 175 | 7.74 | 8.76 | 9.12 | <5 |
| 281 | 7.74 | 7.87 | 8.39 | <5 |
| 235 | 7.73 | 7.87 | n.d. | 5.04 |
| 128 | 7.73 | 7.93 | 8.36 | 5.58 |

TABLE 8-continued

| Co. No | $D_{2L}$ | $5\text{-}HT_{2C}$ | $5\text{-}HT_{2A}$ | NET |
|---|---|---|---|---|
| 57 | 7.73 | 7.75 | 8.14 | <5 |
| 73 | 7.73 | 7.33 | 7.69 | 5.44 |
| 131 | 7.71 | 7.51 | n.d. | 5.62 |
| 82 | 7.71 | 8.49 | 8.67 | <5 |
| 273 | 7.71 | 8.24 | 8.48 | <5 |
| 103 | 7.71 | 7.30 | 8.11 | <5 |
| 255 | 7.69 | 7.69 | n.d. | 5.25 |
| 112 | 7.69 | 7.66 | 8.48 | 6.03 |
| 70 | 7.69 | 7.80 | 8.14 | 6.15 |
| 238 | 7.67 | 8.25 | n.d. | 5.11 |
| 36 | 7.66 | 8.33 | 7.91 | 5.39 |
| 130 | 7.66 | 8.27 | >8 | 5.45 |
| 127 | 7.65 | 8.38 | 9.60 | 5.42 |
| 88 | 7.64 | 8.26 | 9.42 | 5.19 |
| 208 | 7.64 | 8.10 | 8.39 | <5 |
| 245 | 7.63 | 7.64 | n.d. | 5.40 |
| 202 | 7.62 | 8.09 | 8.46 | 5.79 |
| 136 | 7.61 | 8.48 | 8.80 | 7.15 |
| 253 | 7.61 | 7.99 | 8.68 | 5.82 |
| 260 | 7.61 | 8.51 | 8.65 | 6.04 |
| 184 | 7.60 | 8.24 | 8.85 | 5.41 |
| 198 | 7.60 | 7.79 | 8.09 | 5.12 |
| 87 | 7.59 | 8.51 | 8.90 | 5.23 |
| 207 | 7.59 | 8.17 | 8.26 | 5.21 |
| 84 | 7.59 | 7.60 | 8.09 | <5 |
| 183 | 7.59 | 8.94 | >8 | <5 |
| 118 | 7.58 | 8.12 | 8.31 | 5.55 |
| 56 | 7.58 | 7.99 | 8.22 | 5.25 |
| 72 | 7.57 | 7.22 | 7.51 | 5.93 |
| 111 | 7.56 | 8.01 | 8.41 | 5.51 |
| 108 | 7.53 | 7.79 | 8.34 | 5.49 |
| 129 | 7.53 | 8.12 | >8 | 6.38 |
| 90 | 7.51 | 7.70 | 8.79 | 5.35 |
| 104 | 7.51 | 7.55 | 8.08 | <5 |
| 74 | 7.51 | 6.79 | 6.90 | 5.50 |
| 182 | 7.50 | 8.08 | 8.37 | 5.16 |
| 209 | 7.50 | 7.92 | 8.33 | 5.28 |
| 286 | 7.50 | 7.81 | 8.33 | <5 |
| 285 | 7.49 | 7.76 | 8.56 | <5 |
| 135 | 7.49 | 7.78 | 7.95 | 5.61 |
| 37 | 7.49 | 8.10 | 7.65 | <5 |
| 49 | 7.48 | 6.92 | 7.47 | 5.59 |
| 77 | 7.47 | 7.88 | 8.51 | 5.44 |
| 94 | 7.45 | 8.66 | 9.41 | 4.97 |
| 81 | 7.45 | 8.30 | 9.14 | <5 |
| 199 | 7.45 | 8.92 | 8.19 | <5 |
| 78 | 7.44 | 8.05 | 8.65 | <5 |
| 110 | 7.44 | 7.32 | 8.21 | 5.24 |
| 250 | 7.43 | 7.69 | n.d. | 5.41 |
| 91 | 7.43 | 7.83 | 8.94 | 5.39 |
| 180 | 7.43 | 8.41 | 8.61 | <5 |
| 116 | 7.43 | 7.70 | 8.01 | 5.14 |
| 266 | 7.42 | 8.42 | 8.09 | 6.61 |
| 179 | 7.42 | 8.42 | >8 | <5 |
| 89 | 7.41 | 8.18 | 8.55 | <5 |
| 165 | 7.41 | 7.56 | 7.97 | 5.44 |
| 206 | 7.39 | 8.03 | 8.61 | 5.77 |
| 123 | 7.39 | 8.14 | 8.56 | 5.55 |
| 201 | 7.38 | 7.98 | 9.21 | <5 |
| 134 | 7.38 | 8.86 | >8 | 7.37 |
| 98 | 7.37 | 7.71 | 8.47 | 5.02 |
| 92 | 7.36 | 7.81 | 8.59 | <5 |
| 172 | 7.36 | 7.80 | 7.82 | 5.17 |
| 256 | 7.35 | 7.35 | n.d. | 5.19 |
| 80 | 7.35 | 7.78 | 8.97 | 5.43 |
| 79 | 7.35 | 7.29 | 8.32 | <5 |
| 106 | 7.35 | 7.21 | 7.78 | 5.02 |
| 114 | 7.34 | 7.68 | 8.21 | 5.96 |
| 124 | 7.32 | 7.51 | 8.05 | 5.64 |
| 190 | 7.32 | 8.56 | >8 | <5 |
| 239 | 7.31 | 7.64 | n.d. | <5 |
| 100 | 7.30 | 8.43 | 8.61 | <5 |
| 113 | 7.30 | 7.62 | 7.96 | 5.62 |
| 178 | 7.30 | 8.03 | >8 | <5 |
| 86 | 7.26 | 8.52 | 9.08 | 5.15 |
| 139 | 7.25 | 7.61 | n.d. | <5 |
| 181 | 7.24 | 8.12 | 8.32 | <5 |
| 43 | 7.24 | 8.89 | >8 | 5.77 |
| 237 | 7.23 | 7.42 | n.d. | 5.10 |
| 75 | 7.20 | 7.01 | 7.76 | 5.79 |
| 204 | 7.18 | 7.98 | 8.50 | 5.46 |
| 76 | 7.17 | 6.99 | 7.18 | 6.07 |
| 95 | 7.16 | 8.12 | 8.76 | 5.02 |
| 50 | 7.15 | 6.98 | 7.46 | 5.67 |
| 284 | 7.14 | 7.38 | 7.98 | <5 |
| 63 | 7.13 | 7.30 | 7.56 | 6.25 |
| 62 | 7.12 | 6.97 | 7.32 | 5.46 |
| 121 | 7.11 | 7.11 | 7.88 | 5.45 |
| 146 | 7.09 | 7.94 | 7.78 | <5 |
| 107 | 7.09 | 6.48 | 7.08 | <5 |
| 68 | 7.04 | 6.93 | 7.17 | 5.62 |
| 65 | 6.97 | 6.83 | 7.15 | 5.75 |
| 115 | 6.95 | 7.65 | 8.13 | 6.31 |
| 157 | 6.88 | 8.14 | 7.91 | <5 |
| 109 | 6.88 | 7.41 | 7.84 | 6.58 |
| 7 | 6.85 | 8.53 | >8 | 5.79 |
| 267 | 6.81 | 7.65 | 7.84 | 5.10 |
| 119 | 6.80 | 7.29 | 7.99 | 5.39 |
| 262 | 6.76 | 7.65 | 7.60 | 5.16 |
| 283 | 6.70 | n.d. | n.d. | n.d. |
| 126 | 6.67 | 7.10 | 8.05 | 5.01 |
| 270 | 6.67 | 7.45 | 7.18 | 5.78 |
| 38 | 6.65 | 7.81 | 7.87 | 5.29 |
| 259 | 6.59 | 7.64 | n.d. | 5.38 |
| 125 | 6.59 | 7.11 | 7.76 | <5 |
| 171 | 6.55 | 7.74 | 7.55 | 5.85 |
| 45 | 6.46 | 8.66 | n.d. | 7.33 |
| 158 | 6.45 | 7.48 | 7.63 | <5 |
| 133 | 6.45 | 7.46 | 7.31 | 6.03 |
| 120 | 6.44 | 7.06 | 7.45 | <5 |
| 132 | 6.41 | 7.48 | 7.48 | 5.24 |
| 10 | 6.36 | 7.87 | 7.76 | <5 |
| 263 | 6.26 | 7.88 | 6.60 | 5.54 |
| 287 | 6.17 | 6.54 | 7.62 | <5 |
| 282 | 6.10 | 6.93 | 7.00 | <5 |
| 288 | 6.08 | 6.71 | 7.18 | <5 |
| 264 | 5.65 | 7.72 | 6.78 | 5.38 |
| 280 | 5.40 | 6.53 | 6.53 | <5 | n.d. = not determined

E. COMPOSITION EXAMPLES

"Active ingredient" (A.I.) as used throughout these examples relates to a compound of Formula (I), a pharmaceutically acceptable acid or base addition salt thereof, an N-oxide form thereof or a quaternary ammonium salt thereof.

EXAMPLE E.1

Oral Solution

Methyl 4-hydroxybenzoate (9 g) and propyl 4-hydroxybenzoate (1 g) were dissolved in boiling purified water (4 l). In 3 l of this solution were dissolved first 2,3-dihydroxybutanedioic acid (10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE E.2

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.

Coating

To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

EXAMPLE E.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and A.I. (4 g). The solution was cooled to room temperature and supplemented with water for injection q.s. ad 1000 ml, giving a solution comprising 4 mg/ml of A.I. The solution was sterilized by filtration and filled in sterile containers.

The invention claimed is:
1. A compound selected from the group of:
   1-(11-fluoro-3,3a,8,12b-tetrahydro-2H-1-oxa-dibenzo[e,h]azulen-2-ylmethyl)-pyrrolidin-3-one;
   1-(11-fluoro-3,3a,8,12b-tetrahydro-2H-1-oxa-dibenzo[e,h]azulen-2-ylmethyl)-pyrrolidine-3-carboxylic acid methyl ester;
   1-(11-fluoro-3,3a,8,12b-tetrahydro-2H-1-oxa-dibenzo[e,h]azulen-2-ylmethyl)-4-furan-3-ylmethyl-piperazine;
   cyclopropyl-[4-(11-fluoro-3,3a,8, 12b-tetrahydro-2H-1-oxa-dibenzo[e,h]azulen-2-ylmethyl)-piperazin-1-yl]-methanone;
   [4-(11-fluoro-3,3a,8,12b-tetrahydro-2H-1-oxa-dibenzo[e,h]azulen-2-ylmethyl)-piperazin-1-yl]-phenyl-methanone;
   4-(11-fluoro-3,3a,8,12b-tetrahydro-2H-1-oxa-dibenzo[e,h]azulen-2-ylmethyl)-piperazine-1-carboxylic acid cyclopropylamide;
   [4-(11-fluoro-3,3a,8,12b-tetrahydro-2H-1-oxa-dibenzo[e,h]azulen-2-ylmethyl)-morpholin-2-yl]-methanol;
   1-(11-fluoro-3,3a,8,12b-tetrahydro-2H-1-oxa-dibenzo[e,h]azulen-2-ylmethyl)-piperidin-3-ol;
   [1-(11-fluoro-3,3a,8,12b-tetrahydro-2H-1-oxa-dibenzo[e,h]azulen-2-ylmethyl)-piperidin-3-yl]-methanol;
   [1-(11-fluoro-3,3a,8,12b-tetrahydro-2H-1-oxa-dibenzo[e,h]azulen-2-ylmethyl)-piperidin-4-yl]-methanol;
   3-[1-(11-fluoro-3,3a,8, 12b-tetrahydro-2H-1-oxa-dibenzo[e,h]azulen-2-ylmethyl)-piperidin-4-yl]-propan-1-ol;
   1-(11-fluoro-3,3a,8,12b-tetrahydro-2H-1-oxa-dibenzo[e,h]azulen-2-ylmethyl)-piperidine-4-carboxylic acid ethyl ester;
   [1-(11-fluoro-3,3a,8,12b-tetrahydro-2H-1-oxa-dibenzo[e,h]azulen-2-ylmethyl)-piperidin-4-yl]-acetic acid ethyl ester;
   [5-(11-fluoro-3,3a,8,12b-tetrahydro-2H-1-oxa-dibenzo[e,h]azulen-2-ylmethyl)-octahydro-furo[3,2-c]pyridin-2-yl]-methanol;
   1-(11-fluoro-3,3a,8,12b-tetrahydro-2H-1-oxa-dibenzo[e,h]azulen-2-ylmethyl)-pyrrolidin-3-ol;
   1-(11-fluoro-3,3a,8,12b-tetrahydro-2H-1-oxa-dibenzo[e,h]azulen-2-ylmethyl)-piperidin-4-ol;
   2-[1-(11-fluoro-3,3a,8,12b-tetrahydro-2H-1-oxa-dibenzo[e,h]azulen-2-ylmethyl)-piperidin-4-yl]-ethanol;
   1-(11-fluoro-3,3a,8,12b-tetrahydro-2H-1-oxa-dibenzo[e,h]azulen-2-ylmethyl)-4-methoxymethyl-piperidin-4-ol;
   2-(11-fluoro-3,3a,8,12b-tetrahydro-2H-1-oxa-dibenzo[e,h]azulen-2-ylmethyl)-6,7-dimethoxy-1,2,3,4-tetrahydro-isoquinoline; and
   8-(11-fluoro-3,3a,8,12b-tetrahydro-2H-1-oxa-dibenzo[e,h]azulen-2-ylmethyl)-1,4-dioxa-8-aza-spiro[4.5]decane,
   a pharmaceutically acceptable acid or base addition salt thereof, an N-oxide form thereof or a quaternary ammonium salt thereof.

2. A compound according to 1, wherein the compound is the [2R-(2α,3aα,12bβ)]-isomer.

3. Pharmaceutical composition comprising a pharmaceutically acceptable carrier and, as active ingredient, a therapeutically effective amount of a compound according to claim 1.

4. A compound of claim 1, wherein the compound is an oxalate salt.

5. A compound of claim 4, wherein the compound is a (1:1) oxalate salt.

6. A compound of claim 1, wherein the compound is a trifluoroacetate salt.

7. A compound of claim 6 wherein the compound is a (1:1) trifluoroacetate salt.

* * * * *